US012649603B2

(12) United States Patent　　　　　(10) Patent No.:　US 12,649,603 B2
Bott et al.　　　　　　　　　　　　　　(45) Date of Patent:　　　Jun. 9, 2026

(54) PRODUCTION SYSTEM AND PROCESS FOR PRODUCING A PRODUCT

(71) Applicant: KyooBe Tech GmbH, Leinfelden-Echterdingen (DE)

(72) Inventors: Mario Bott, Deeingen unter Teck (DE); Lena Schober, Grossbottwar (DE); David Weller, Esslingen am Neckar (DE)

(73) Assignee: KyooBe Tech GmbH, Leinfelden-Echterdingen (DE)

( * ) Notice: Subject to any disclaimer, the term of this patent is extended or adjusted under 35 U.S.C. 154(b) by 108 days.

(21) Appl. No.: 18/414,586

(22) Filed: Jan. 17, 2024

(65) Prior Publication Data

US 2024/0199265 A1　　　Jun. 20, 2024

Related U.S. Application Data

(63) Continuation of application No. PCT/EP2022/070060, filed on Jul. 18, 2022.

(30) Foreign Application Priority Data

Jul. 20, 2021　(DE) ..................... 10 2021 207 742.0

(51) Int. Cl.
　　B65B 69/00　　　　(2006.01)
　　B25J 21/00　　　　(2006.01)
　　　　　　　(Continued)

(52) U.S. Cl.
　　CPC ............. B65B 69/00 (2013.01); B25J 21/005 (2013.01); B65B 3/003 (2013.01); B65B 55/027 (2013.01);
　　　　　　　(Continued)

(58) Field of Classification Search
　　CPC ....... B65B 69/00; B65B 3/003; B65B 55/027; B65B 55/08; B65B 55/10; B65B 55/24; B65B 57/00; B65B 2210/06; B65B 55/16; B25J 21/005; C12M 37/00; G06Q 10/087; B08B 2230/01; B08B 3/02; B08B 7/0035; F24F 11/72; F24F 2110/10; F24F 2110/20; F24F 3/167
　　See application file for complete search history.

(56) References Cited

U.S. PATENT DOCUMENTS 5,737,827　A　　4/1998　Kuse et al.
5,783,156　A　　7/1998　Renzi et al.
　　　　　　　(Continued)

FOREIGN PATENT DOCUMENTS

CH　　　　　699754 A1　　4/2010
DE　　　19921072 A1　　11/2000
　　　　　　　(Continued)

OTHER PUBLICATIONS

U.S. Appl. No. 18/414,400, filed Jan. 16, 2024.
　　　　　　　(Continued)

*Primary Examiner* — Michael Jared Walker
(74) *Attorney, Agent, or Firm* — ASLAN LAW, P.C.

(57) ABSTRACT

The present invention relates to a production system (10), in particular for producing biological-pharmaceutical products (20), and/or a method for producing a product (20), in particular a biological-pharmaceutical product (20).

10 Claims, 25 Drawing Sheets

(51) Int. Cl.

| | |
|---|---|
| *B65B 3/00* | (2006.01) |
| *B65B 55/02* | (2006.01) |
| *B65B 55/08* | (2006.01) |
| *B65B 55/10* | (2006.01) |
| *B65B 55/24* | (2006.01) |
| *B65B 57/00* | (2006.01) |
| *C12M 1/12* | (2006.01) |
| *G06Q 10/087* | (2023.01) |

(52) U.S. Cl.

CPC .............. *B65B 55/08* (2013.01); *B65B 55/10* (2013.01); *B65B 55/24* (2013.01); *B65B 57/00* (2013.01); *C12M 37/00* (2013.01); *G06Q 10/087* (2013.01)

(56) References Cited

U.S. PATENT DOCUMENTS

| | | | |
|---|---|---|---|
| 5,827,118 A | 10/1998 | Johnson et al. | |
| 5,884,392 A | 3/1999 | Lafond | |
| 6,502,054 B1 | 12/2002 | Mooring et al. | |
| 6,629,053 B1 * | 9/2003 | Mooring ............ | G05B 19/4083 |
| | | | 702/94 |
| 7,134,825 B1 | 11/2006 | Schmutz et al. | |
| 7,610,115 B2 | 10/2009 | Rob et al. | |
| 9,279,099 B2 | 3/2016 | Okano et al. | |
| 9,765,980 B2 | 9/2017 | Holtz et al. | |
| 10,689,873 B2 * | 6/2020 | Biffiger ................... | E04H 1/005 |
| 11,111,048 B2 | 9/2021 | Franke et al. | |
| 11,535,412 B2 | 12/2022 | Guldimann et al. | |
| 2003/0044262 A1 | 3/2003 | Inui | |
| 2003/0050005 A1 | 3/2003 | Nakao | |
| 2005/0193643 A1 | 9/2005 | Pettus | |
| 2006/0136095 A1 | 6/2006 | Rob et al. | |
| 2006/0275888 A1 | 12/2006 | Hibino et al. | |
| 2008/0251473 A1 | 10/2008 | Rebstock et al. | |
| 2011/0067781 A1 | 3/2011 | Osborne | |
| 2015/0250678 A1 | 9/2015 | Eliuk et al. | |
| 2015/0335531 A1 | 11/2015 | Yuyama et al. | |
| 2016/0168521 A1 | 6/2016 | Mottahedeh | |
| 2017/0321443 A1 | 11/2017 | Biffiger et al. | |
| 2018/0040493 A1 | 2/2018 | Kawai et al. | |
| 2018/0043347 A1 | 2/2018 | Holtz et al. | |
| 2019/0344257 A1 | 11/2019 | Naing et al. | |
| 2020/0290756 A1 | 9/2020 | Deutschle et al. | |
| 2021/0002007 A1 | 1/2021 | Anatrini | |
| 2021/0199484 A1 | 7/2021 | Seal et al. | |
| 2022/0380710 A1 | 12/2022 | Merz et al. | |
| 2023/0002088 A1 | 1/2023 | Merz et al. | |

FOREIGN PATENT DOCUMENTS

| | | | | |
|---|---|---|---|---|
| DE | 69614592 T2 | 5/2002 | | |
| DE | 202005007849 U1 | 9/2005 | | |
| DE | 102006028057 A1 | 4/2007 | | |
| DE | 60035164 T2 | 2/2008 | | |
| DE | 102008032407 A1 | 1/2010 | | |
| DE | 202010009656 U1 | 10/2010 | | |
| DE | 102009031018 A1 | 1/2011 | | |
| DE | 102009040555 A1 | 3/2011 | | |
| DE | 102010032143 A1 | 1/2012 | | |
| DE | 202014105336 U1 | 11/2014 | | |
| DE | 102014111632 A1 * | 2/2016 | ......... | B65B 69/0033 |
| DE | 102017124908 A1 | 4/2019 | | |
| DE | 102020102758 A1 | 8/2021 | | |
| DE | 102020102768 A1 | 8/2021 | | |
| EP | 1612262 A1 | 1/2006 | | |
| EP | 2042814 A2 | 4/2009 | | |
| EP | 2457549 A1 | 5/2012 | | |
| EP | 2457550 A1 | 5/2012 | | |
| EP | 2168880 B1 * | 7/2012 | ......... | B65B 69/0033 |
| EP | 2604679 A1 | 6/2013 | | |
| EP | 3736219 A1 | 11/2020 | | |
| EP | 3815877 A1 | 5/2021 | | |
| EP | 3819092 A1 | 5/2021 | | |
| EP | 3845627 A1 | 7/2021 | | |
| JP | H0781754 A | 3/1995 | | |
| JP | 2002179206 A | 6/2002 | | |
| WO | WO 2004108270 A2 | 12/2004 | | |
| WO | WO 2006102416 A2 | 9/2006 | | |
| WO | WO 2007105844 A1 | 9/2007 | | |
| WO | WO-2009147252 A1 * | 12/2009 | ......... | G07F 17/0092 |
| WO | WO 2010045750 A1 | 4/2010 | | |
| WO | WO 2011022325 A2 | 2/2011 | | |
| WO | WO 2011029427 A1 | 3/2011 | | |
| WO | WO 2015023924 A2 | 2/2015 | | |
| WO | WO 2017221155 A1 | 12/2017 | | |
| WO | WO 2018019785 A1 | 2/2018 | | |

OTHER PUBLICATIONS

U.S. Appl. No. 18/414,584, filed Jan. 17, 2024.
U.S. Appl. No. 18/414,586, filed Jan. 17, 2024.
U.S. Appl. No. 18/414,587, filed Jan. 17, 2024.
U.S. Appl. No. 18/414,589, filed Jan. 17, 2024.
U.S. Appl. No. 18/414,592, filed Jan. 17, 2024.

* cited by examiner

704

702

410

302

200

218

PRODUCTION SYSTEM AND PROCESS FOR PRODUCING A PRODUCT

RELATED APPLICATION

This application is a continuation of international application No. PCT/EP2022/070060 filed on Jul. 18, 2022, and claims the benefit of German application No. 10 2021 207 742.0 filed on Jul. 20, 2021, which are incorporated herein by reference in their entirety and for all purposes.

FIELD OF DISCLOSURE

The present invention relates to a production system and a method for producing a product. In particular, the present invention relates to a production system for producing biological-pharmaceutical products and a method for producing biological-pharmaceutical products.

BACKGROUND

Conventional production systems in particular in the pharmaceutical sector for personalized therapeutics have a high proportion of manual interventions. Although this makes it possible to produce these therapeutics at a high personalized level or in a highly personalized manner, high costs are associated with such individual and/or small productions and high fluctuations in quality, and also, associated therewith, high production rejections and/or bad parts are reported. Furthermore, there is no possibility for a large-scale application and/or industrial production of individual and/or small batch sizes.

SUMMARY OF THE INVENTION

The object of the present invention is to solve the above-mentioned problems, in particular to be able to produce individual and/or small batch sizes of products in the pharmaceutical sector efficiently and in particular in a constant quality.

According to the invention, this object is achieved by the features of claim 1. Advantageous developments of the invention are described in the dependent claims.

A production system according to the invention, in particular for producing biological-pharmaceutical products, preferably comprises:

an, in particular suitable, clean room region, an airlock device for supplying an object from the surroundings of the production system into the, in particular suitable, clean room region and/or for removing an object from the clean room region, a handling device for moving the object within the clean room region, and a storage device which is arranged within the clean room region and which comprises a plurality of storage spaces for receiving a plurality of objects.

An object, in particular the object from the surroundings of the production system for feeding into the clean room region and/or the object for removal from the clean room region, can comprise at least one of the following:

a reactant, in particular a material having cells, for example a starting material having cells, and/or a biological-pharmaceutical material and/or a biological-pharmaceutical workpiece, an intermediate product, in particular an intermediate product having cells and/or a biological-pharmaceutical intermediate product, a tool or a tool unit, in particular a reactant- and/or product-contacting tool or a reactant- and/or product-contacting tool unit and/or in particular a non-reactant-and/or non-product-contacting tool or a non-reactant-and/or non-product-contacting tool unit, one or more consumable materials, a product, for example the product to be produced, in particular a biological-pharmaceutical product, for example the biological-pharmaceutical product to be produced.

It should be understood that the preceding list is exemplary and not exhaustive.

Alternatively or additionally, it can be provided that the object comprises one or more and/or a combination of the above-described list elements.

The reactant can have cells and/or a biological material which differs in particular from cells.

The reactant can be at least partially liquid, and/or at least partially semi-solid, and/or at least partially solid.

Alternatively, the reactant can be completely liquid, or completely semi-solid, or completely solid.

The cells of the reactant can in particular be present, for example can be formed as, a cell suspension, for example as cells in a suspension culture, or adherent cells, for example as cells on a culture surface in particular of a container or reactant container, for example a culture vessel and/or a bag.

The cells can be at least partially fresh and/or are at least partially in a frozen state, whereby, to a certain extent, the reactant can, for example, be present in a liquid, a semi-solid and/or a solid state.

It can be provided that the reactant is arranged in a container or reactant container, in particular a vessel, for example a culture vessel, a cell culture vessel, a bottle, a vial, a bag, a cassette (for example a cassette made of a hard plastic, in particular a biocompatible hard plastic) and/or a titer plate (for example a microtiter plate). It can be provided that the container or reactant container, including the examples mentioned above, is in each case suitable, in particular biocompatible, partially or completely coated and/or partially or completely uncoated.

It can be provided that a container for receiving and processing a reactant has a volume between 1 μl and 1000 ml, in particular between 1 μl and 500 ml, furthermore in particular between 1 μl and 1000 μl. The volume can be, for example, 250 ml or 750 ml. Furthermore, it can be provided that the volume is less than 1 μl and/or greater than 1000 ml.

The product can be a biological-pharmaceutical product for a personalized therapy.

To a certain extent, the biological-pharmaceutical product can be a personalized therapeutic agent.

It can be provided that a, or the, personalization is provided for a patient or a patient group, in other words for one or more patients.

The biological-pharmaceutical product can be, for example, a cell therapeutic agent, for example an autologous and/or an allogeneic cell therapeutic agent, or a gene therapeutic agent, for example an autologous and/or an allogeneic gene therapeutic agent.

The clean room region can define an aseptic production area.

The clean room region can have at least a clean room class CNC (i.e., controlled not classified) according to the good manufacturing practice (GMP).

It can be conceivable that the clean room region has at least one of the clean room classes D, C, B or A according to the good manufacturing practice (GMP).

The clean room region can have a positive pressure, in particular for protecting reactants and/or products, in particular with regard to sterility. In addition, the clean room region can have a negative pressure in a region of the clean room region separated from the positive pressure region, in particular for protecting a human operator or user from reactants and/or products.

The production system can have a system for setting the ambient properties of the clean room region.

The system for setting the ambient properties of the clean room region can in particular have an air device by means of which an air pressure, in particular a positive pressure and/or a negative pressure, can be set in the clean room region.

Additionally or alternatively, the air device can be used to adjust an air supply and/or an air discharge into or out of the clean room region and/or an air circulation, in particular including an air return, within the clean room region, in particular via one or more filter devices of the system for setting the ambient properties.

To a certain extent, a positive pressure region in the production system can define the clean room region and/or can be the clean room region.

The production system can have a housing in particular for separating/delimiting the clean room region with respect to the surroundings of the production system and for maintaining its clean room class, wherein the housing surrounds the clean room region, in particular the clean room region and the airlock device.

It can be provided that the housing surrounds the entire production system to a certain extent.

The airlock device can be configured to supply an object from the surroundings of the production system via the or through the housing into the clean room region and/or to remove an object from the clean room region via the or through the housing.

To a certain extent, the airlock device can serve as at least one interface, for example as at least one inlet and/or as at least one outlet, of the housing which surrounds at least the clean room region, to the surroundings of the production system.

Additionally or alternatively, it can be provided that the airlock device has at least one inlet airlock and at least one outlet airlock. In other words, the airlock device can have one or more inlet airlocks and one or more outlet airlocks. This can serve in particular for directed object guidance or a directed object flow.

Additionally or alternatively, it can be provided that the inlet airlocks and the outlet airlocks can be categorized with respect to an object for which they are to provide an airlock and can be provided accordingly as part of the airlock device. For example, an inlet airlock and an outlet airlock for reactants and/or for consumable material and/or for tools or tool units and/or for waste can be provided in each case, or for any combination thereof.

It can, for example, be provided that the inlet airlock and/or the outlet airlock serve as an interface of the clean room region to the surroundings of the production system.

The airlock device can have one or more maintenance airlocks via which the clean room region is accessible from the surroundings of the production system, in particular for human operators or users.

Additionally or alternatively, it can be provided that one or more maintenance airlocks are designed as a device of the production system that is separate from the airlock device in each case.

Additionally or alternatively, it can be provided that the clean room region has a plurality of clean room sub-regions.

In other words, the clean room region can be subdivided into a plurality of clean room sub-regions.

For example, it is conceivable that the handling device and the storage device are arranged in a common clean room sub-region or in different clean room sub-regions.

The clean room sub-regions can have an identical clean room class or different clean room classes.

It can be provided that one or more clean room sub-regions have different positive pressures.

In other words, one or more clean room sub-regions can have pressure differences with respect to the positive pressures.

A clean room class can be one of the following clean room classes:

clean room class CNC,
clean room class D,
clean room class C,
clean room class B,
clean room class A,
in each case according to the good manufacturing practice (GMP).

Each clean room sub-region can be associated with a corresponding sub-region housing in particular for separating or delimiting the corresponding clean room sub-region and for maintaining its respective clean room class.

Additionally or alternatively, clean room sub-regions which have an identical clean room class can be associated with a common sub-region housing.

The corresponding sub-region housing and/or the common sub-region housing can each be configured as a part of the housing of the production system.

Additionally or alternatively, the corresponding sub-region housing and/or the common sub-region housing can be designed separately, in particular independently.

Each sub-region housing can be associated with at least one sub-region airlock device which can be designed as a part of this sub-region housing.

Additionally or alternatively, the at least one sub-region airlock device can be designed separately, in particular independently.

Each sub-region airlock device can be configured to supply an object from one clean room sub-region into another clean room sub-region and/or to remove an object from one clean room sub-region into another clean room sub-region.

It can be provided that a clean room sub-region is subdivided into a plurality of sub-clean room sub-regions. For a possible embodiment and/or configuration of the sub-clean room sub-regions, reference is made to the description of the clean room sub-regions.

It can be provided that one or more clean room sub-regions with clean room class A are set up in relation to processes and/or procedures, in particular for a treatment and/or a transport and/or a storage and/or an analysis and/or a packaging and/or an unpacking, in which there is contact with a reactant, intermediate product and/or product, or in which there may be a, in particular theoretical, possibility of such a contact, for example by means of one or more objects which can lead to contamination, for example by means of one or more tools and/or one or more consumable materials and/or one or more devices of the production system.

It can be provided that one or more clean room sub-regions with clean room class B are set up in relation to the airlock device, the storage device, in particular the storage spaces of the storage device, the handling device, and/or a cleaning device of the production system. Additionally or alternatively, in this regard, one or more clean room sub-regions with clean room class A can also be set up.

It can be provided that one or more clean room sub-regions with the clean room class C or D are set up in relation to a storage transport device of the storage device.

It can be provided that one or more clean room sub-regions with the clean room class CNC are set up in relation to one or more physical residual regions of the production system. In particular, these one or more physical residual regions can be provided for technical structures and or machines which are required for the general operation of the production system and/or parts of the production system.

The production system can have one or more (electrical) power sources and/or one or more interfaces connectable to one or more (electrical) power sources, which interfaces are arranged within the clean room region, in particular the housing, and which are configured to supply at least one of the components comprised by the production system or a part of the production system with electrical current, which (component) or which (part) is assigned to the one or more power sources, for example via the one or more interfaces.

Additionally or alternatively, it can be provided that one or more (electrical) power sources are arranged in the surroundings of the production system and/or are arranged spatially separated or separately, which are connectable or connected to the production system.

The production system can have one or more control units which are arranged within the clean room region, in particular the housing, or on the production system, and which are designed and programmed to provide closed-loop and/or open-loop control for at least one of the components comprised by the production system or a part of the production system, which (component) or which (part) are assigned to the one or more control units.

Additionally or alternatively, it can be provided that one or more control units are arranged in the surroundings of the production system and/or are arranged spatially separated or separately and, in particular can be connected or are connected wirelessly and/or in a wired manner to the production system, for example by means of one or more communication interfaces of the production system.

It can be provided that one or more control units can be connected to one or more, in particular external, i.e., not comprised by the production system, data handling systems and/or computer systems, in particular wirelessly or in a wired manner, for example by means of one or more communication interfaces of the production system.

Additionally or alternatively, it can be provided that the control units are programmed and designed to identify, code and/or assign one or more objects in the production system, in particular by means of an ID assigned to an object, wherein, optionally, the ID can be assigned to a corresponding object in particular by means of RFID means and/or barcode means.

The production system can comprise a plurality of work-piece carriers which serve to receive objects, inter alia reactants and/or tools and/or consumable materials.

It can be provided that one or more clean room sub-regions with clean room class A are set up in relation to the workpiece carriers. For example, it can be provided.

Additionally or alternatively, it can be provided that one or more clean room sub-regions with clean room class B are set up in relation to the workpiece carriers.

It can be provided that workpiece carriers are only contained within and/or between one or more clean room sub-regions of the same and/or fundamentally similar clean room class.

It can be provided that each workpiece carrier has a means for fixing, in particular a means for form-fitting and/or force-fitting and/or magnetic fixing, for a corresponding receipt of reactants and/or tools and/or consumable materials, whereby the reactants and/or the tools and/or the consumable materials are held reliably.

The workpiece carriers can remain within the clean room region permanently, in particular over one or more complete production processes.

The production system can comprise a plurality of types of workpiece carriers which differ from one another with regard to the shape and/or dimensioning of a receiving region of the corresponding workpiece carrier.

One type of workpiece carriers can serve to receive a vessel, for example a culture vessel, for receiving a reactant.

One type of workpiece carriers can serve to receive one or more tool units and/or tool consumables for carrying out a treatment process on a reactant and/or for carrying out a maintenance process within the clean room region.

One type of workpiece carrier can serve to receive consumable materials for feeding same to a reactant and/or to carry out a treatment process on a reactant.

One or more workpiece carriers can each comprise one or more action units for carrying out an action on a reactant and/or on a tool.

One or more action units can be designed as a treatment unit, for example as a tool unit, for carrying out a treatment process on the reactant.

It can be provided that a treatment unit, for example a tool unit, is configured to carry out a rocking and/or tilting and/or shaking and/or a rotational movement, in particular by means of at least one correspondingly assigned actuator unit or actuating unit, so that this type of movement, for example this type of movement combination, can be transmitted to the reactant.

It can be provided that a treatment unit, for example a tool unit or a component of a tool unit, is configured to temperature-control, in particular to heat and/or cool, the workpiece carrier.

One or more action units can be designed as a sensor unit for determining a current value of a parameter of the corresponding workpiece carrier and/or of a reactant arranged thereon and/or of a tool arranged thereon and/or of consumable materials arranged thereon.

A parameter can in particular be one of the following: a temperature, an air humidity, an ambient pressure, a gas mixture composition, a position, for example an angular position, an oscillation, an occupancy, in particular an occupancy state, for example a storage occupancy state, and a positioning, for example a locked positioning or a non-locked positioning and/or a location positioning, of the workpiece carrier and/or of an object received by means of the workpiece carrier.

It should be understood that the preceding list is exemplary and not exhaustive.

Alternatively or additionally, it can be provided that the parameter is a combination of the above-described list elements.

One or more workpiece carriers can comprise a storage device for storing energy and/or one or more consumable materials.

The workpiece carriers can be reusable several times, and in particular the storage device can be electrically rechargeable and/or can be refilled with consumable material.

The workpiece carriers can have at least one interface by means of which the electrical energy and/or the consumable material can be charged or refilled and can be dispensed (again).

The production system can comprise a charging station arranged within the clean room region for charging the storage device and/or a refilling station arranged within the clean room region for filling the storage device.

It can be provided that the refilling station is designed as a stationary refilling station which, in order to be filled, can be supplied with consumable material via the airlock device.

It can be provided that the refilling station is designed as a locally mobile refilling station which, in particular in a state filled with consumable material, can be supplied via the airlock device from the surroundings of the production system into the clean room region and, in particular in a state emptied of consumable material, can be removed from the clean room region through the airlock device.

The refilling station can in particular be arrangeable, for example arranged, on a storage space of the storage device.

The refilling station can, for example, comprise a vessel for a liquid or can be designed as a vessel for a liquid.

The vessel for a liquid of the refilling station can, for example, have a volume between 1 ml and 100 l, preferably between 50 ml and 50 l. The vessel can have an interface for removing and/or for filling the liquid.

One or more workpiece carriers can have one or more coupling devices by means of which a plurality of, in particular two or more, workpiece carriers can be connected to one another.

The storage device can comprise a storage transport device for transporting objects to the storage spaces and/or away from the storage spaces.

The handling device can have a distribution unit via which objects to be transported can be supplied to the storage transport device and/or can be received thereby. Optionally, the distribution unit can be designed as an, or as part of an, airlock transport device, or can be assigned to such a device.

The storage transport device can be a device different from the handling device.

The storage transport device can comprise a rail-guided transport system and/or one or more free-moving transport vehicles.

The storage transport device can comprise one or more rail-guided storage transport units, by means of which one or more storage racks of the storage device are accessible in particular for storage and retrieval processes and for treatment processes and/or maintenance processes.

The storage transport device can comprise one or more storage transport units designed as gantry conveyors.

Additionally or alternatively, it can be provided that the storage transport device comprises one or more storage transport units designed as pick-and-place robots or as cable robots.

It can be provided that one or more storage space areas of the storage device are accessible by means of the one or more gantry conveyors, in particular for storage and retrieval processes and for treatment processes and/or maintenance processes.

The storage transport device, in particular the rail-guided transport system, the one or more free-moving transport vehicles, the one or more rail-guided storage transport units and/or the one or more gantry conveyors, can be induction-controlled and/or magnetically guided, in particular guided permanently magnetically and/or by magnet coils. Additionally or alternatively, a sensor-based guide, in particular a camera-based guide and/or a radar/a LIDAR-based guide, can be provided.

It can be provided that the storage transport device, in particular the rail-guided transport system, the one or more free-moving transport vehicles, the one or more rail-guided storage transport units, and/or the one or more gantry conveyors, can be configured to be able to pass through, for example to pass through at least two clean room sub-regions which have a different clean room class from one another.

The storage transport device, in particular the rail-guided transport system, the one or more free-moving transport vehicles, the one or more rail-guided storage transport units, and/or the one or more gantry conveyors, can be designed at least partially encapsulated, whereby, for example, in the case of encapsulated actuators of the storage transport device, a release of possible contamination substances, in particular due to particle abrasion of the actuator, can be avoided or at least reduced.

Additionally or alternatively, it can be provided that the storage transport device comprises one or more elevator devices, by means of which one or more storage space areas of the storage device are accessible in particular for storage and retrieval processes and for treatment processes and/or maintenance processes.

The handling device can be a multi-axis robot arm or can comprise such.

Additionally or alternatively, it can be provided that the handling device is a pick-and-place robot or a cable robot or comprises such a robot, and/or that the handling device is a suitable gripper actuator, or comprises such a gripper actuator, configured on a planar rotor.

Additionally or alternatively, it can be provided that the rail-guided transport system and/or the one or more free-moving transport vehicles of the storage transport device each comprise at least one multi-axis robot arm.

The storage transport device and/or the handling device can be associated with a changing device of the production system by means of which different gripping units and/or carrier units can be mounted on one or more storage transport units of the storage transport device and/or on one or more handling units of the handling device, in particular for carrying out different storage processes, transporting processes, handling processes, maintenance processes and/or treatment processes by means of the corresponding storage transport unit and/or handling unit.

The changing device can have at least one adapter device and/or at least one die device, which are each designed to correspond to the gripping units and/or carrier units in order to be able to engage them in particular in a form-fitting manner and in order to be able to assemble them on the one or more storage transport units of the storage transport device and/or on the one or more handling units of the handling device.

The storage transport device and/or the handling device can be associated with a cleaning device of the production system by means of which at least one gripping unit and/or carrier unit of one or more storage transport units of the storage transport device and/or one or more handling units of the handling device can be cleaned, in particular after carrying out a storage process, transport process, handling process, maintenance process and/or treatment process.

It can be provided that the cleaning device is set up for cleaning, in particular using irradiation and/or gassing.

The cleaning device of the production system associated with the storage transport device and/or the handling device can be arranged in particular in or on the airlock device or, for example, directly adjacent to the airlock device within the clean room region.

It can be provided that the cleaning device of the production system associated with the storage transport device and/or the handling device is spatially separated from the airlock device within the clean room region.

By means of the handling device, one or more objects, for example as described above, can be transferred from an airlock space of the airlock device to a storage transport device, in particular to one or more storage transport units of a storage transport device.

The airlock device can comprise an inlet airlock via which an airlock space, in particular an inlet airlock space, is accessible from the surroundings and which is configured to supply an object from the surroundings of the production system into the clean room region, and an outlet airlock via which an airlock space, in particular an outlet airlock space, is accessible from the surroundings and which is configured to remove an object from the clean room region.

The handling device can comprise an airlock transport device by means of which one or more objects can be transported from an airlock space, in particular an inlet airlock space, to a further airlock space, in particular a transfer airlock space, and/or from an airlock space, in particular a transfer airlock space, to a further airlock space, in particular an outlet airlock space.

It can be provided that the handling device, in particular the airlock transport device, comprises a displacement unit by means of which one or more objects can be moved between the different airlock spaces.

Additionally or alternatively to at least one airlock space, in particular the inlet airlock space and/or the outlet airlock space, an unpacking space and/or a packaging space can be provided in the airlock device.

The unpacking space, adjacently or spatially separated, can be assigned to the inlet airlock space. Additionally or alternatively, the inlet airlock space can be the unpacking space.

The packaging space, adjacently or spatially separated, can be assigned to the outlet airlock space. Additionally or alternatively, the starting airlock space can be the packaging space.

The storage transport device and/or the handling device can each comprise one or more workpiece carrier receptacles for receiving and transporting one or more workpiece carriers, in particular one or more of the workpiece carriers described above.

It can be provided that, by means of the handling device, one or more workpiece carriers, in particular one or more equipped workpiece carriers (for example equipped with a reactant), can be transferred from an airlock space of the airlock device to the storage transport device, in particular to the one or more storage transport units of the storage transport device, in particular via the one or more workpiece carrier receptacles.

In other words, one or more workpiece carrier changes can be carried out, for example are carried out, by means of the handling device.

The airlock device can comprise a cleaning device for cleaning one or more workpiece carriers and/or for cleaning one or more workpiece carrier receptacles.

The production system can comprise a cleaning device which can be supplied to workpiece carriers for cleaning same, in particular after the transport of an object by means of the corresponding workpiece carrier.

It can be provided that the cleaning device associated with the storage transport device and/or the handling device, the cleaning device of the airlock device, and the cleaning device of the production system form a common cleaning device of the production system.

It can be provided that each of the corresponding cleaning devices are designed to be at least partially or completely separate from one another, in particular form independent devices.

The storage device can comprise one or more storage racks and/or one or more storage space areas which each have a plurality of storage spaces.

The respective storage spaces can have different clean room classes. In this context, reference is additionally made to the corresponding part of the description relating to the clean room classes.

The respective storage spaces can serve as decoupling regions and/or areas from regions and/or areas which serve to carry out treatment processes.

It can be provided that the storage spaces can be temperature-controlled, in particular individually temperature-controlled, by means of a, in particular associated, temperature control device of the storage device.

The storage spaces can each be thermally decoupled and/or capable of being decoupled from one another by means of thermal insulation, whereby the storage spaces can be temperature-controlled independently of one another and/or differently from one another, for example can be heated or cooled, by means of a respectively associated temperature-control device.

It can be conceivable that a thermal decoupling of at least two storage spaces takes place by means of a further storage space, for example a storage position of a tool which in particular is not to be temperature-controlled and which is arranged between the at least two storage spaces.

It can be provided that a plurality of storage space areas, in particular two or more storage space areas, are arranged one above the other in particular in a height direction.

To a certain extent, the plurality of storage space areas can be arranged in a stack-like manner.

It can be provided that a plurality of storage space areas, in particular two or more storage space areas, for example two or more storage space areas arranged one above the other, can be or are connected to one another via the storage transport device, in particular via one or more elevator devices of the storage transport device.

By means of the storage transport device, reactants and/or tools and/or consumable materials can be stored in the storage spaces or can be removed therefrom.

In particular, reactants and/or workpiece carriers and/or tools and/or consumable materials can be stored in and/or removed from the storage spaces by means of the storage transport device of the storage device.

One or more storage spaces can be accessible from a plurality of directions and/or by means of a plurality of storage transport units of the storage transport device.

For example, a storage rack can be arranged between, for example, two storage transport units, so that accessibility can be ensured from each storage transport unit onto the intermediate storage rack, or so that each of the, for example two, storage transport units has an access to the storage rack located therebetween.

It may be conceivable for a further storage rack to be arranged in each case on the other side of the, for example, two storage transport units.

To a certain extent, a storage rack-storage transport unit-storage rack-storage transport unit-storage rack arrangement can be present.

It is conceivable that in the intermediate or central storage rack, in particular tools and/or consumable material can be stored, and reactants can be stored in the respective outer storage racks.

By such an exemplary arrangement, for example, short paths of, in particular, tools and/or consumable material to the reactants can be made possible.

A comparable advantage with respect to short paths or path optimization can be achieved in addition to such an alternating arrangement of the storage racks, for example by a star arrangement of storage racks, which in the present case can be provided additionally or alternatively.

The storage spaces can be accessible laterally from above or in the horizontal direction by means of the storage transport device in the vertical direction.

A plurality of substantially horizontally aligned rows of storage spaces can be arranged superimposed in the vertical direction.

To a certain extent, the storage spaces can be arranged in a matrix-like manner.

A plurality of the storage spaces, in particular all storage spaces, can be rack spaces of one or more storage racks.

The storage device can comprise a plurality of different types of storage spaces for receiving different types of workpiece carriers.

The various types of storage spaces can differ from one another with regard to their shape and/or dimensioning.

The various types of storage spaces can differ from one another with regard to their function and/or equipment.

The different types of storage spaces can be arranged in a regular pattern distributed in a storage space rack and/or a storage space area of the storage device.

As a result, for example, rapid access can be ensured to tools or tool units which are required for a treatment process of a reactant.

It can be provided that the various types of storage spaces are arranged according to an optimized, in particular a minimum, path with respect to the objects that are to be stored or are already stored in the storage spaces in a storage space rack and/or a storage space area of the storage device.

As a result, for example, rapid access can be ensured to tools which are required for a treatment process of a reactant.

The storage device can have a plurality of regions for receiving different types of workpiece carriers.

The storage device can comprise a plurality of storage spaces which form treatment stations for treating reactants.

The storage device can comprise a plurality of storage spaces which form tool stations for storage, maintenance, cleaning, changing, electrical charging and/or for control of tools.

The storage device can comprise a plurality of storage spaces which have one or more interfaces, in particular for an (electrical) power supply and/or for a signal transmission, for example an open-loop and/or closed-loop control signal transmission, which can be connected to one or more corresponding interfaces of objects which can be received in the storage spaces, in particular workpiece carriers, for example receiving boxes.

The workpiece carriers already described can in particular be designed as receiving boxes for receiving reactants.

Additionally or alternatively, it can be provided that the production system comprises a plurality of receiving boxes for receiving one or more workpiece carriers together with the reactants arranged and/or received thereon.

As a result, the production system can comprise a plurality of workpiece carriers designed as receiving boxes for receiving reactants or a plurality of receiving boxes for receiving one or more workpiece carriers together with the reactants arranged and/or received thereon.

A receiving box can define a process cell, in particular an aseptic process cell, or a process unit, in particular an aseptic process unit.

To a certain extent, the receiving box can be a process cell, in particular an aseptic process cell, or a process unit, in particular an aseptic process unit.

It can be provided that one or more clean room sub-regions with clean room class A are set up in relation to the receiving boxes or a corresponding receiving box.

It can be provided that a primary function of a receiving box is the provision of an air-conditioned pharmaceutical process space or of a climate-controlled pharmaceutical process environment, in particular with compliance with the highest clean room requirements, in particular with compliance with clean room class A.

A receiving box can in particular be configured for incubation, wherein the receiving box in particular has interfaces for one or more tool units, in particular for gassing and/or temperature control.

The receiving box can be designed and configured to have a hygienic design, in particular to fulfill criteria of a hygienic design, for example with regard to a minimized number of undercuts, whereby a cleaning capability of the receiving box is optimized.

For hygienic design of a receiving box, this can, in particular, be equipped with a means for magnetic fixing, whereby in particular the reactants can be reliably held under optimized hygienic conditions, wherein, for example, the means for magnetic fixing can be configured to interact with an at least partially magnetic counter element of a vessel for receiving a reactant or a reactant container.

Additionally or alternatively, it can be provided for this purpose that a receiving box is equipped with a means for form-fitting and/or force-fitting fixing.

The receiving boxes can be mounted in storage spaces of the storage device, in particular fully automatically by means of a storage transport device of the storage device that has already been described, for example.

One or more of the receiving boxes can surround a closable interior.

A clean room sub-region and/or an aseptic production region can be definable by the closable interior.

To a certain extent, it can be provided that the closable interior is a clean room sub-region and/or an aseptic production region.

The clean room sub-region definable by the closable interior can have a clean room class A.

The receiving boxes can be opened and/or closed automatically and/or by means of the handling device for introducing a reactant and/or for removing a product produced from a reactant.

One or more of the receiving boxes can each comprise one or more conditioning units which can be integrated or detachably arranged thereon or detachably arrangeable thereon, by means of which conditioning units a temperature and/or a pressure and/or a moisture and/or a gas composition in the interior of the corresponding receiving box can be influenced, in particular can be subjected to open-loop and/or closed-loop control.

One or more of the conditioning units can be tool units of a tool system of the production system, which can be arranged on the corresponding receiving box if necessary or can be removed therefrom, in particular fully automatically by means of a storage transport device, for example the already described storage transport device of the storage device and/or by means of the handling device.

Additionally or alternatively, it can be provided that one or more of the conditioning units are tool units of a tool system of the production system, which can be arranged on the corresponding receiving box if necessary or can be removed therefrom, in particular independently by means of its own actuator system and/or using an actuator system set up in or at the corresponding receiving box.

The receiving boxes can comprise one or more connection elements which can be connected to connection elements corresponding thereto at one or more treatment stations, in particular in order to supply the corresponding receiving box with electrical energy and/or consumable substances, in particular liquids and/or gases, and/or to establish a signal-related coupling of the corresponding receiving box to an in particular superordinate control device, for example one or more control units.

The storage device can comprise storage spaces provided with connection elements, so that one or more treatment processes can be carried out for the treatment of the reactants at storage spaces of the storage device serving as treatment stations.

The storage spaces of the storage device and/or the receiving boxes can comprise fixing elements by means of which the receiving boxes can be positioned and/or fixed at the storage spaces.

The receiving boxes can each comprise one or more tool holders for receiving and fixing one or more tools, in particular in the interior of the corresponding receiving box.

The one or more tool holders can each comprise one or more connection elements which can be connected to connection elements corresponding thereto on the tool to be received in each case, in particular in order to supply the corresponding tool with electrical energy and/or consumable substances, in particular liquids and/or gases, and/or in order to produce a signal-related coupling of the corresponding tool to the receiving box and/or to an in particular superordinate control device.

In a state not used for product production, the receiving boxes can also be storable at storage spaces (in each case), in particular after cleaning by means of a cleaning device of the production system that is already described, for example.

The receiving boxes stored in storage spaces in a state not used for product production can be removable from the storage spaces for receiving or introducing reactants, in particular fully automatically by means of the storage transport device of the storage device.

Additionally or alternatively, it can be provided that a receiving box comprises one or more connection elements which can be connected to connection elements corresponding thereto on a further receiving box, whereby an assembled receiving box can be provided.

For a possible embodiment and/or configuration of the assembled receiving box, reference is made to the description of the receiving box(es).

It can be provided that one or more storage spaces are configured as storage spaces for assembled receiving boxes.

Additionally or alternatively, it can be provided that one or more, in particular all, receiving boxes are configured to receive one or more workpiece carriers together with tools arranged and/or received thereon and/or consumable material arranged and/or received thereon. Additionally or alternatively, it can be provided that a workpiece carrier is designed as a tool carrier and/or as a consumable material carrier.

The production system can comprise an unpacking device for unpacking objects to be supplied to the clean room region.

The unpacking device can be integrated into the airlock device or can form a component thereof.

Additionally or alternatively, it can be provided that the unpacking device of the handling device and/or the storage device is integrated, in particular via an autoclave device, for example a through-autoclave device, by means of which unpacked and/or partially unpacked objects can be received, then sterilized and dried, and then the handling device and/or the storage device can be supplied, in particular in an automated manner.

The airlock device can comprise an inlet airlock space which is accessible from the surroundings of the production system and on which a packaged object can be arranged in particular by a person and/or automatically.

The packaged object can be transported by means of an airlock transport device of the production system from the inlet airlock space to an unpacking space, for example the already described unpacking space, and can be unpacked at the unpacking space in an automated manner, or the packaged object can be unpacked in an automated manner at the inlet airlock space.

The airlock device can comprise a cleaning device, for example the cleaning device already described, for cleaning a packaging of the packaged object.

It can be provided that the object can be cleaned and/or sterilized in a packaged state by means of the cleaning device of the airlock device, in particular by means of irradiation and/or gassing.

The cleaning by means of the cleaning device of the airlock device can in particular be carried out at the inlet airlock space, the unpacking space and/or a cleaning station provided in the airlock device.

The unpacking device can comprise a plurality of unpacking units for unpacking different types of objects and/or packaging, in particular for removing different types of packaging from the objects.

One or more unpacking units for unpacking reactants and one or more further unpacking units for unpacking tools and/or consumable materials can be formed.

The packaging of the packaged object, in particular of the packaged reactant, can be discharged in a sterile manner by means of one or more unpacking units after unpacking, for example via the outlet airlock space and/or via a waste airlock space of a separately designed waste airlock of the unpacking device or the airlock device, whereby the unpacked object, in particular the unpacked reactant, cannot come into contact with the packaging.

The object, in particular the reactant, after unpacking, can be supplied to the handling device, in particular by means of the airlock transport device.

It can be provided that the unpacking space in the airlock device is set up spatially separately from the rest of the airlock device.

The unpacking can be carried out fully automatically by means of one or more unpacking units.

Additionally or alternatively, it can be provided that the unpacking can be carried out manually and/or partially automatically, for example automatically using at least one manual action.

It can be provided that the airlock device, in particular one of the airlock spaces provided in the airlock device, for example the unpacking space, can be cleaned before, during and/or after unpacking by means of the cleaning device of the airlock device, in particular by means of irradiation and/or gassing.

Cleaning during unpacking can be carried out, for example, between individual unpacking steps.

The unpacking device can comprise a detection device and a control device, by means of which a type of the object to be unpacked and/or a type of the packaging to be removed can be determined.

By means of the control device, an unpacking unit of the unpacking device can be selectable and actuatable for carrying out the unpacking process, wherein the unpacking unit can be one of a plurality of unpacking units for carrying out different unpacking processes, wherein the selected unpacking unit can be associated with the determined type of object to be unpacked and/or the type of packaging to be removed.

Additionally or alternatively, it can be provided that unpacking can be carried out manually, for example, at the inlet airlock space.

The production system can comprise a packaging device for packaging the objects to be removed from the clean room region, for example the product produced.

The packaging device can be integrated into the airlock device or form a component thereof.

Additionally or alternatively, it can be provided that the packaging device of the handling device and/or the storage device is integrated, in particular via an autoclave device, for example a through-autoclave device, by means of which objects can be received, then sterilized and dried, and subsequently discharged, in particular in an automated manner.

The airlock device can comprise an outlet airlock space which is accessible from the surroundings of the production system and on which a packaged object can be removed in particular by a person and/or automatically.

The object to be packaged can be transported from a transfer airlock space to a packaging space by means of an airlock transport device of the production system and can be packaged in an automated manner at the packaging space, or the object to be packaged can be automatically packageable at the outlet airlock space.

The packaging device can comprise a plurality of packaging units for packaging different types of objects and/or packaging, in particular for packaging the objects with different types of packaging.

One or more packaging units can be designed for packaging produced products and one or more further unpacking units can be designed for packaging used tools to be removed and/or used consumable materials to be removed.

The object to be packaged, in particular the produced product, can be movable, in particular manageable or transportable, before, during and/or after packaging by means of the handling device and/or the airlock transport device.

It can be provided that the packaging space in the airlock device is arranged spatially separated from the rest of the airlock device.

The packaging can be carried out fully automatically by means of one or more packaging units.

Additionally or alternatively, it can be provided that the packaging can be carried out manually and/or partially automatically, for example automatically using at least one manual action.

It can be provided that the airlock device, in particular one of the airlock spaces provided in the airlock device, for example the packaging space, can be cleaned before, during and/or after a packaging by means of the cleaning device of the airlock device, in particular by means of irradiation and/or gassing.

The packaging device can comprise a detection device and a control device, by means of which a type of the object to be packaged and/or a type of the packaging to be used can be determined.

By means of the control device, a packaging unit of the packaging device can be selectable and actuatable for carrying out the packaging process, wherein the packaging unit can be one of a plurality of packaging units for carrying out different packaging processes, wherein the selected packaging unit can be assigned to the determined type of object to be packaged and/or the type of packaging used.

It can be provided that the packaging device and the unpacking device are designed in a common device for unpacking and/or packaging.

As already described in conjunction with the conditioning units of the receiving boxes, the production system can comprise a tool system.

In particular, the production system can comprise a tool system by means of which treatment processes can be carried out at reactants and/or maintenance processes can be carried out within the clean room region.

The tool system can comprise a plurality of in particular fully automatic tool units for carrying out different treatment and/or maintenance processes.

It can be provided that a tool unit described herein is a tool described herein and/or a tool described herein is a tool unit described herein.

The tool system can comprise one or more tool units designed as supply units for supplying consumable materials to the reactants.

It can be provided that consumable materials comprise at least one liquid and/or at least one gas and/or gas mixture.

Additionally or alternatively, it can be provided that consumable materials comprise at least one solid, for example at least one lyophilized solid.

The tool system can comprise one or more tool units designed as removal units for removing a sample from a reactant.

One or more of the tool units of the tool system can in each case comprise one or more multi-use components and/or one or more single-use components.

The tool system can comprise a set-up unit by means of which one or more single-use components of a tool unit can be removed, in particular can be disposed of, after use thereof, and can be replaced by one or more new single-use components.

A single-use component can in particular be a component which, after its single use, in particular for the first time, can no longer be used again.

A multi-use component can in particular be a component which can be used at least one further time after its single, in particular first, use.

A single-use component and/or a multi-use component can each be, for example, an element and/or a system.

Optionally, such an element and/or such a system can comprise at least one of the following: a tube, a needle, a syringe, a container, in particular a vessel or a bag, for example a vessel for a reactant, a valve, a microfluidics unit, a probe, a cartridge, a vial, and/or a small bottle, in particular for reagents.

It should be understood that the preceding list is exemplary and not exhaustive.

Alternatively or additionally, it can be provided that the element has a combination of the above-described list elements.

A multi-use component can be cleanable and/or sterilizable.

The set-up unit can be arranged completely within the clean room region.

The set-up unit can comprise a handling unit, in particular a multi-axis robot arm, by means of which a fully automatic set-up process can be carried out.

It can be provided that the set-up process, in particular a removal process and/or an equipping process of the set-up process, can be carried out in one or more, in particular different, clean room sub-regions of the clean room region.

The set-up unit can comprise a cleaning unit or a cleaning unit can be associated with the set-up unit, by means of which cleaning unit multi-use components of one or more tool units can be cleaned, in particular sterilized, after use.

Additionally or alternatively, it can be provided that the cleaning unit is designed as a tool unit independently or separately.

It can be provided that cleaning can be carried out before, during, in particular between the removal process and the equipping process, and/or after the set-up process by means of the cleaning unit.

The tool system can comprise a plurality of portable tool units which, in order to carry out a treatment process, can be supplied to a treatment station for treating a reactant which, in particular, is at the same time a storage space for storing the reactant, and can be temporarily stored there.

One or more portable tool units of the tool system can be supplied to a tool storage space and/or to a treatment station and/or to a set-up station by means of a storage transport device, in particular one or more storage transport units, of the production system.

One or more tool units can be designed and set up by means of the handling device for carrying out a treatment process and/or a maintenance process.

One or more tool units can be designed and set up independently of the handling device, in particular automatically, for carrying out a treatment process and/or a maintenance process.

It can be provided that a tool unit can be used once only or can be re-used.

A tool unit can be placed in a storage space, stored temporarily, stored, and/or can be connected to associated interfaces in the storage space.

A tool unit can be a mechanical tool.

A tool unit can be able to be used in a movable and/or determined manner by means of a robot arm, for example a multi-axis robot arm.

A tool unit can be a tool for feeding and/or discharging, for example, a liquid, in particular a tool for pumping a liquid, for example a pump tool, wherein the tool unit can in particular be configured to supply and/or discharge a predetermined quantity of liquid, in particular for sampling for analysis.

A tool unit can be a tool for mixing at least one liquid, in particular at least one liquid with at least one liquid, gaseous and/or solid substance. For example, the tool unit can be a pump for circulating.

A tool unit can be a means for biochemical manipulation of cells by means of which at least one substance can be supplied to a reactant, and/or a temperature of a reactant can be changed, and/or an ambient pressure of a reactant can be changed, wherein the reactant is arranged, in particular accommodated, in particular in a tool carrier, in particular in a receiving box. In particular, the surroundings of the reactant, in particular of the cells of the reactant, can thus be variable in order thereby to change the reactant itself, in particular the cells of the reactant itself, in particular with regard to cell growth and/or a cell surface, for example a cell membrane surface, and/or a cell metabolism.

A tool unit can be a means for concentrating and/or separating liquids, in particular by means of a column, for example a separation column, and/or a centrifuge.

Additionally or alternatively, it can be provided that at least one auxiliary, for example magnetic particles, is used for concentrating and/or separating liquids.

A tool unit can be a means for analyzing process parameters by means of a probe and/or a sensor, wherein the probe and/or the sensor is configured, for example, to capture, detect and/or determine at least one of the following: at least one temperature, at least one particle, for example at least one particle concentration, at least one oscillation, at least one acceleration, at least one cell number, at least one cell density, at least one turbidity, for example at least one light absorption due to a liquid turbidity, at least one gas composition, at least one gas, for example $CO_2$, and/or at least one chemical substance, in particular at least one biochemical substance, for example at least one metabolite.

It should be understood that the preceding list is exemplary and not exhaustive.

It can be provided that the tool system comprises a recycling and/or reprocessing unit by means of which cleaning and/or reprocessing processes can be carried out in the clean room region, in particular at least one of the following:

the clean room region itself, for example a clean room sub-region of the clean room region itself, in order to maintain its clean room properties, for example its clean room class properties, the storage transport device, in particular a storage transport unit of the storage transport device, in order to maintain the clean room properties, for example the clean room class properties, of the clean room region, for example of the clean room sub-region in which the storage transport device or its storage transport unit is arranged and/or movable, consumable material, a tool or a tool unit, a workpiece carrier.

It should be understood that the preceding list is exemplary and not exhaustive.

The recycling and/or reprocessing unit can have a sensor system by means of which a success, in particular a quality, of a cleaning and/or reprocessing process can be determined.

It can be provided that the purified and/or reprocessed, for example at least one of the above-described list elements, can be prepared for a subsequent process after a cleaning and/or reprocessing process, in particular in or at a storage space, by means of the recycling and/or reprocessing unit.

It can be provided that a defective and/or the excess tool unit can be removed from the production system via the airlock device, in particular the defective and/or the excess tool unit can be storable from a storage space and can be transported automatically to the airlock device for the removal of same from the production system.

It can be provided that the tool system is set up in particular fully automatically.

In some cases, the production system can comprise an in particular fully automatic tool system which comprises one or more tool units for carrying out treatment processes on a reactant, wherein the tool system is arranged within the clean room region, for example within a clean room sub-region, for example within a receiving box as a clean room sub-region.

The tool system can comprise one or more tool units designed as a fluid conveying device, by means of which a fluid can be conveyed in particular adjustably with respect to a volume flow.

A volume flow that can be conveyed by means of the fluid conveying device can, for example, be equal to or greater than 500 ml/min. A tolerance of +5% can be provided.

The fluid conveying device can have a directional element by means of which a directed volume flow can be generated.

The fluid conveying device can have a thermal insulation by means of which a temperature of a fluid can be kept constant during conveying.

Additionally or alternatively, the fluid conveying device can have a heating source and/or a cooling unit and/or a heating source and/or a cooling unit can be associated with the fluid conveying device, by means of which heating source and/or cooling unit a temperature of a fluid can be kept constant and/or can be adjusted during conveying.

The fluid conveying device can have at least one sensor system in order to be able to monitor and/or provide open-loop and/or closed-loop control of fluid conveyance, and/or in order to be able to analyze and/or detect components, for example particles and/or a turbidity and/or air bubbles and/or fluorescently labeled components, in the conveyed fluid.

The fluid conveying device can have a fluid guide arrangement by means of which the fluid can be conveyed substantially without a foam.

The fluid conveying device can be optimized in respect of dead volume.

The tool system can comprise one or more tool units designed as a micro-fluid conveying device, by means of which a fluid can be conveyed in particular to be adjustable with respect to a volume flow, in particular for aliquoting.

A volume flow that can be conveyed by means of the micro-fluid delivery device can, for example, be less than 500 ml/min, preferably greater than or equal to 100 μl/min and less than 500 ml/min. A tolerance of ±5% can be provided in each case.

The micro-fluid conveying device can have a directional element by means of which a directed volume flow can be generated.

The micro-fluid conveying device can have a thermal insulation by means of which a temperature of a fluid can be kept constant during conveying.

Additionally or alternatively, the micro-fluid conveying device can have a heating source and/or a cooling unit and/or a heating source and/or a cooling unit can be associated with the micro-fluid conveying device, by means of which heating source and/or cooling unit a temperature of a fluid can be kept constant and/or can be adjusted during conveying.

The micro-fluid conveying device can have at least one sensor system in order to be able to monitor and/or provide open-loop and/or closed-loop control of fluid conveyance, and/or in order to be able to analyze and/or detect components, for example particles and/or a turbidity and/or air bubbles and/or fluorescently labeled components, in the conveyed fluid.

The micro-fluid conveying device can have a micro-fluid guide arrangement by means of which the fluid can be conveyed substantially without a foam.

The micro-fluid conveying device can be optimized in respect of dead volume.

The tool system can comprise one or more tool units designed as a device for dividing a fluid, by means of which tool units the fluid can be conveyed in particular adjustably with respect to a volume flow and by means of which the fluid can be divided in particular adjustably into at least two, in particular two to twelve, fluid parts.

The fluid parts, in particular their associated volume flows, can, for example, be less than 500 ml/min, preferably greater than or equal to 100 μl/min and less than 500 ml/min. A tolerance of ±5% can be provided in each case.

It can be provided that the divided fluid, in particular at least one fluid portion of the divided fluid, can be dispensed into at least one associated container, in particular a vessel, workpiece carrier and/or receiving box, and/or in and/or on a sensor by means of the device for dividing a fluid.

The device for dividing a fluid can have a directional element by means of which at least one directed volume flow, in particular at least two directed volume flows, can be produced.

The device for dividing a fluid can have a thermal insulation by means of which a temperature of a fluid during conveying and/or during division can be kept constant.

Additionally or alternatively, the device for dividing a fluid can have a heating source and/or a cooling unit and/or the device for dividing a fluid can be associated with a heating source and/or a cooling unit, by means of which a temperature of a fluid can be kept constant and/or can be adjusted during conveying and/or during division.

The device for dividing a fluid can have a fluid guide arrangement for the fluid to be dispensed and/or for the divided fluid, in particular for the corresponding fluid parts, by means of which the fluid and/or the fluid parts can be conveyed and/or divided substantially without a foam.

The device for dividing a fluid can be optimized in respect of dead volume.

The tool system can comprise one or more tool units designed as a fluid mixing device, by means of which a fluid can be mixed.

The fluid mixing device can have a mixing unit, in particular a mechanical mixing unit and/or a geometric mixing unit, which has a defined fluid-conducting arrangement for mixing, in particular for substantially foam-free mixing.

It can be provided that the fluid can be mixed with a defined shear force, in particular with little gravity, in particular in a substantially foam-free manner, by means of the mixing unit of the fluid mixing device.

Additionally or alternatively, the fluid mixing device can have a heating source and/or a cooling unit and/or a heating source and/or a cooling unit can be associated with the fluid mixing device, by means of which heating source and/or cooling unit a temperature of a fluid can be kept constant and/or can be adjusted during mixing.

The tool system can comprise one or more tool units designed as a mixing device, by means of which at least two components are miscible with one another, wherein in particular one of the at least two components is a fluid.

The mixing device can be configured substantially similarly to the fluid mixing device, in particular the mixing device can be configured similarly to the fluid mixing device or can be designed as the fluid mixing device. As a result, the fluid mixing device can also be designed as the mixing device.

The tool system can comprise one or more tool units designed as a measuring device, by means of which at least one property of a fluid and/or of one reactant can be measured.

It can be provided that the measuring device is configured to measure a pH, and/or a gas value or a gas mixture value, for example an oxygen value, a cell density, and/or a turbidity, in particular a turbidity in a fluid.

The tool system can comprise one or more tool units designed as a material separation device, by means of which a starting component can be separated into at least two components.

It can be provided that the material separation device has means for tangential flow filtration, for centrifugation, for example with 200 to 300 g, for affinity chromatography, and/or for magnetic separation by means of which the starting component can be separated into at least two components.

Additionally or alternatively, the material separation device can have a temperature control element and/or the material separation device can be assigned a temperature control element by means of which a temperature of a starting component to be separated and/or the separated starting component can be kept and/or set constantly before, during and/or after the separation, for example to a temperature of from 5 to 10° C.

The tool system can comprise one or more tool units designed as a heating device, by means of which a fluid can be temperature-controlled, in particular heated and/or cooled, for example to a temperature of less than or equal to 37° C.

The heating device can be designed as a separate device.

It can be provided that the heating source and/or the temperature control element are designed as part of the heating device and/or are associated with the above-described devices of the tool system.

The heating device can be arranged and/or configured to form a homogeneous temperature field in particular in spatial and/or temporal terms.

The tool system can comprise one or more tool units designed as a device for supplying and/or discharging a gas, in particular a gas mixture, by means of which a gas, in particular a gas mixture, can in particular be supplied and/or discharged homogeneously.

By means of the device for supplying and/or discharging a gas, oxygen, carbon dioxide and/or hydrogen peroxide, for example, can be supplied and/or discharged.

It can be provided that the fluid conveying device, the micro-fluid conveying device, the device for dividing a fluid, the fluid mixing device, the mixing device, the measuring device, the material separation device, the heating device, and the device for supplying and/or discharging a gas in any combination with one another are designed as one or more devices, for example in a single common device.

The tool system can comprise one or more tool units designed as a manipulator, by means of which a cell membrane, in particular a cell membrane of a cell of a reactant, can be manipulated, in particular by means of at least one of the following or any combination thereof: (by means of) an electrical field, an addition of a chemical, a receptor-mediated transfection, a microinjection, a gene gun, a magnet assisted transfection, a sonoporation, an optical transfection, a microfluid channel, for example squeezing into a micro-fluid channel.

Additionally or alternatively, it can be provided that genetic material, in particular a cell-foreign genetic material, for example a DNA, for example a foreign DNA, and/or an RNA, for example a foreign RNA, can be introduced into the cell through the cell membrane by means of the manipulator.

Additionally or alternatively, it can be provided that viruses can be supplied to the cell by means of the manipulator, which viruses can carry out the actual manipulation of the cell.

The tool system can comprise one or more tool units designed as a radiation source and/or a light emitting device, wherein the radiation source is configured to emit an ionized radiation, in particular to a target object, for example to a reactant, and the light emitting device is configured to emit light having a predetermined wave length, in particular to a target object, for example to a reactant.

Additionally or alternatively, it can be provided that the tool system comprises one or more tool units designed as a flow cell sequencing device and/or as a next generation sequencing device.

The tool system can comprise one or more tool units designed as a cleaning device, in particular as the cleaning device already described and/or as the cleaning unit already described, by means of which a location at which the treatment processes can be carried out at the reactant by means of the one or more tool units can be cleaned and/or sterilized.

It can be provided that a supply device for supplying the tool system with consumable materials is associated with the tool system.

To a certain extent, the production system can comprise, for example, the above-described tool system and a supply device for supplying the tool system with consumable materials.

The supply device can comprise or use one or more storage spaces of the storage device arranged within the clean room region for storing consumable materials.

To a certain extent, storage spaces of the storage device can be associated with the supply device.

The airlock device can form a component of the supply device or can interact therewith, wherein consumable materials can be introduced into the clean room region by means of the airlock device.

The consumable materials to be used during a treatment process can be providable, in particular before they are used, in the airlock device, in particular on an outlet airlock space of the airlock device, and can, optionally, be prepared for use, in particular unpacked and/or temperature-controlled.

The storage device can form a component of the supply device or can interact therewith.

By means of a storage transport device of the storage device, in particular by means of one or more storage transport units of the storage transport device of the storage device, consumable materials supplied from the surroundings of the production system, in particular supplied by the airlock device, can be supplied to one or more storage spaces of the storage device.

By means of a storage transport device of the storage device, in particular by means of one or more storage transport units of the storage transport device of the storage device, consumable materials can be supplied to the tool system, in particular one or more tool units of the tool system, for example for supplying consumable substances and/or tool consumables to one or more tool units of the tool system.

It can be provided that the consumable substances and/or the tool consumables comprise one or more multi-use components and/or one or more single-use components.

The consumable materials to be used during a treatment process can be providable in the storage spaces, in particular before they are used, and can optionally be prepared, in particular temperature-controlled, for use.

The supply device can comprise one or more disposal units, by means of which, in particular, used, spent and/or contaminated consumable substances and/or tool consumables can be removed from the clean room region.

One or more disposal units can be associated with the set-up unit of the tool system, in particular can be handled by it, and/or can form a component of the set-up unit of the tool system.

The supply device can comprise a refilling device arranged within the clean room region, by means of which consumable substances in particular present in liquid form can be supplied to one or more storage devices of one or more workpiece carriers and/or one or more storage spaces.

Additionally or alternatively, the refilling device can be designed as the above-described refilling station and/or can be associated therewith.

The storage device may in particular be configured to store energy and/or one or more consumable materials, in particular the storage device can be electrically recharged and/or refillable with consumable material.

Energy and/or one or more consumable materials for carrying out a treatment cycle can be provided by means of the storage device.

The storage device may comprise at least one interface for refilling and/or providing the energy and/or consumable materials, in particular the interface can be configured to be coupleable to a tool/a tool unit, in particular for said provision.

The supply device can have a water system, in particular an ultrapure water system, for providing water, in particular ultrapure water, as at least one consumable material.

The water system can, for example, be connectable via interfaces provided in the production system to a water source, in particular to an ultrapure water source, wherein it can be provided that the water source is arranged in the surroundings of the production system.

As already described, one or more probes, sensors, sensor units and/or the same measuring elements can be included in the production system.

To a certain extent, the production system can comprise one or more sensor units for determining one or more values of one or more parameters of one or more reactants, and/or one or more workpiece carriers, and/or one or more tools.

It can be provided that the production system comprises one or more sensor units for determining one or more values of one or more parameters of one or more consumable materials.

The determination can be carried out at least partially automatically, in particular fully automatically, by means of one or more sensor units.

By means of one or more sensor units, an occupancy state of one or more storage spaces of a storage device of the production system can be determined, in particular monitored.

By means of one or more sensor units, a local temperature and/or a local humidity and/or a local illumination or irradiance can be determined, in particular monitored, at or in one or more storage spaces of the storage device of the production system.

The production system can comprise one or more sensor units for determining a progress of treatment during the treatment of a reactant or between two treatment processes.

It can be provided that the production system comprises one or more sensor units for determining a progress of treatment during the treatment of a reactant or between two treatment processes on the basis of at least one fluid of the reactant.

For determining the progress of treatment, one or more sensor units can be microscopy devices for visually capturing microscopic components of the reactant.

The microscopy device can comprise an automated microscopy device, and/or a lens-less microscopy device, and/or a light microscopic microscopy device, and/or a microscopy device for fluorescence and/or luminescence examination and/or can be designed as such.

The microscopy device can have a data and/or image processing unit which is designed and programmed to detect and/or determine at least one treatment progress and/or one or more values of one or more parameters of one or more reactants.

By means of the data and/or image processing unit of the microscopy device, a morphology and/or a concentration, and/or a motility, and/or a functionality of corresponding cells of one or more reactants is detectable and/or ascertainable.

For receiving reactants, one or more sensor units for determining the treatment progress can in each case be arranged at or in one or more storage spaces, in particular integrated therein.

The production system, in particular one or more tools for carrying out one or more treatment processes, can be controlled on the basis of open-loop and/or closed-loop control depending on the one or more determined values, wherein one or more treatment parameters can be varied, in particular can be changed, in particular depending on a determined treatment progress.

The production system can comprise one or more sensor units for monitoring a quantity of consumable materials stored within the clean room region.

The production system can comprise one or more communication interfaces and/or one or more human-machine-interface interfaces, for short: HMI interfaces, by means of which information can be provided from the production system to an undershooting of a predetermined quantity of consumable materials, in particular to a user and/or a computer system.

It can be provided that one or more sensor units are designed as a device for polymerase chain reaction analysis (PCR analysis) and/or for endotoxin testing and/or for *mycoplasma* testing.

It can be provided that a protein analysis, in particular a protein determination and/or an enzymatic activity test and/or an immunological test and/or an amino acid analysis and/or a protein sequence analysis, on the reactant and/or a part, in particular a component, of the reactant can be carried out by means of one or more sensor units.

Additionally and/or alternatively, it can be provided that a spectroscopy and/or a light microscopy method and/or a chromatography method and/or an electrophoresis method and/or a mass spectrometry on the reactant and/or a part, in particular a component, of the reactant can be carried out by means of one or more sensor units.

It can be provided that a 3D structure elucidation, in particular magnetic resonance spectroscopy and/or an electron microscopy method and/or a scanning electron microscope method and/or an X-ray analysis, on the reactant and/or a part, in particular a component, of the reactant can be carried out by means of one or more sensor units.

It can be provided that, by means of one or more sensor units, a peptide analysis and/or a carbohydrate analysis, in particular a high-performance liquid chromatography and/or an electrophoresis and/or a mass spectrometry and/or a magnetic resonance spectroscopy, and/or a lipid analysis, in particular a solid phase extraction and/or a chromatography and/or a mass spectrometry and/or an immunoassay test, and/or a phosphorylation and acetylation analysis, in particular with regard to at least one protein, and/or a metabolite test and/or metabolite monitoring, in particular with regard to glucose, lactate, oxygen, carbon dioxide, ammonium, phosphate and/or its derivatives, on the reactant and/or a part, in particular a component, of the reactant can be carried out.

It can be provided that a nucleic acid analysis can be carried out on the reactant and/or a part, in particular a component, of the reactant by means of one or more sensor units.

It can be provided that the production system, in particular for a nucleic acid analysis, comprises an extraction device and/or a gel filtration device and/or a precipitation device and/or a concentration device and/or a centrifugation device and/or an isolation device and/or a PCR analysis device and/or a magnetic bead handling device for separating magnetic beads and coupled material and fluid, which one or more sensors units is/are assignable and/or is/are assigned to one or more sensor units, in particular for a nucleic acid analysis.

It can be provided, for example, that by means of one or more sensor units, in particular for a nucleic acid analysis, an absorption measurement and/or a gel electrophoresis, in particular for separating and/or purifying RNA and/or DNA and/or proteins, and/or a gel documentation, in particular with regard to an RNA and/or a DNA and/or protein gels and/or Western blotting, and/or an RNA analysis and/or a DNA analysis and/or a sequence analysis and/or a chip analysis and/or a protein DNA interaction analysis and/or a genotyping and/or an epigenetic analysis and/or a proteome analysis and/or a metabolic fingerprinting, profiling, or target analysis can be carried out on the reactant and/or a part, in particular a component, of the reactant.

It can be provided that the production system, in particular for a cell analysis, comprises a morphology determination device and/or a metabolite test device and/or a receptor binding test device and/or a signal transduction test device and/or a cell differentiation test device and/or a viscosity test device and/or a DNA/RNA/protein expression test device and/or a chip/microfluidic-based test device, which can be assigned and/or is assigned to one or more sensor units, in particular for a cell analysis.

Additionally or alternatively, it can be provided that an expression analysis, in particular for gene and/or protein expression, and/or a transfection analysis and/or a flow cytometry and/or an ELISA test and/or a luciferase test and/or a kinase test on the reactant and/or a part, in particular a component, of the reactant can be carried out by means of one or more sensor units.

It can be provided that an osmolality test and/or a freezing point reduction measurement and/or a turbidity measurement, in particular a measurement of the optical density, and/or a particle measurement, in particular a particle density measurement, and/or a pH measurement and/or a viscosity measurement on the reactant and/or a part, in particular a component, of the reactant can be carried out by means of one or more sensor units.

In other words, it can be summarized that the production system comprises one or more sensor system units by means of which one or more, substantially all, process steps, in particular one or more, substantially all treatment processes, and/or one or more, substantially all, process states, in particular one or more, substantially all treatment states, and in particular can be closed-loop controlled, in particular readjusted, and/or can be open-loop controlled, in particular can be readjusted, if necessary.

The sensor system units can in particular address: at least one temperature, at least one particle, for example at least one particle concentration, at least one oscillation, at least one acceleration, at least one cell number, at least one cell density, at least one turbidity, in particular a turbidity of a reactant and/or product suspension, for example at least one light absorption due to a liquid turbidity, in particular in a reactant and/or product suspension, at least one gas composition, at least one gas, for example $CO_2$, and/or at least one chemical substance, in particular at least one biochemical substance, for example at least one metabolite, for example glucose.

The above-described sensor units or the above-described sensor system units can be arranged in the production system, depending on requirements, in particular in relation to one or more objects, for example reactants and/or tools and/or storage spaces and/or consumable materials, in the clean room region.

In particular, one or more sensor units or one or more sensor system units can be arranged and/or arrangeable in line in order to enable continuous automated measurement in particular with respect to one or more reactants and/or to enable monitoring in real time.

In particular, additionally or alternatively, one or more sensor units or one or more sensor system units can be arranged and/or arrangeable online, in order to enable a continuous automated measurement in particular with respect to one or more reactants, wherein a positioning of the sensor unit or of the sensor unit takes place not in an especially immediate treatment environment of a reactant, but in a branch, for example a bypass, leading away from a treatment environment designed for this, in which (branch) a sample of the substances to be examined, in particular of the reactant, can be removed in particular automatically, wherein, optionally, an addition of reagents, for example for a color change, can be introduced into the branch.

In particular, in addition or alternatively, one or more sensor units or one or more sensor system units can be arrangeable and/or arranged atline, wherein a sample of the reactant removed from the treatment environment of a reactant can be examined separately, in particular locally separated, from the treatment environment, wherein, optionally, a separate sample preparation can be carried out.

It can be provided that the one or more sensor units arranged atline can be arrangeable and/or arranged adjacent to the treatment environment of a reactant in the clean room region, in particular in the immediate vicinity thereof.

Alternatively or additionally, it can be provided that the one or more sensor units arranged atline can be arrangeable and/or arranged adjacent to the production system in the surroundings of the production system, in particular in the immediate vicinity of the production system.

In particular, additionally or alternatively, one or more sensor units or one or more sensor system units can be arrangeable and/or arranged offline, in particular outside the clean room region and/or the entire production system, for example in an external laboratory.

As already described above, the production system can comprise one or more cleaning devices.

The cleaning device can be designed as a separate device in the clean room region and/or can be a component of the tool system, in particular of a tool or a tool unit, and/or of the airlock device and/or the storage device.

The cleaning device can comprise one or more interfaces, by means of which the cleaning device can be connected to an especially pharmaceutical cleaning system for cleaning in place (CIP), for washing in place (WIP) and/or for sterilization in place (SIP).

Cleaning in place, washing in place, and/or sterilization in place can be feasible in particular in the storage spaces and/or on the workpiece carriers, in particular the receiving boxes.

The cleaning device can comprise one or more interfaces by means of which a gas and/or a gas mixture and/or a liquid of the cleaning device can be supplied, for example gaseous and/or liquid hydrogen peroxide, in order to be able to clean, in particular decontaminate, and/or sterilize one or more objects within the clean room region and/or parts, in particular everything, of the clean room region, in particular of at least one clean room sub-region.

The cleaning device can comprise one or more drying devices, by means of which one or more objects, in particular tools and/or workpiece carriers, for example receiving boxes, within the clean room region and/or parts, in particular all, of the clean room region, in particular of at least one clean room sub-region, can be dried, in particular after cleaning has taken place.

Additionally or alternatively, the cleaning device can comprise one or more autoclave devices by means of which one or more objects within the clean room region can be sterilized.

It can be provided that the one or more autoclave devices are realized as an autoclave device described in conjunction with the unpacking device and/or with the packaging device.

The cleaning device can comprise one or more interfaces, by means of which wastewaters, in particular contaminated liquids, can be discharged from the clean room region.

It can be provided that the cleaning device has one or more distribution elements, for example nozzles and/or sprinklers, which are connected to a cleaning agent source within the clean room region and/or can be connected to a cleaning agent source in the surroundings of the production system and by means of which cleaning agents (i.e., distribution elements), for example steam and/or hydrogen peroxide, can be distributed for cleaning.

By means of the cleaning device, in particular objects coming into direct contact with reactants, in particular tools and/or consumable materials, can be cleanable, in particular sterilizable, in particular by means of irradiation.

By means of the cleaning device, in particular objects which are not in direct contact with reactants can be cleaned, in particular disinfected, in particular by means of gassing.

The cleaning device can comprise an in particular stationary cleaning station, by means of which at least one workpiece carrier, in particular at least one receiving box, can be cleaned, in particular disinfected and/or sterilized.

The workpiece carrier can be supplied to the cleaning station by means of the storage transport device and/or the handling device.

The cleaning station can comprise a washing machine and/or an autoclave device.

The method according to the invention is described below.

All structural and functional features that are associated with the previously described system according to the invention, i.e., the production system according to the invention, and its embodiments, can also be included in the method according to the invention either alone or in combination, and the associated properties, configurations and advantages can also be correspondingly included and achieved.

In addition, the production system according to the invention described above can be configured to carry out the following method according to the invention, and the following method according to the invention can be designed to be executable by means of the production system according to the invention described above.

A method according to the invention for producing a product, in particular a biological-pharmaceutical product, by means of a production system, in particular a production system as described above (i.e., which in particular comprises: a clean room region, an airlock device for supplying an object from the surroundings of the production system into the clean room region and/or for removing an object from the clean room region, a handling device for moving the object within the clean room region, and a storage device arranged within the clean room region, which comprises a plurality of storage spaces for receiving a plurality of objects) (the method) comprises the following:

selecting one of a plurality of production programs for producing one of a plurality of products producible by means of the production system, introducing a reactant into an airlock device of the production system, automatically transporting the reactant into a clean room region of the production system, and automatically performing one or more treatment processes on the reactant.

It can be provided that, after completion of the treatment processes, an automatic transport of a product produced from the reactant from the production system takes place.

The reactant can be a patient-related or a pooled reactant.

A pooled reactant can be producible and/or produced from a plurality of patient-related reactants in order to serve to produce a product for a patient and/or a patient group, i.e., in other words: for producing a product for one or more patients.

The treatment processes can have pooling of two or more reactants in order to produce a pooled reactant.

The treatment processes can have an in particular recurring pairing and/or combining of objects, in particular tools or tool units, reactants, consumable materials, etc., in order to image the in particular biological production process in its individual process steps.

When the reactant is automatically transported into the clean room region of the production system, the reactant can be stored in a storage space of a storage device of the production system located within the clean room region.

One or more treatment processes can be carried out fully automatically until a product to be produced from the reactant is completed.

Alternatively, one or more treatment processes can be carried out fully automatically until a product to be produced from the reactant is finished, taking into account a quality analysis carried out or able to be carried out, in particular by means of one or more sensor units or sensor systems.

One or more, in particular all, treatment processes can be carried out at the storage space.

The product thus produced can be removed from the storage space and transported automatically to the airlock device for the removal of same from the production system.

The product can be filled and/or packaged before it is removed, in particular filled and/or packaged ready for use.

One or more vessels, receptacles and/or tools which have been used to produce the product can remain at least partially within the clean room region after the product has been completed, can be cleaned and sterilized, and can then be reused for producing a further product.

In order to produce the product and/or to produce a plurality of different products, required consumable materials, in particular consumable substances and/or tool consumables, can be stored within the clean room region, in particular before a selection of the product to be produced is made.

The consumable materials can be automatically transported into the clean room region via the airlock device and stored there in particular in one or more storage spaces of the storage device.

An amount of consumable materials stored within the clean room region can be monitored and, when a predefined minimum amount is undershot, the supply can be increased by supplying the required consumable materials, in particular via an indication or a warning message at an operator unit.

A plurality of products, in particular a plurality of different products, can be produced simultaneously within the clean room region.

One or more treatment processes which can be carried out in particular by means of one or more tool units can comprise:

supplying a liquid and/or a gas, in particular a gas mixture, discharging, in particular pumping off, a liquid and/or a gas, in particular a gas mixture, discharging, in particular pumping off, a portion of a liquid and/or a gas, in particular a gas mixture, for an analysis by means of one or more sensor units, mixing one or more components, in particular at least one liquid, with at least one further component, for example a further liquid, concentrating and/or separating a liquid, in particular by means of a column, for example a separation column, and/or a centrifuge, analyzing a reactant and/or an intermediate product and/or a product, in particular by means of one or more sensor units, storing, in particular placing into storage and/or retrieving, one or more objects, in particular by means of the storage transport device, controlling the temperature of, in particular incubating, one or more objects, in particular one or more reactants.

It should be understood that the preceding list of the treatment processes is exemplary and not exhaustive.

Alternatively or additionally, it can be provided that one or more treatment processes can be combined with one or more treatment processes in a single treatment process and/or in any combination thereof.

A combination of treatment processes can result in particular from instructions, in particular a formulation, for producing a product, in particular instructions for producing a personalized product based on patient-related information.

A treatment process can, for example, comprise a supply of a consumable material, in particular a liquid, to a reactant, wherein, in particular, once a workpiece carrier, by means of which the consumable material, in particular the liquid is held, and a workpiece carrier, in particular a receiving box, by means of which the reactant and/or a reactant container or a vessel with a reactant is held, are in particular fluidically connected to one another by means of one or more tool units and/or a handling device, the consumable material is supplied to the reactant, in particular directed and conveyed in a defined manner to the reactant.

It can be provided that the interconnected workpiece carriers define a process cell, in particular an aseptic process cell, or a process unit, in particular an aseptic process unit. As a result, for example, a suspension of the liquid and of the reactant, in particular a cell suspension, can be generated and/or changed in a defined manner.

Furthermore, it can be provided that after the supply, in particular the conveying, the workpiece carriers can be separated from one another again by means of the one or more tool units and/or the handling device.

It can be provided that one or more tool units and/or a, or the, handling device are cleaned and/or sterilized by means of a cleaning device before or after a treatment process.

After cleaning and/or sterilization has taken place, the tool units can be stored in a storage space again by means of the storage transport device.

Additionally or alternatively, after cleaning and/or sterilization has taken place, the handling device can in particular be refitted with one or more tool units and/or retrofitted for a subsequent treatment process.

A treatment process can, for example, comprise incubation of a reactant, in particular of a portion of a reactant, for example of cells, in particular at a storage space.

The incubation can be carried out after a consumable material is supplied, in order to generate a cell suspension; the incubation can be carried out before a consumable material is supplied, for example to change a cell suspension, in particular at a storage space.

It can be provided that the workpiece carrier on which the cell suspension is arranged is cleaned and sterilized by means of a cleaning device before the incubation can be carried out or is carried out.

During incubation, gassing and temperature control can be carried out or is carried out by means of one or more tool units.

During incubation, one or more functions, in particular heating, fixing and/or gassing, can be carried out in a, in particular single, receiving box.

It can be provided that a workpiece carrier, in particular the workpiece carrier by means of which the consumable material, in particular the liquid, is or has been held, can be cleaned and/or sterilized in parallel or in series with a treatment process, in particular the incubation, by means of the cleaning device.

In addition, it can be provided that a container held by means of the workpiece carrier, in which the liquid was stored, can be removed or is removed from the clean room region by means of the handling device via the airlock device. Optionally, the workpiece carrier can subsequently be cleaned and/or sterilized or is cleaned and/or sterilized by means of the cleaning device. Furthermore, the workpiece carrier can then optionally be loaded again, in particular with consumable material, in particular from the storage device and/or via the airlock device by means of the storage transport device and/or the handling device.

A sequence of treatment processes, which are carried out by means of tools which are arranged within the clean room region and remain in the clean room region after the treatment processes have been carried out, can be associated with each product to be produced.

One or more tools are cleaned, in particular sterilized, after one or more treatment processes within the clean room region are carried out.

One or more tools can be equipped with tool consumables before one or more treatment processes within the clean room region are carried out.

One or more tool consumables can be removed from the one or more tools and/or disposed of after one or more treatment processes within the clean room region have been carried out. A plurality of, in particular all, treatment processes can be associated with treatment time values which indicate that time period which elapses from a start of the corresponding treatment process up to its end, in particular including:

a time period for providing the at least one tool required for the corresponding treatment process, in particular including its equipping with one or more tool consumables, and/or a time period for the supply and/or arrangement and/or startup of the at least one tool on the reactant to be treated, in particular at a storage space at which the reactant is arranged, and/or a duration of the effect on the reactant in order to achieve a desired treatment result, and/or a time period for removing the at least one tool from the reactant, in particular from the storage space;
preferably including:

cleaning of the at least one tool, and/or removing and/or disposing of tool consumables, and/or a return transport of the tool to a starting location, in particular a storage space associated with the tool.

In each production program, the treatment processes required for the production of a specific product and the associated treatment time values can be stored or taken into account.

When a production program is started, a prediction of a production sequence can be created and the tools required and/or provided for carrying out the treatment processes can be reserved for time slots resulting from the prediction.

One or more treatment processes can each be assigned one or more cleaning processes for cleaning one or more tools and/or for cleaning one or more storage spaces, and/or one or more disposal processes for disposing of consumable materials, and/or one or more set-up processes for equipping one or more tools with consumable materials, and/or one or more control processes for controlling a treatment result, wherein, depending on the prediction of the production process, time slots can be reserved at one or more of those devices that are required for carrying out the one or more cleaning processes, the one or more disposal processes, the one or more set-up processes, and/or the one or more control processes.

After one or more treatment processes, in particular after each treatment process, the prediction of the production sequence can be checked and/or updated, in particular for confirming or correcting the time slots for the tools that are still required and/or other devices for completing the product.

At a desired start of a production program, it can be determined on the basis of a prediction of the production sequence whether all required tools and/or other devices for finishing the product are available within the required time slots, and the production program can only be started if this determination has supplied a positive result.

Additionally or alternatively, when an entire production program and/or a portion of a production program is started, it can be determined on the basis of a prediction of the production sequence whether all required tools and/or other devices for finishing the product are available within the required time slots and/or the production duration and/or whether resource bottlenecks, in particular with regard to consumable materials, and/or other production risks, are available, and the production program can only be started if this determination has provided a positive result with respect to the availability and a negative result regarding the resource bottlenecks and the production risks.

Additionally or alternatively, it can be provided that, at a desired start of a production program and/or a portion of a production program, it is determined on the basis of a prediction of the production sequence whether all required tools and/or other devices and/or objects and/or other materials are available for completion of the product within the required time slots and/or can be supplied within the required time slots, in particular by a user, for example whether a confirmation can be entered by the user, that said tools, devices, objects, and/or materials can be supplied within the required time slots, and the production program can only be started when this determination has a positive result.

It can be provided that the production system comprises one or more control units, in particular the control units already described, for open-loop and/or closed-loop control of the production system, in particular for open-loop and/or closed-loop control of at least one component comprised by the production system or a component of the production system.

The production system can have one or more storage units and/or can be assigned one or more, in particular decentralized, storage units, for example in a cloud and/or on a server, wherein a computer program product is storable or stored on at least one storage unit, which computer program product comprises instructions which, when the computer program product is executed by at least one control unit of the production system, causes the production system described above to carry out a method described above.

The computer program product can additionally or alternatively be stored on a computer-readable (further) storage medium.

By means of one or more control units, a product, in particular a biological-pharmaceutical product, can be produced by means of the production system.

One or more control units can be designed and programmed to categorize one or more products to be produced in production batches in particular in an automated manner.

One or more control units can be designed and programmed to carry out an application planning of one or more products and/or of production batches, in particular in terms of time and/or with regard to resources located within the production system, for example tools and/or consumable materials, and/or a current utilization of the production system.

Additionally or alternatively, said application planning can be feasible with regard to a predetermined production strategy, such as, for example, with respect to a quality, for example product quality, over a time course and/or with respect to costs over a time course.

One or more control units can be designed and programmed to be able to access and/or modify the information management unit storable or stored on one or more storage units.

One or more control units can be designed and programmed to be able to access and modify an accounting unit storable or stored on one or more storage units, whereby an automated billing and/or cost calculation of products to be produced can be made possible.

One or more control units can be designed and programmed to encrypt and decrypt information, in particular patient-related information for the production of a product that can be stored on at least one memory unit, for example in the information management unit.

Additionally or alternatively, it can be provided that one or more control units are designed and programmed to anonymize and/or to pseudonymize information, in particular patient-related information for the production of a product that can be stored on at least one memory unit, for example in the information management unit.

By means of the information management unit, information can be managed, in particular can be stored and/or can be changed and/or can be generated, which information, for example, comprises: one or more formulations of one or more products and/or intermediate products, patient-related information, machine-related information relating to the production system, run time information relating to the production system, information about material logistics and/or material requirements of the production system.

By means of one or more storage units, instructions for producing a product, in particular instructions for producing a personalized product based on patient-related information, can be storable.

A reactant can be a patient-related reactant.

Additionally or alternatively, a reactant can be a pooled reactant.

A pooled reactant can be producible and/or produced from a plurality of patient-related reactants in order to serve to produce a product for a patient and/or a patient group, i.e., in other words: for producing a product for one or more patients.

The instructions for producing a product can define a sequence of one or more treatment processes.

The instructions can otherwise define a production program.

It can be provided that one or more production programs can be stored on one or more storage units and can be executed for producing one of a plurality of products that can be produced by means of the production system, in particular by means of one or more control units.

By means of the production system, a product, in particular a patient-related product, can be produced from at least one reactant, in particular from at least one patient-related reactant, on the basis of the instructions based on the patient-related information.

One or more control units can be designed and programmed to be able to communicate with one or more communication interfaces and/or one or more human-machine interfaces, for short: HMI interfaces, of the production system.

One or more control units can be designed and programmed to provide information to a human operator or user via the communication interfaces and/or via the HMI interfaces, for example fault information and/or information about a state of a production of a product and/or information about inventory stocks of the storage device.

Referring to the preceding description of the production system according to the invention and the method according to the invention, an exemplary sequence, in particular an exemplary material flow, of one or more objects of the production system and/or an exemplary sequence, in particular an exemplary material flow, of one or more objects that can be supplied and/or removed from the production system is described below in order to additionally explain the present invention.

It should be understood that the following exemplary sequences and/or material flows can be modified with respect to all structural and functional features associated with the production system according to the invention and its embodiments described above, and also with respect to all method features of the above-described method according to the invention and its embodiments either alone or in any combination.

The following description in particular refers to a reactant:

A reactant can be arranged and/or received in a container, in particular a reactant container or a vessel.

The reactant container with the reactant can define a clean room sub-region with a clean room class A.

The reactant container with the reactant can be packaged by means of a packaging, which can be formed in the sense of a sub-region housing of the reactant container with the reactant.

The reactant container with the reactant can be introduced into the airlock device of the production system, in particular at an inlet airlock space of the airlock device.

The packaging of the reactant container can in particular be removable from the reactant container at the inlet airlock space and/or at a separate unpacking space in the airlock device, in particular by means of one or more unpacking units.

It can preferably be provided that the packaging is cleaned and/or sterilized before removal by means of a cleaning device of the airlock device or a part of the cleaning device of the production system associated with the airlock device.

The airlock device can comprise a clean room region with a clean room class B.

The inlet airlock space and/or the unpacking space can comprise a clean room sub-region with a clean room class A.

It can be provided that the reactant container can be moved with the reactant within the airlock device by means of an airlock transport device and/or the handling device.

By means of the handling device, the reactant container can be transferable with the reactant in or directly adjacent to the airlock device to a workpiece carrier, in particular a receiving box, or can be transferable to a workpiece carrier which is arrangeable or arranged in a receiving box.

The receiving box, which has received the reactant container with the reactant, can define an aseptic process unit.

The receiving box, which has received the reactant container with the reactant, can be put into storage in or at a storage space of the storage device by means of a storage transport device of the storage device.

Additionally or alternatively, this receiving box can be provided for one or more treatment processes, in particular by means of one or more tool units by means of the storage transport device.

Additionally or alternatively, it can be provided that the reactant container can be transferred with the reactant in or directly adjacent to the airlock device by means of the handling device, and this workpiece carrier can be transported after the transfer of the reactant container to a storage space by means of the storage transport device, wherein, after storage in the storage space, the workpiece carrier can be transferred together with the reactant container from the storage space to a receiving box which defines an aseptic process unit in particular with a clean room class A.

By means of the storage transport device, one or more workpiece carriers, by means of which one or more tool units are held and transported from the storage device, and/or one or more consumable materials from the storage device can be transportable to the receiving box, wherein, optionally, the workpiece carriers can be arranged in a corresponding receiving box.

The receiving box and the one or more workpiece carriers or the receiving boxes in which a respective workpiece carrier is arranged can be connectable/coupleable or connected/coupled to the reactant arranged in the receiving box for one or more treatment processes, wherein one or more tool units and/or one or more consumable materials of the one or more workpiece carriers can be required for one or more treatment processes of the treatment processes.

In other words, it can also be provided that the receiving box and one or more further receiving boxes are connectable/coupleable or connected/coupled to one another, wherein the further receiving boxes each have received at least one workpiece carrier, by means of which one or more tool units and/or one or more consumable materials are holdable or are held for one or more treatment processes.

A product can be generatable from the reactant by means of the treatment processes.

To a certain extent, the reactant container held in the receiving box can now be referred to as a product container.

Additionally or alternatively, a separate container which can be assigned to the consumable materials can also be providable and/or provided by means of a workpiece carrier, which can serve as a product container in which the product can be transferred by means of one or more tool units.

The product container with the product which is arranged in the receiving box can be movable by means of the storage transport device and/or the airlock transport device and/or handling device to an outlet airlock space, in particular to a packaging space, of the airlock device.

The product container with the product can be packageable or packaged at the outlet airlock space, in particular at the packaging space, in particular by means of one or more packaging units, in order to subsequently be removable from the airlock device or removed therefrom.

In particular, the following description refers to a workpiece carrier or a receiving box:

The workpiece carrier can in particular be designed in the functional sense as a receiving box for receiving reactants. To a certain extent, the workpiece carrier can be configured to have and to fulfill the function of a receiving box.

Additionally or alternatively, it can be provided that the production system comprises a plurality of receiving boxes for receiving one or more workpiece carriers together with the reactants arranged and/or received thereon.

A workpiece carrier or a receiving box can be supplied to the clean room region via the airlock device.

The workpiece carrier or the receiving box can be cleaned and/or sterilized in the airlock device by means of a cleaning device of the airlock device or a part of the cleaning device of the production system associated with the airlock device.

The workpiece carrier or the receiving box can be mounted on a storage space of the storage device by means of a storage transport device of the storage device, which can be transferred to the workpiece carrier or the receiving box by means of an airlock transport device and/or the handling device.

If required, the workpiece carrier and/or the receiving box can be supplied from the storage space, starting from a specific use, by means of the storage transport device and, optionally, the handling device and/or the airlock transport device.

For example, the workpiece carrier can be equipped with one or more reactants and/or one or more tool units and/or one or more consumable materials, or can be equipped, for example, by means of the handling device, in particular in order to be storable or stored in the storage device, or can be provided for one or more treatment processes, wherein in particular a plurality of workpiece carriers can be provided in such a way.

The workpiece carriers can be arranged in corresponding receiving boxes, for example by means of the handling device, by means of which the workpiece carriers can be stored and/or provided.

Additionally or alternatively, it can be provided that the workpiece carriers can be arranged in corresponding receiving boxes, for example by means of the handling device and/or an actuator system configured in the corresponding receiving box and/or on the corresponding workpiece carrier by means of which the workpiece carriers can be stored and/or provided.

A plurality of workpiece carriers, in particular workpiece carriers designed as a receiving box, and/or receiving boxes can be connectable/coupleable to one another in order to form an aseptic process unit for carrying out one or more treatment processes.

For example, a workpiece carrier designed as a receiving box or arranged in a receiving box, which workpiece carrier has received a reactant container with a reactant, a workpiece carrier designed as a receiving box or arranged in a receiving box, which workpiece carrier has received consumable material for one or more treatment processes, and a workpiece carrier designed as a receiving box or arranged in a receiving box, which workpiece carrier has received one or more tool units for one or more treatment processes, are connectable or coupleable or connected/coupled to one another, in particular by means of the storage transport device and/or the handling device, in order to form a common aseptic process unit in order to then enable one or more treatment processes to be carried out.

After the treatment processes have been carried out, the workpiece carriers or the receiving boxes can be detachable/decoupable or detached/decoupled from one another again.

As described above, the receiving box with the product produced is transported to the airlock device by means of the storage transport device.

The aforementioned workpiece carriers or receiving boxes associated with the tool units and the consumable materials can be supplied to a cleaning device of the production system by means of which the workpiece carriers can be cleaned and/or sterilized.

The cleaned and/or sterilized workpiece carriers or receiving boxes can again be storable at storage spaces of the storage device and can be available for reuse.

The description below refers in particular to a tool or a tool unit and to a consumable material:

A tool unit or a consumable material can be supplied to the clean room region via the airlock device.

The tool unit or the consumable material can be introduced into the airlock device of the production system, in particular at an inlet airlock space of the airlock device.

The tool unit or the consumable material can be cleaned and/or sterilized in the airlock device by means of a cleaning device of the airlock device or a part of the cleaning device of the production system associated with the airlock device.

It can be provided that the tool unit or the consumable material has a packaging which, in particular, can be removable from the tool unit or the consumable material in the airlock device, in particular at the inlet airlock space and/or at a separate unpacking space, in particular by means of one or more unpacking units.

It can preferably be provided that the packaging is cleaned and/or sterilized before removal by means of the cleaning device of the airlock device.

The tool unit or the consumable material can be mounted on a storage space of the storage device by means of a storage transport device of the storage device, which can be transferred to the tool unit or the consumable material on a workpiece carrier by means of the handling device by means of a airlock transport device and/or the handling device.

It can be provided that the tool unit or the consumable material can be moved within the airlock device by means of an airlock transport device and/or the handling device.

By means of the handling device, the tool unit or the consumable material can be transferable in or directly adjacent to the airlock device to a workpiece carrier, in particular a receiving box, or can be transferable to a workpiece carrier which is arrangeable or arranged in a receiving box.

The workpiece carrier or the receiving box which has received the tool unit or the consumable material can be storable in a storage space of the storage device by means of a storage transport device of the storage device.

This workpiece carrier or this receiving box can be providable or provided for one or more treatment processes by means of the tool unit or using the consumable material by means of the storage transport device as already described in conjunction with the reactant and the workpiece carrier or the receiving box.

After one or more treatment processes have been carried out and after the receiving boxes are detached/decoupled again from one another, the tool unit used or the consumable material used can be supplied to the handling device by means of the storage transport device, wherein in particular single-use components can be removed from the tool unit as required by means of the handling device, in particular before cleaning and/or sterilization by the cleaning device.

Furthermore, after one or more treatment processes are carried out and after the receiving boxes are again detached/decoupled from each other, the tool unit used can be supplied to the cleaning device by means of the storage transport device.

Additionally or alternatively, it can be provided that a consumable material used, in particular a liquid consumable material used, can be removed during one or more treatment processes from the corresponding receiving box and, optionally, from the production system, in particular via the airlock device.

Used and/or damaged tool units or consumable materials used can be removable from the clean room region via the airlock device by means of the handling device.

The cleaned and/or sterilized tool unit can again be storable at a storage space of the storage device and can be available for reuse.

Referring to the preceding description, the present invention can create a fully automated overall system for producing biological-pharmaceutical products for industrial production of individual batch sizes, in particular individual and/or small batch sizes, in particular with modularly configured and/or autonomously acting components.

With the present invention, in particular by means of the provided sensor system or the provided sensor units, analytical functions can be integrated in automated processes, in particular treatment processes, so that ambient and/or processing conditions required for the growth of cells outside an organism can be finely tunable and/or controllable and/or adjustable, whereby an efficient production of the product can be ensured.

With the present invention, in particular by the flexible and modular structure of the production system which can be made possible by the various devices, both individual and/or small batch variables and a large-volume production of biological-pharmaceutical products can be carried out automatically, in particular fully automatically, for example for the production of autologous and/or allogeneic cell therapeutics, the starting material of which, in particular patient-own cells, react highly sensitively to their ambient conditions.

With the present invention, in particular by the cleaning device integrated into the clean room region and the storage device, a fully automated overall system can be created for producing biological-pharmaceutical products, which overall system can be both equipped in an automated manner and can clean and sterilize objects required for treatment processes on a reactant and can thus prepare again for an aseptic production region.

With the present invention, biological-pharmaceutical products, in particular personalized therapeutics, can be produced in an automated, in particular fully automated, and flexible manner, in particular due to the individually assemblable treatment processes in an in particular single process space, for example the clean room region and/or a storage space and/or a receiving box.

Compared to the usually existing permanently linked individual process steps of conventional production processes of comparable biological-pharmaceutical products, a more efficient system and method can be created with the present invention.

The present invention can create a system, i.e., the production system, and a method by means of which a human operator or user is no longer required in the immediate process environment, whereby in particular both a production efficiency can be increased and a probability of manual errors can be reduced.

Additionally or alternatively, the production system can take up less space or installation space, since a human operator or user has to enter the clean room region of the production system only in emergency cases and/or during maintenance.

A cost-intensive building and space structure can thus be reduced economically and technically to the reactant to be processed directly, in other words the biological workpiece to be processed, which is to be converted to the product.

An ultrapure environment, in particular clean room class A, in which the product is processed open, can be reduced to a minimum.

It can be particularly advantageous that, in the present invention, all necessary systems and/or devices can be present for autonomous operation and associated equipment and/or consumable materials within the production system, and furthermore all necessary information for autonomous operation within the production system can be kept and/or processed in particular by means of one or more control units.

As the above description shows, the invention relates in particular to a production system and a method according to one of the following sentences in which special embodiments of the invention are also described:

1. A production system, in particular for producing biological-pharmaceutical products, wherein the production system comprises the following:
   a clean room region;
   an airlock device for supplying an object from the surroundings of the production system into the clean room region and/or for removing an object from the clean room region;
   a handling device for moving the object within the clean room region;
   a storage device which is arranged within the clean room region and which comprises a plurality of storage spaces for receiving a plurality of objects.

2. The production system according to sentence 1, characterized in that the storage device comprises a storage transport device for transporting objects to the storage spaces and/or away from the storage spaces.

3. The production system according to sentence 2, characterized in that the storage transport device is a device different from the handling device.

4. The production system according to sentence 2 or 3, characterized in that the storage transport device comprises a rail-guided transport system and/or one or more free-moving transport vehicles.

5. The production system according to one of sentences 2 to 4, characterized in that the storage transport device comprises one or more rail-guided storage transport units by means of which one or more storage racks of the storage device are accessible in particular for storage and retrieval processes and for treatment processes and/or maintenance processes.

6. The production system according to one of sentences 2 to 5, characterized in that the storage transport device comprises one or more storage transport units designed as gantry conveyors.

7. The production system according to one of sentences 1 to 6, characterized in that the handling device is a multi-axis robot arm or comprises same.

8. The production system according to one of sentences 2 to 7, characterized in that a changing device of the production system is associated with the storage transport device and/or the handling device, by means of which changing device different gripping units and/or carrier units can be mounted on one or more storage transport units of the storage transport device and/or on one or more handling units of the handling device, in particular for carrying out different storage processes, transporting processes, handling processes, maintenance processes and/or treatment processes by means of the corresponding storage transport unit and/or handling unit.

9. The production system according to one of sentences 2 to 8, characterized in that a cleaning device of the production system is associated with the storage transport device and/or the handling device, by means of which cleaning device at least one gripping unit and/or carrier unit of one or more storage transport units of the storage transport device and/or one or more handling units of the handling device can be cleaned, in particular after carrying out a storage process, transport process, handling process, maintenance process and/or treatment process.

10. The production system according to one of sentences 2 to 9, characterized in that one or more objects are transferable from an airlock space of the airlock device to a storage transport device, in particular to one or more storage transport units of a storage transport device, by means of the handling device.

11. The production system according to one of sentences 1 to 10, characterized in that the handling device comprises an airlock transport device by means of which one or more objects can be transported from an airlock space, in particular an inlet airlock space, to a further airlock space, in particular a transfer airlock space, and/or from an airlock space, in particular a transfer airlock space, to a further airlock space, in particular an outlet airlock space.

12. The production system according to one of sentences 2 to 11, characterized in that the storage transport device and/or the handling device each comprise one or more workpiece carrier receptacles for receiving and transporting one or more workpiece carriers.

13. The production system according to one of sentences 1 to 12, characterized in that the airlock device comprises a cleaning device for cleaning one or more workpiece carriers and/or for cleaning one or more workpiece carrier receptacles.

14. The production system according to one of sentences 1 to 13, characterized in that the production system comprises a cleaning device which can be supplied to workpiece carriers for cleaning same, in particular after the transport of an object by means of the corresponding workpiece carrier.

15. The production system according to one of sentences 1 to 14, characterized in that the storage device comprises one or more storage racks and/or one or more storage space areas which each have a plurality of storage spaces, wherein reactants and/or tools and/or consumable materials can be stored in or removed from the storage spaces by means of the storage transport device.

16. The production system according to one of sentences 1 to 15, characterized in that the production system comprises a plurality of workpiece carriers which serve to receive reactants and/or tools and/or consumable materials.

17. The production system according to sentence 16, characterized in that the workpiece carriers remain within the clean room region permanently, in particular over one or more complete production processes.

18. The production system according to one of sentences 1 to 17, characterized in that the production system comprises a plurality of types of workpiece carriers which differ from one another with regard to the shape and/or dimensioning of a receiving region of the corresponding workpiece carrier.

19. The production system according to one of sentences 16 to 18, characterized in that one type of workpiece carriers serves to receive a vessel for receiving a reactant.

20. The production system according to one of sentences 16 to 19, characterized in that one type of workpiece carriers for receiving one or more tool units and/or tool consumables is used to carry out a treatment process on a reactant and/or for carrying out a maintenance process within the clean room region.

21. The production system according to one of sentences 16 to 20, characterized in that one type of workpiece carriers is used to receive consumable materials for feeding same to a reactant and/or to carry out a treatment process on a reactant.

22. The production system according to one of sentences 16 to 21, characterized in that one or more workpiece carriers each comprise one or more action units for carrying out an action on a reactant and/or on a tool.

23. The production system according to one of sentences 16 to 22, characterized in that one or more action units are designed as a treatment unit for carrying out a treatment process on the reactant.

24. The production system according to one of sentences 16 to 23, characterized in that one or more action units are designed as a sensor unit for determining a current value of a parameter of the corresponding workpiece carrier and/or of a reactant arranged thereon and/or of a tool arranged thereon and/or of consumable materials arranged thereon.

25. The production system according to one of sentences 16 to 24, characterized in that one or more workpiece carriers comprise a storage device for storing energy and/or one or more consumable materials.

26. The production system according to one of sentences 16 to 25, characterized in that the workpiece carriers are reusable several times, in particular in that the storage device can be electrically recharged and/or can be refilled with consumable material.

27. The production system according to one of sentences 1 to 26, characterized in that the production system comprises a charging station arranged within the clean room region for charging the storage device and/or a refilling station arranged within the clean room region for filling the storage device.

28. The production system according to one of sentences 1 to 27, characterized in that the production system comprises a plurality of workpiece carriers designed as receiving boxes for receiving reactants or a plurality of receiving boxes for receiving one or more workpiece carriers together with the reactants arranged and/or received thereon.

29. The production system according to sentence 28, characterized in that the receiving boxes can be stored in storage spaces of the storage device, in particular fully automatically by means of a storage transport device of the storage device.

30. The production system according to sentence 28 or 29, characterized in that one or more of the receiving boxes surround a closable interior.

31. The production system according to one of sentences 28 to 30, characterized in that the receiving boxes can be opened and/or closed automatically and/or by means of the handling device for introducing a reactant and/or for removing a product produced from a reactant.

32. The production system according to one of sentences 28 to 31, characterized in that one or more of the receiving boxes in each case comprises one or more conditioning units which are integrated or detachably arranged thereon or are detachably arrangeable thereon, by means of which conditioning units a temperature and/or a pressure and/or a moisture and/or a gas composition in the interior of the corresponding receiving box can be influenced, in particular can be subjected to open-loop and/or closed-loop control.

33. The production system according to sentence 32, characterized in that one or more of the conditioning units are tool units of a tool system of the production system, which can be arranged on the corresponding receiving box if necessary or can be removed therefrom, in particular fully automatically by means of a storage transport device of the storage device and/or by means of the handling device.

34. The production system according to one of sentences 28 to 33, characterized in that the receiving boxes comprise one or more connection elements which can be connected to connection elements corresponding thereto at one or more treatment stations, in particular in order to supply the corresponding receiving box with electrical energy and/or consumable substances, in particular liquids and/or gases, and/or to produce a signal-related coupling of the corresponding receiving box to an in particular superordinate control device.

35. The production system according to one of sentences 1 to 34, characterized in that the storage device comprises storage spaces provided with connection elements, so that one or more treatment processes can be carried out for the treatment of the reactants at storage spaces of the storage device serving as treatment stations.

36. The production system according to one of sentences 28 to 35, characterized in that the storage spaces of the storage device and/or the receiving boxes comprise fixing elements by means of which the receiving boxes can be positioned and/or fixed at the storage spaces.

37. The production system according to one of sentences 28 to 36, characterized in that the receiving boxes each comprise one or more tool holders for receiving and fixing one or more tools, in particular in the interior of the corresponding receiving box.

38. The production system according to sentence 37, characterized in that the one or more tool holders each comprise one or more connection elements which can be connected to connection elements corresponding thereto on the tool to be received in each case, in particular in order to supply the corresponding tool with electrical energy and/or consumable substances, in particular liquids and/or gases, and/or in order to produce a signal-related coupling of the corresponding tool to the receiving box and/or to an in particular superordinate control device.

39. The production system according to one of sentences 1 to 38, characterized in that the storage device comprises one or more storage racks and/or one or more storage space areas which each have a plurality of storage spaces.

40. The production system according to one of sentences 1 to 39, characterized in that, by means of a storage transport device of the storage device, reactants and/or workpiece carriers and/or tools and/or consumable materials can be stored and/or removed from the storage spaces.

41. The production system according to sentence 40, characterized in that one or more storage spaces are accessible from a plurality of directions and/or by means of a plurality of storage transport units of the storage transport device.

42. The production system according to sentence 40 or 41, characterized in that the storage spaces are accessible laterally from above or in the horizontal direction by means of the storage transport device in the vertical direction.

43. The production system according to one of sentences 1 to 42, characterized in that a plurality of substantially horizontally aligned rows of storage spaces are arranged one above the other in the vertical direction.

44. The production system according to one of sentences 1 to 43, characterized in that a plurality of the storage spaces, in particular all storage spaces, are rack spaces of one or more storage racks.

45. The production system according to one of sentences 1 to 44, characterized in that the storage device comprises a plurality of different types of storage spaces for receiving different types of workpiece carriers.

46. The production system according to sentence 45, characterized in that the different types of storage spaces differ from one another with regard to their shape and/or dimensioning.

47. The production system according to sentence 45 or 46, characterized in that the different types of storage spaces differ from one another with regard to their function and/or equipment.

48. The production system according to one of sentences 45 to 47, characterized in that the different types of storage spaces are arranged in a regular pattern distributed in a storage space rack and/or a storage space area of the storage device.

49. The production system according to one of sentences 1 to 48, characterized in that the storage device has a plurality of regions for receiving different types of workpiece carriers.

50. The production system according to one of sentences 1 to 49, characterized in that the storage device comprises a plurality of storage spaces which form treatment stations for treating reactants.

51. The production system according to one of sentences 1 to 50, characterized in that the storage device comprises a plurality of storage spaces which form tool stations for storage, maintenance, cleaning, changing, electrical charging and/or for control of tools.

52. The production system according to one of sentences 1 to 51, characterized in that the production system comprises an unpacking device for unpacking objects to be supplied to the clean room region.

53. The production system according to sentence 52, characterized in that the unpacking device is integrated into the airlock device or forms a component thereof.

54. The production system according to one of sentences 1 to 53, characterized in that the airlock device comprises an inlet airlock space which is accessible from the surroundings of the production system and on which a packaged object can be arranged in particular by a person or automatically.

55. The production system according to sentence 54, characterized in that the packaged object can be transported from the inlet airlock space to an unpacking space by means of an airlock transport device of the production system and can be unpacked at the unpacking space in an automated manner, or in that the packaged object can be unpacked in an automated manner, and/or characterized in that the production system has an autoclave device, which can be loaded and/or unloaded from one side, in particular manually, by a user, and from another side within the clean room region, in particular after sterilization and drying by the autoclave device, can be unloaded and/or loaded in particular by means of the handling device and/or the storage transport device, as a result of which small packaged or partially packaged objects and/or unpacked objects can be introduced aseptically into and out of the clean room region.

56. The production system according to one of sentences 1 to 55, characterized in that the airlock device comprises a cleaning device for cleaning a packaging of the packaged object.

57. The production system according to one of sentences 52 to 56, characterized in that the unpacking device comprises a plurality of unpacking units for unpacking different types of objects and/or packaging, in particular for removing different types of packaging from the objects.

58. The production system according to sentence 57, characterized in that one or more unpacking units are designed for unpacking reactants and one or more further unpacking units for unpacking tools and/or consumable materials.

59. The production system according to one of sentences 52 to 58, characterized in that the unpacking device comprises a detection device and a control device by means of which a type of the object to be unpacked and/or a type of the packaging to be removed can be determined.

60. The production system according to sentence 59, characterized in that an unpacking unit of the unpacking device for carrying out the unpacking process can be selected and actuated by means of the control device, wherein the unpacking unit is one of a plurality of unpacking units for carrying out different unpacking processes, wherein the selected unpacking unit is associated with the determined type of object to be unpacked and/or the type of packaging to be removed.

61. The production system according to one of sentences 1 to 60, characterized in that the production system comprises a tool system by means of which treatment processes can be carried out at reactants and/or maintenance processes can be carried out within the clean room region.

62. The production system according to sentence 61, characterized in that the tool system comprises a plurality of, in particular fully automatic, tool units for carrying out different treatment and/or maintenance processes.

63. The production system according to sentence 61 or 62, characterized in that the tool system comprises one or more tool units designed as supply units for supplying consumable materials to the reactants.

64. The production system according to one of sentences 61 to 63, characterized in that the tool system comprises one or more tool units designed as removal units for removing a sample from a reactant.

65. The production system according to one of sentences 61 to 64, characterized in that one or more of the tool units of the tool system in each case comprises one or more multi-use components and one or more single-use components.

66. The production system according to one of sentences 61 to 65, characterized in that the tool system comprises a set-up unit by means of which one or more single-use components of a tool unit after use thereof can be removed, in particular can be disposed of, and can be replaced by one or more new single-use components.

67. The production system according to sentence 66, characterized in that the set-up unit is arranged completely within the clean room region.

68. The production system according to sentence 66 or 67, characterized in that the set-up unit comprises a handling unit, in particular a multi-axis robot arm and/or a pick-and-place robot and/or a cable robot, by means of which a fully automatic set-up process can be carried out.

69. The production system according to one of sentences 66 to 68, characterized in that the set-up unit comprises a cleaning unit, or in that a cleaning unit is associated with the set-up unit, by means of which cleaning unit multi-use components of one or more tool units can be cleaned, in particular sterilized, after use.

70. The production system according to one of sentences 61 to 69, characterized in that the tool system comprises a plurality of portable tool units which, in order to carry out a treatment process, can be supplied to a treatment station for treating a reactant which, in particular, is at the same time a storage space for storing the reactant, and can be temporarily stored there.

71. The production system according to sentence 70, characterized in that one or more portable tool units of the tool system can be supplied to a tool storage space and/or to a treatment station and/or to a set-up station by means of a storage transport device, in particular one or more storage transport units, of the production system.

72. The production system according to one of sentences 1 to 71, characterized in that one or more tool units are designed and set up by means of the handling device for carrying out a treatment process and/or a maintenance process.

73. The production system according to one of sentences 1 to 72, characterized in that one or more tool units are designed and set up independently of the handling device, in particular automatically, for carrying out a treatment process and/or a maintenance process.

74. The production system according to one of sentences 1 to 73, characterized in that the production system comprises an in particular fully automatic tool system which comprises one or more tool units for carrying out treatment processes on a reactant, wherein the tool system is arranged within the clean room region.

75. The production system according to one of sentences 61 to 74, characterized in that the tool system comprises one or more tool units designed as a fluid conveying device, by means of which a fluid can be conveyed in particular to be adjustable with respect to a volume flow.

76. The production system according to one of sentences 61 to 75, characterized in that the tool system comprises one or more tool units designed as a micro-fluid conveying device, by means of which a fluid can be conveyed in particular to be adjustable with respect to a volume flow, in particular for aliquoting.

77. The production system according to one of sentences 61 to 76, characterized in that the tool system comprises one or more tool units designed as a device for dividing a fluid, by means of which the fluid can be conveyed in particular adjustably with respect to a volume flow and by means of which the fluid can be divided in particular into at least two fluid parts.

78. The production system according to one of sentences 61 to 77, characterized in that the tool system comprises one or more tool units designed as a fluid mixing device by means of which a fluid can be mixed.

79. The production system according to one of sentences 61 to 78, characterized in that the tool system comprises one or more tool units designed as a mixing device, by means of which at least two components are miscible with one another, wherein in particular one of the at least two components is a fluid.

80. The production system according to one of sentences 61 to 79, characterized in that the tool system comprises one or more tool units designed as a measuring device, by means of which at least one property of a fluid and/or of one reactant can be measured.

81. The production system according to one of sentences 61 to 80, characterized in that the tool system comprises one or more tool units designed as a material separation device, by means of which a starting component can be separated into at least two components.

82. The production system according to one of sentences 61 to 81, characterized in that the tool system comprises one or more tool units designed as a heating device, by means of which a fluid can be temperature-controlled.

83. The production system according to one of sentences 61 to 82, characterized in that the tool system comprises one or more tool units designed as a device for supplying and/or discharging a gas, by means of which a gas can be supplied and/or discharged.

84. The production system according to one of sentences 61 to 83, characterized in that the tool system comprises one or more tool units designed as a manipulator, by means of which a cell membrane can be manipulated, in particular by means of an electrical field.

85. The production system according to one of sentences 61 to 84, characterized in that the tool system comprises one or more tool units designed as a radiation source and/or a light emitting device, wherein the radiation source is configured to emit ionized radiation, and the light emitting device is configured to emit light at a predetermined wavelength.

86. The production system according to one of sentences 61 to 85, characterized in that the tool system comprises one or more tool units designed as a cleaning device, by means of which a location at which the treatment processes can be carried out at the reactant by means of the one or more tool units can be cleaned and/or sterilized.

87. The production system according to one of sentences 1 to 86, characterized in that the production system comprises a tool system and a supply device for supplying the tool system with consumable materials.

88. The production system according to sentence 87, characterized in that the supply device comprises or uses one or more storage spaces of the storage device arranged within the clean room region for storing consumable materials.

89. The production system according to sentence 87 or 88, characterized in that the airlock device forms a component of the supply device or interacts therewith, wherein consumable materials can be introduced into the clean room region by means of the airlock device.

90. The production system according to one of sentences 87 to 89, characterized in that the storage device forms a component of the supply device or interacts therewith.

91. The production system according to one of sentences 87 to 90, characterized in that, by means of a storage transport device of the storage device, in particular by means of one or more storage transport units of the storage transport device of the storage device, consumable materials supplied from the surroundings of the production system can be supplied to one or more storage spaces of the storage device.

92. The production system according to one of sentences 61 to 91, characterized in that, by means of a storage transport device of the storage device, in particular by means of one or more storage transport units of the storage transport device of the storage device, consumable materials can be supplied to the tool system, in particular one or more tool units of the tool system, for example for supplying consumable substances and/or tool consumables to one or more tool units of the tool system.

93. The production system according to one of sentences 87 to 92, characterized in that the supply device comprises one or more disposal units, by means of which in particular used, spent and/or contaminated consumable substances and/or tool consumables can be removed from the clean room region.

94. The production system according to one of sentences 87 to 93, characterized in that the supply device comprises a refilling device arranged within the clean room region, by means of which filling device, consumable substances in particular present in liquid form, can be supplied to one or more storage devices of one or more workpiece carriers and/or one or more storage spaces.

95. The production system according to one of sentences 1 to 94, characterized in that the production system comprises one or more sensor units for determining one or more values of one or more parameters of a) one or more reactants; and/or b) one or more workpiece carriers; and/or c) one or more tools; and/or d) one or more receiving boxes, in particular receiving boxes designed as aseptic process units.

96. The production system according to one of sentences 1 to 95, characterized in that an occupancy state of one or more storage spaces of a storage device of the production system can be determined, in particular monitored, by means of one or more sensor units.

97. The production system according to one of sentences 1 to 96, characterized in that a local temperature and/or a local humidity and/or a local illumination or irradiance can be determined, in particular monitored, at or in one or more storage spaces of the storage device of the production system by means of one or more sensor units.

98. The production system according to one of sentences 1 to 97, characterized in that the production system comprises one or more sensor units for determining a progress of treatment during the treatment of a reactant or between two treatment processes.

99. The production system according to one of sentences 1 to 98, characterized in that one or more sensor units for determining the progress of treatment are microscopy devices for visually capturing microscopic components of the reactant.

100. The production system according to one of sentences 1 to 99, characterized in that one or more sensor units for determining the treatment progress are arranged in each case at or in one or more storage spaces, in particular integrated therein, for receiving reactants.

101. The production system according to one of sentences 1 to 100, characterized in that the production system, in particular one or more tools, for carrying out one or more treatment processes can be controlled on the basis of open-loop and/or closed-loop control, depending on the one or more determined values, wherein one or more treatment parameters are varied in particular depending on a determined treatment progress.

102. The production system according to one of sentences 1 to 101, characterized in that the production system comprises one or more sensor units for monitoring a quantity of consumable materials stored within the clean room region.

103. A method for producing a product, in particular a biological-pharmaceutical product, by means of a production system, in particular a production system according to one of sentences 1 to 102, the method comprising the following:

selecting one of a plurality of production programs for producing one of a plurality of products producible by means of the production system;

introducing a reactant into a airlock device of the production system;

automatically transporting the reactant into a clean room region of the production system;

automatically carrying out one or more treatment processes on the reactant.

104. The method according to sentence 103, characterized in that the reactant is stored in a storage space of a storage device of the production system located within the clean room region when the reactant is automatically transported into the clean room region of the production system.

105. The method according to sentence 104, characterized in that one or more treatment processes are carried out fully automatically until a product to be produced from the reactant is completed.

106. The method according to sentence 104 or 105, characterized in that one or more, in particular all, treatment processes are carried out at the storage space.

107. The method according to one of sentences 104 to 106, characterized in that the product produced in this way is removed from the storage space and transported automatically to the airlock device for removal of same from the production system.

108. The method according to sentence 107, characterized in that the product is filled and/or packaged before it is removed, in particular filled and/or packaged ready for use.

109. The method according to one of sentences 104 to 108, characterized in that one or more vessels, receptacles and/or tools which have been used to produce the product remain at least partially within the clean room region after completion of the product, are cleaned and are then reused for producing a further product.

110. The method according to one of sentences 104 to 109, characterized in that necessary consumable materials, in particular consumable substances and/or tool consumables, are stored within the clean room region in order to produce the product and/or to produce a plurality of different products, in particular before a selection of the product to be produced is made.

111. The method according to sentence 110, characterized in that the consumable materials are automatically transported into the clean room region via the airlock device and are stored there in particular in one or more storage spaces of the storage device.

112. The method according to sentence 110 or 111, characterized in that a quantity of the consumable materials stored within the clean room region is monitored, and in that, when a predetermined minimum amount is undershot, the supply is increased by supplying the required consumable materials, in particular via an indication or a warning message at an operator unit.

113. The method according to one of sentences 104 to 112, characterized in that a plurality of products, in particular a plurality of different products, are simultaneously produced within the clean room region.

114. The method according to sentence 103, characterized in that a sequence of treatment processes is associated with each product to be produced, which treatment processes are carried out by means of tools arranged within the clean room region and remain in the clean room region after the treatment processes have been carried out.

115. The method according to one of sentences 103 to 114, characterized in that one or more tools are cleaned, in particular sterilized, after one or more treatment processes have been carried out within the clean room region.

116. The method according to one of sentences 103 to 115, characterized in that one or more tools are equipped with tool consumables before one or more treatment processes are carried out within the clean room region.

117. The method according to sentence 116, characterized in that one or more tool consumables are removed from and/or disposed of by the one or more tools after one or more treatment processes within the clean room region are carried out.

118. The method according to one of sentences 103 to 117, characterized in that a plurality of, in particular all, treatment processes are associated with treatment time values which indicate that time period which elapses from a start of the corresponding treatment process up to its end, in particular including a time period for providing the at least one tool required for the corresponding treatment process, in particular including its equipping with one or more tool consumables, and/or a time period for the supply and/or arrangement and/or startup of the at least one tool on the reactant to be treated, in particular at a storage space at which the reactant is arranged, and/or a duration of the effect on the reactant in order to achieve a desired treatment result; and/or a time period for removing the at least one tool from the reactant, in particular from the storage space, preferably including a) a cleaning of the at least one tool; and/or
  b) a removal and/or disposal of tool consumables; and/or
  c) a return transport of the tool to a starting location, in particular a storage space associated with the tool.

119. The method according to one of sentences 103 to 118, characterized in that the treatment processes required for producing a specific product and the associated treatment time values are stored or taken into account in each production program.

120. The method according to one of sentences 103 to 119, characterized in that a prediction of a production sequence is created when a production program is started, and in that the tools required and/or provided for carrying out the treatment processes are reserved for time slots resulting from the prediction.

121. The method according to one of sentences 103 to 120, characterized in that for one or more treatment processes are or will be assigned in each case a) one or more cleaning processes for cleaning one or more tools and/or for cleaning one or more storage spaces; and/or b) one or more disposal processes for disposing of consumable materials; and/or c) one or more set-up processes for equipping one or more tools with consumable materials; and/or d) one or more control processes to control a treatment result, wherein, depending on the prediction of the production process, time slots are reserved at one or more of those devices that are required for carrying out the one or more cleaning processes, the one or more disposal processes, the one or more set-up processes, and/or the one or more control processes.

122. The method according to sentence 120 or 121, characterized in that, after one or more treatment processes, in particular after each treatment process, the prediction of the production sequence is checked and/or updated, in particular for confirming or correcting the time slots for the tools and/or other devices that are still required for completing the product.

123. The method according to one of sentences 103 to 122, characterized in that, at a desired start of a production program, it is determined on the basis of a prediction of the production sequence whether all required tools and/or other devices for finishing the product are available within the required time slots, and in that the production program is only started if this determination has supplied a positive result.

Further preferred features and/or advantages of the present invention form the subject matter of the following description and the drawings illustrating exemplary embodiments.

The same or functionally equivalent elements are provided with the same reference signs in all figures.

DETAILED DESCRIPTION OF THE DRAWINGS

Figure 1:
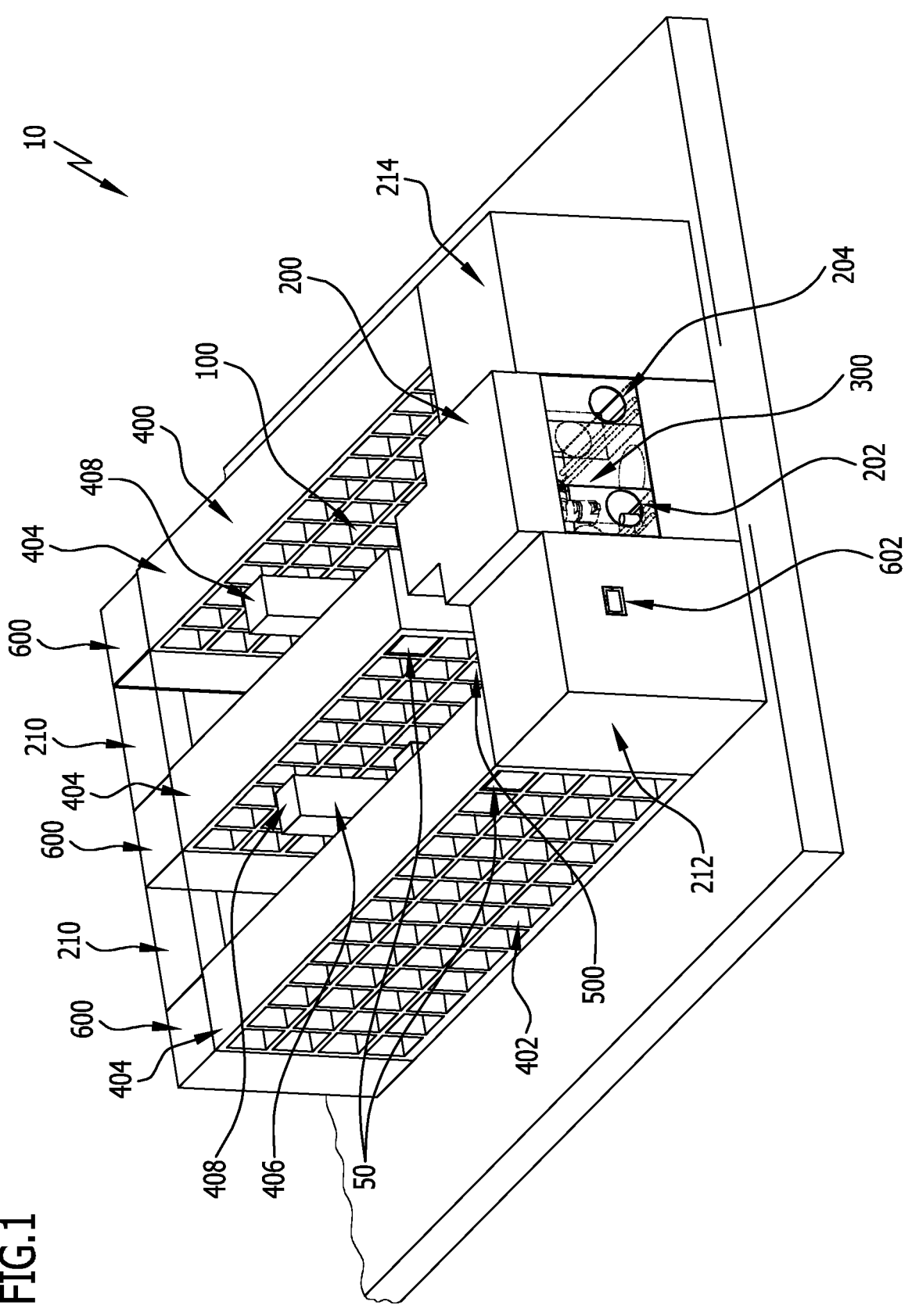
FIG. 1 is a schematic perspective view of a production system according to an exemplary embodiment of the present invention.

In FIG. 1 a schematic perspective view of a production system 10 according to an exemplary embodiment of the present invention is shown.

Referring to FIG. 1, a production system 10 in particular for producing biological-pharmaceutical products 20 comprises:

a clean room region 100;

an airlock device 200 for supplying an object from the surroundings of the production system 10 into the clean room region 100 and/or for removing an object from the clean room region 100;

a handling device 300 for moving the object within the clean room region 100; and a storage device 400 which is arranged within the clean room region and which comprises a plurality of storage spaces 402 for receiving a plurality of objects.

The biological-pharmaceutical product 20 can be intended for a personalized therapy and can consequently be a personalized therapeutic agent, for example a personalized cell therapeutic agent, for example an autologous and/or an allogeneic cell therapeutic agent, or a gene therapeutic agent, for example an autologous and/or an allogeneic gene therapeutic agent.

The production system 10 has a housing (not shown in the figures) for delimiting the clean room region 100 with respect to the surroundings of the production system 10.

To a certain extent, the housing surrounds the entire production system 10.

The airlock device 200 is therefore configured to supply an object from the surroundings of the production system 10 via the or through the housing into the clean room region 100 and/or to remove an object from the clean room region 100 via the or through the housing.

By means of a system for setting the ambient properties of the clean room region 100 of the production system 10 (not shown in the figures), the clean room region 100 can be subjected to an positive pressure in order to ensure predetermined clean room properties of the clean room region 100, in particular to avoid the ingress of contamination substances.

Furthermore, an air supply and an air discharge into and out of the clean room region 100 take place by means of the system for setting the ambient properties of the clean room region 100.

As can be seen in FIG. 1, the storage device 400 comprises a plurality of storage racks 404, here three, for example, which each have a plurality of storage spaces 402.

To a certain extent, the storage spaces 402 are rack spaces of one or more, for example three, storage racks 404.

The storage device 400 further comprises a storage transport device 406 for transporting objects to the storage spaces 402, in particular the storage racks 404, and/or from the storage spaces 402, in particular the storage racks 404.

In particular, reactants and/or workpiece carriers and/or tools or tool units and/or consumable materials can be stored in and/or removed from the storage spaces 402 of the storage racks 404 by means of the storage transport device 406 of the storage device 400.

The storage transport device 406 is a device different from the handling device 300.

The storage transport device 406 is a rail-guided transport system and comprises one or more rail-guided storage transport units 408, here by way of example two, by means of which the storage racks 404 of the storage device 400 are accessible, in particular for storage and retrieval processes, and for treatment processes and/or maintenance processes.

The storage racks 404 are arranged substantially parallel to one another and in each case at a distance from one another in the clean room region 100.

The storage transport device 406 is arranged at the corresponding distances of the storage racks 404, wherein a storage transport unit 408 is associated with a corresponding distance between the storage racks 404.

A storage rack-storage transport unit-storage rack-storage transport unit-storage rack arrangement is currently present.

This arrangement makes it possible for at least the storage spaces 402 of the central storage rack 404 to be accessible from a plurality of directions and/or by means of both storage transport units 408 of the storage transport device 406.

Other arrangements of the storage racks 404 in combination with the storage transport units 408 are also conceivable in the present case.

The parallel arrangement described above can be expanded or realized in its alternating manner, for example, as required.

Furthermore, a star-shaped arrangement of the storage racks 404 can also be conceivable, for example.

The storage spaces 402 of the storage racks 404 are accessible laterally in the horizontal direction by means of the storage transport device 406.

A plurality of substantially horizontally aligned rows of storage spaces 402 are arranged superimposed in the vertical direction in the storage racks 404.

To a certain extent, the storage spaces 402 in the storage racks 404 are arranged in a matrix-like manner; for example, in FIG. 1 matrix-like arrangements of 4×13 (external storage racks 404) and 4×10 (central storage rack 404) are shown.

As already described, the storage spaces 402 are configured to receive different types of objects, wherein the storage spaces 402 can differ from one another with regard to their shape and/or dimensioning.

For simplified view, the storage spaces 402 are in FIG. 1 only shown by way of example in a uniform manner, in particular a uniform shape and dimensioning.

The storage spaces 402 can furthermore differ from one another with regard to their function and/or their equipment.

The different types of storage spaces can be arranged in a regular pattern distributed in a storage space rack and/or a storage space area of the storage device.

The production system 10 further comprises a cleaning device 500 by means of which one or more workpiece carriers 30 and/or one or more tools or tool units 702 and/or one or more consumable materials 704 can be cleaned and/or sterilized.

The cleaning device 500 is designed as a separate device in the clean room region and as a component of a tool system, in particular of a tool or a tool unit 702.

By means of the cleaning device 500, objects, in particular tools 702 and/or consumable materials 704, coming in particular into direct contact with reactants can be cleaned and/or sterilized, in particular by means of irradiation.

By means of the cleaning device 500, in particular objects which are not in direct contact with reactants can be cleaned and/or disinfected or sterilized, in particular by means of gassing.

The production system 10 also comprises an unpacking device 212 for unpacking objects to be supplied to the clean room region 100, and a packaging device 214 for packaging the objects to be removed from the clean room region 100, for example for packaging the product 20 produced.

The unpacking device 212 and the packaging device 214 are integrated or incorporated in the airlock device 200, in particular integrated or incorporated laterally in the present case.

Figure 2:
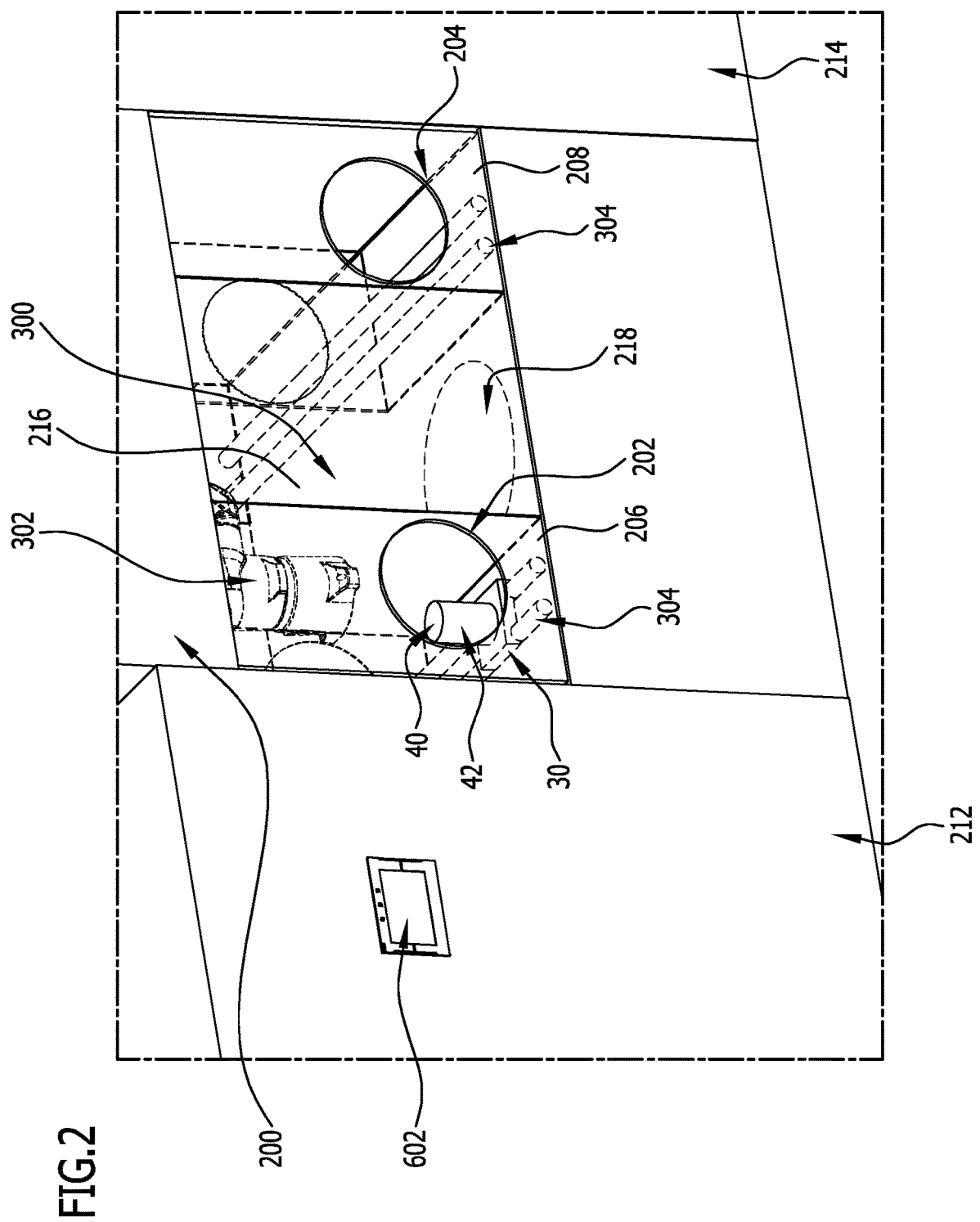
FIG. 2 is a schematic perspective view of part of the production system shown in FIG. 1.

As shown in FIGS. 1 and 2, the airlock device 200 has an inlet airlock 202 via which an airlock space 206, in particular an inlet airlock space 206, is accessible from the surroundings and which is configured to supply an object from the surroundings of the production system 10 into the clean room region 100.

As further shown in FIGS. 1 and 2, the airlock device 200 has an outlet airlock 204 via which an airlock space 208, in particular an outlet airlock space 208, is accessible from the surroundings and which is configured to remove an object from the clean room region 100.

The inlet airlock 202 and the outlet airlock 204 furthermore comprise means for in particular spatially isolating the airlock spaces 206, 208 (not shown in the figures) associated in each case with the inlet airlock 202 and the outlet airlock 204.

An isolation can optionally be carried out with respect to the surroundings of the production system 10 and/or to a corresponding part of the airlock device 200 that is different from the airlock spaces 206, 208, in each case by means of the respective means for isolating from the entry airlock 202 and from the outlet airlock 204.

Furthermore, the production system 10 has a plurality of maintenance airlocks 210, via which the clean room region 100 is accessible from the surroundings of the production system 10, for example, for users, in particular for maintenance work within the clean room region 100.

The production system 10 has one or more control units which are set up within the clean room region 100 in a control system 600 arranged in control cabinets and which are designed and programmed to provide closed-loop and/or open-loop control of at least one component comprised by the production system or a component of the production system, which component is associated with the one or more control units.

It is conceivable that one or more control units form a higher-level control device.

The one or more control units are designed and programmed to be able to communicate with one or more communication interfaces (not shown in the figures) and/or one or more human-machine interfaces, for short: HMI interfaces, 602 of the production system 10 (an HMI interface 602 is shown in the figures by way of example).

The communication interfaces not shown in the figures can serve, for example, to ensure a data exchange with a higher-level control system and/or data management system, for example an associated cloud system, in order, for example, to enable data evaluation and/or data optimization via artificial intelligence and/or deep learning.

The one or more control units are further designed and programmed to provide information to a user via the communication interfaces and/or via the HMI interfaces 602, for example fault information and/or information about a state of a production of a product 20 and/or information about inventory stocks of the storage device 400.

Furthermore, the production of the biological-pharmaceutical product 20 can be carried out by means of the production system 10 by means of the one or more control units.

The aforementioned product production according to one or more production programs can be carried out by means of the one or more control units.

A sequence of treatment processes, which can be carried out by means of tool units 702 arranged within the clean room region 100 and remaining in the clean room region after the treatment processes have been carried out, is associated with each product 20 to be produced.

In each production program, the treatment processes required for the production of a specific product 20 and associated treatment time values are stored or taken into account.

The production system 10 further comprises one or more sensor units for determining one or more values of one or more parameters of one or more reactants 40, and/or one or more workpiece carriers 30, and/or one or more tools or tool units 702 and/or one or more consumable materials 704.

The sensor units are connectable or connected to the control units.

The sensor units serve in particular to determine a treatment progress during the treatment of a reactant or between two treatment processes.

The sensor units serve in particular to provide open-loop and/or closed-loop control of one or more tool units 702 for carrying out one or more treatment processes depending on the one or more determined values, wherein one or more treatment parameters are varied or can be changed in particular depending on a determined treatment progress.

The sensor units serve in particular for monitoring the storage device 400, for example storage states and/or storage quantities at the storage spaces 402.

The production system 10 is furthermore connected to at least one electrical power source (not shown in the figures), which is arranged in the surroundings of the production system, for a power supply.

In FIG. 2, an enlarged view is shown in particular of the airlock device 200 from FIG. 1.

Figure 3:
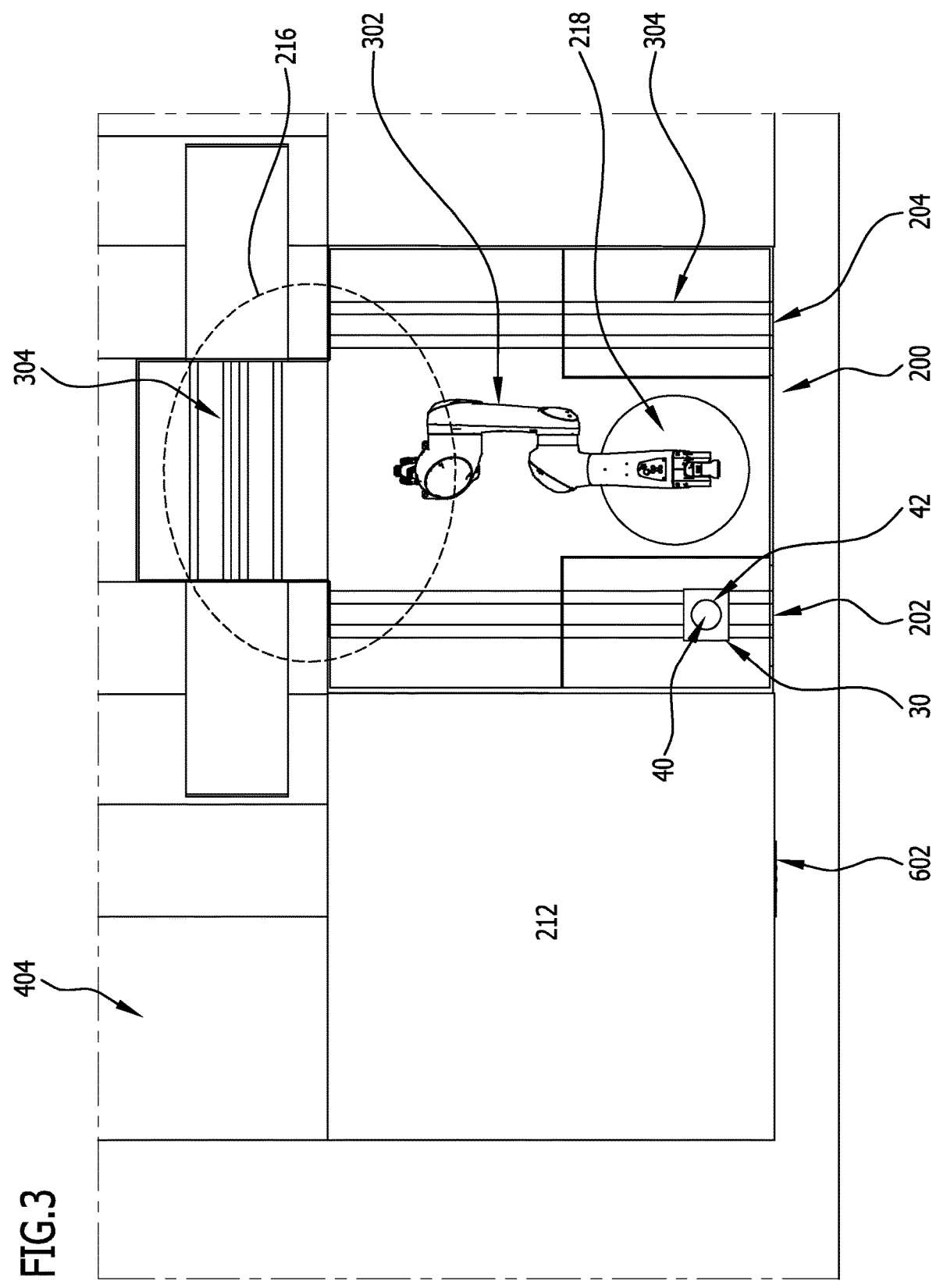
FIG. 3 is a schematic plan view of part of the production system shown in FIG. 1.

Referring to FIGS. 2 and 3, the handling device 300 comprises a multi-axis robot arm 302, which is arranged adjacent to the airlock device 200, and an airlock transport device 304, by means of which one or more objects can be transported from an airlock space, in particular an inlet airlock space 206, to a further airlock space, in particular a transfer airlock space 216, and/or from an airlock space, in particular a transfer airlock space, to a further airlock space, in particular an outlet airlock space 208.

It is also conceivable that the handling device 300 has a first multi-axis robot arm and a second multi-axis robot arm (not shown in the figures), wherein the first multi-axis robot arm is assigned to an inlet material flow into the production system and the second multi-axis robot arm is assigned to a reactant flow from the production system. It can also be conceivable that the handling device 300 can be subdivided into a first handling device and a second handling device, which can in each case be assigned to an inlet material flow into the production system and an exit material flow from the production system.

A workpiece carrier 30 of the production system 10 and a reactant 40, which is accommodated in a reactant container 42, is arranged in the inlet airlock 202 on the inlet airlock space 206, wherein the reactant container 42 is arranged on the workpiece carrier 30.

The workpiece carrier 30 is arranged on the airlock transport device 304.

The reactant 40 has cells and a culture medium, wherein the cells and the culture medium form a cell suspension.

The cell suspension is present with a volume between 1 μl and 1000 ml.

In addition to said workpiece carrier 30, the production system 10 has one or more further workpiece carriers 30 which are storable or stored, for example, in the storage spaces 402.

The workpiece carriers 30 serve to receive reactants and/or tools or tool units and/or consumable materials.

The workpiece carrier(s) 30 has a means for fixing, in particular an means for form-fitting and/or force-fitting and/or magnetic fixing, not shown in the figures, for receiving reactants and/or tools and/or consumable materials.

The fixing means can in particular comprise at least one adapter device and/or at least one mold cavity device, in particular in order to create a secure receiving connection between a workpiece carrier and a reactant container.

The fixing means can in particular be designed individually to correspond to the objects to be received, such as, for example, the reactant container.

The workpiece carrier 30 shown in FIGS. 1 and 2 in the present case has received a reactant 40 arranged in a reactant container 42.

The production system 10 comprises a plurality of types of workpiece carriers 30 which differ from one another with regard to the shape and/or dimensioning of a receiving region of the corresponding workpiece carrier 30.

As shown by way of example in FIGS. 1 and 2, one type of workpiece carriers 30 serves to receive a reactant container 42.

Another type of workpiece carriers 30 serves to receive one or more tool units 702 and/or tool consumables 704 for carrying out a treatment process on a, or the, reactant 40 and/or for carrying out a maintenance process within the clean room region 100.

Another type of workpiece carriers 30 serves to receive consumable materials 704 for feeding same to a, or the, reactant 40 and/or to carry out a treatment process on a, or the, reactant 40.

One or more workpiece carriers 30 each comprise one or more action units (not shown in the figures) for carrying out an action on a, or the, reactant 40 and/or on a tool 702, wherein one or more action units are designed as a treatment unit, for example as a tool unit 702, for carrying out a treatment process on the reactant 40, and/or one or more action units are designed as a sensor unit for determining a current value of a parameter of the corresponding workpiece carrier 30 and/or of a reactant 40 arranged thereon and/or of a tool 702 arranged thereon and/or of the consumable materials 704 arranged thereon. As a result, functions of the in particular independent tool system (see above description) can be taken over in a functional unit, here the workpiece carrier 30.

One or more workpiece carriers 30 comprise a storage device (not shown in the figures) for storing energy and/or one or more consumable materials 704, wherein the workpiece carriers 30 are reusable several times, in particular the storage device is electrically rechargeable and/or can be refilled with consumable material 704.

The workpiece carrier(s) 30 have/has one or more coupling devices (not shown in the figures) by means of which a plurality of, in particular two or more, workpiece carriers 30 can be connected to one another.

The workpiece carrier 30 arranged on the airlock transport device 304 and shown in FIGS. 1 and 2 was supplied to the inlet airlock space 206 for receiving the reactant container 42 in a process not shown in the figures.

In this case, a user has first selected a production program of the production system 10, for example via the HMI interface 602, in order to produce the desired product 20 from the reactant 40.

The user then places the reactant container 42 with a reactant 40 arranged therein onto a workpiece carrier 30 provided at the inlet airlock space 206, which workpiece carrier was already provided to the inlet airlock space 206 for receiving an object.

Alternatively, it is also conceivable that a workpiece carrier 30 stored at a storage space 402 of one of the storage racks 404 was removed from the storage space 402 by means of the storage transport unit 408 of the storage transport device 406 and has been transported to the airlock device 200, so that the workpiece carrier 30 can be supplied to the inlet airlock space 206 by means of the multi-axis robot arm 302 and the airlock transport device 304.

As soon as the workpiece carrier 30 is provided at the inlet airlock space 206 for receiving the reactant 40, the reactant container 42 with a reactant 40 arranged therein is manually transferred by the user to the workpiece carrier 30 and fixed thereto by means of the fixing means.

The reactant container 42 generally also has a packaging for maintaining an aseptic state of the reactant 30.

The entry airlock 202 can now be transferred into a closed state or is now closed.

A cleaning and sterilization process is now carried out on the packaged reactant container 42 at the inlet airlock space 206 by means of gassing and/or irradiation by means of a gassing source and/or irradiation source (not shown in the figures) which is correspondingly set up at the inlet airlock space 206.

Subsequently, the packaged reactant container 42 on the workpiece carrier 30 is moved into a range of the multi-axis robot arm 302 by means of the airlock transport device 304.

The multi-axis robot arm 302 separates the packaged reactant container 42 from the workpiece carrier 30 and transfers the reactant container 42 to the unpacking device 212, in which the packaging of the reactant container 42 is removable/is removed by means of one or more unpacking units of the unpacking device 212.

It is also conceivable here that the inlet airlock space 208 shown in FIGS. 2 and 3 serves as an unpacking space 206 and is accessible by means of one or more unpacking units of the unpacking device 212.

It is also conceivable that the packaging of the reactant container 42 can be removed by the multi-axis robot arm 302 by means of one or more unpacking units.

Figure 4:
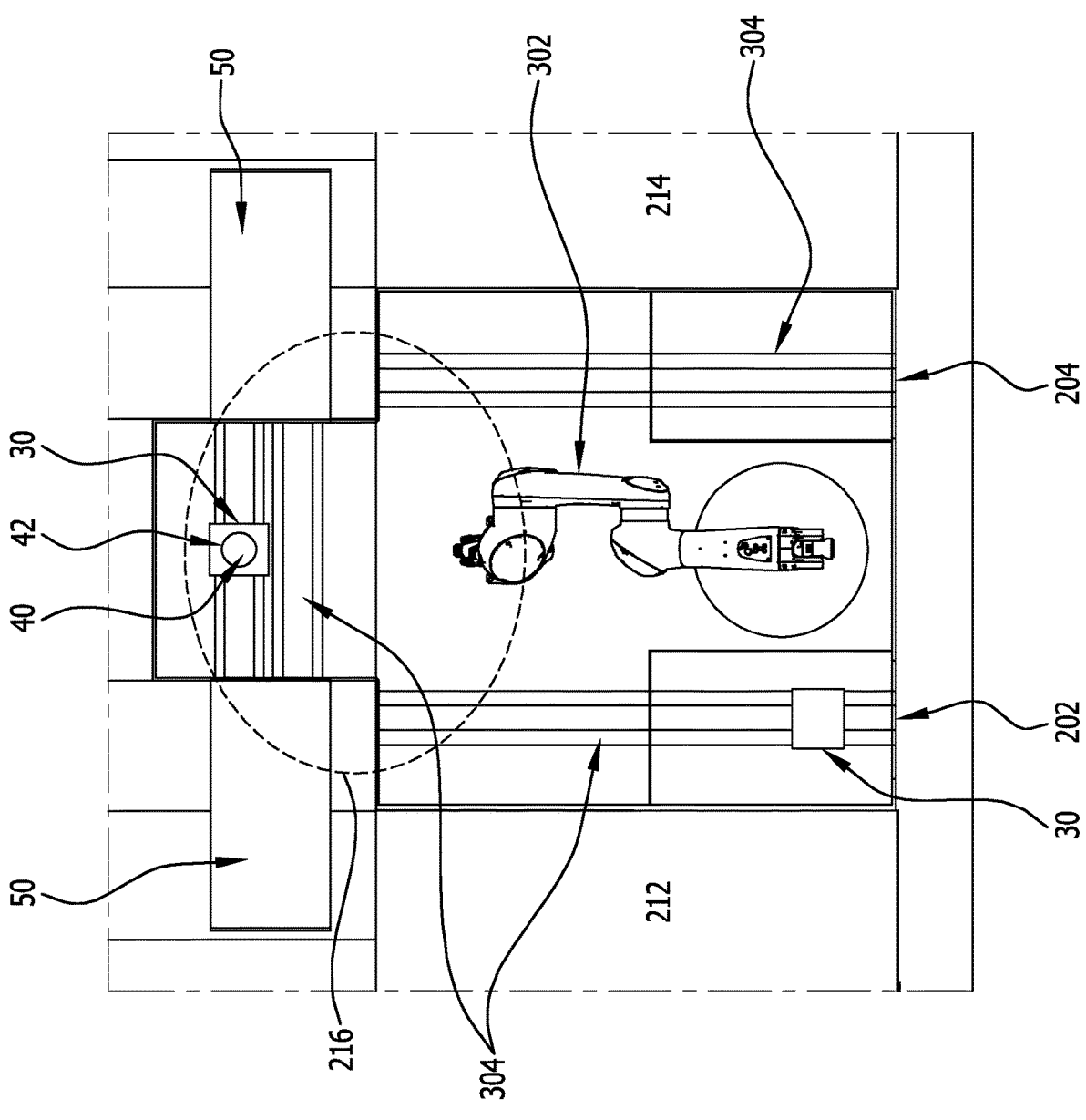
FIG. 4 is a schematic plan view of part of the production system shown in FIG. 1.

After the packaged reactant container 42 has been transferred to the unpacking device 212, the workpiece carrier 30 is again moved back to the inlet airlock space 206 for a renewed receiving of an object by means of the airlock transport device 304, as is shown in particular in FIG. 4.

After unpacking by means of the unpacking device 212, the unpacked reactant container 42 is supplied to another, in particular sterile workpiece carrier 30, which is provided at the transfer airlock space or the transfer airlock spaces 216 on the airlock transport device 304 (cf. FIG. 4), by means of the multi-axis robot arm 302.

The other workpiece carrier 30 was previously retrieved from a storage space 402 of the storage racks 404 and was accordingly provided by means of the storage transport unit 408, the multi-axis robot arm 302 and the airlock transport device 304, as shown in FIG. 4.

Figure 5:
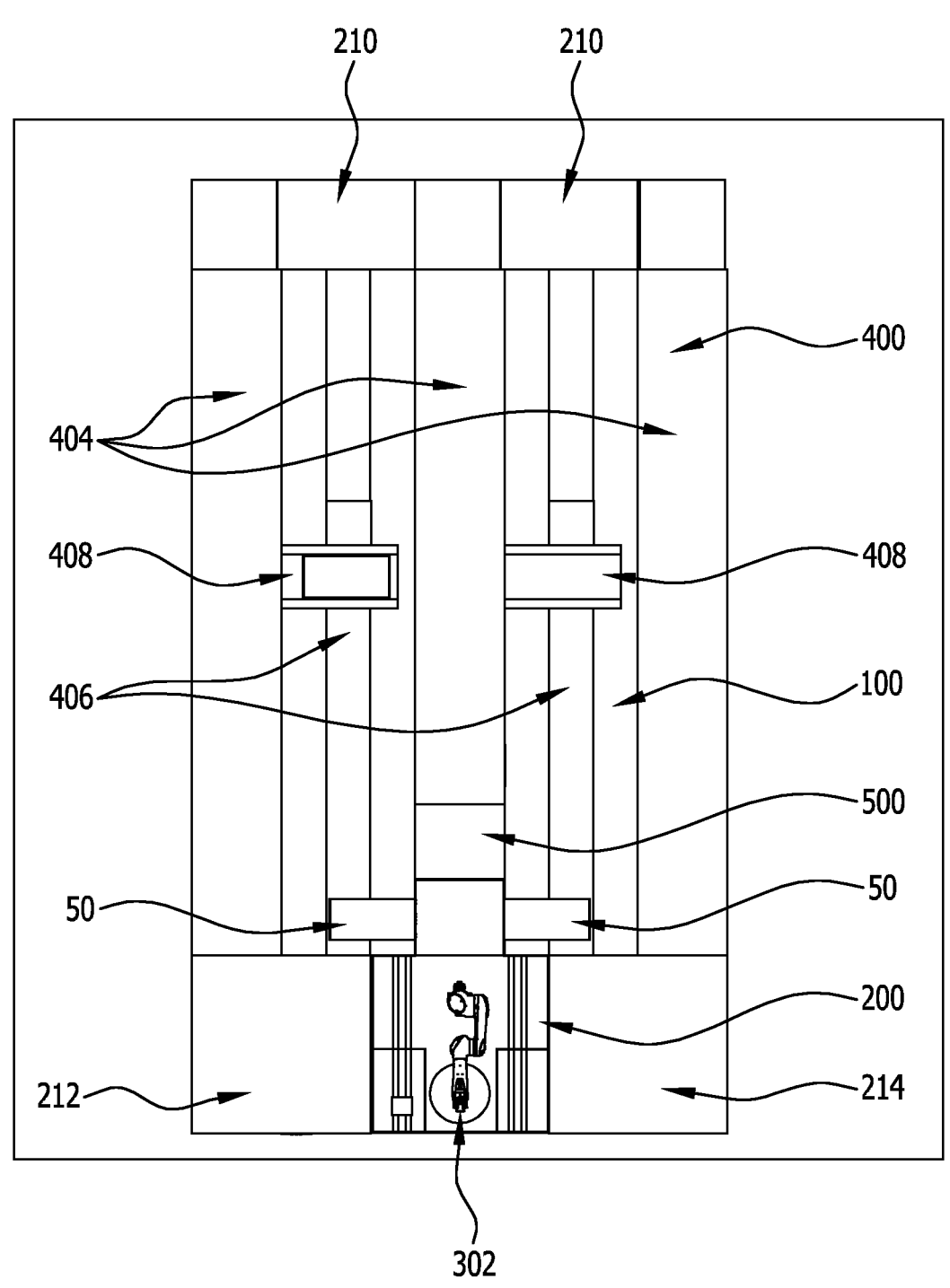
FIG. 5 is a schematic plan view of the production system shown in FIG. 1.

The airlock transport device 304 and/or the multi-axis robot arm 302 moves the workpiece carrier 30 together with the reactant container 42 arranged thereon into a receiving box 50 (the receiving box 50 shown on the left in FIGS. 3 to 5), which was provided by means of the storage transport unit 408 on the airlock transport device 304 (cf. FIGS. 3 to 5).

Furthermore, a further receiving box 50 is ready for receiving an object (the receiving box 50 shown on the right in FIGS. 3 to 5).

The production system 10 comprises a plurality of receiving boxes 50 for receiving one or more workpiece carriers 30 together with the reactants 40 arranged and/or received thereon, which are arranged in a reactant container 42.

It is also conceivable that, additionally or alternatively, a tool carrier 30 described above is designed as a receiving box 50.

As shown in FIG. 1, the receiving boxes 50 are storable in storage spaces 402 of the storage device 400, in particular fully automatically by means of the storage transport units 408.

One or more of the receiving boxes 50 surround a closable interior, which can define an aseptic process environment.

To a certain extent, a receiving box 50 defines a process unit, in particular an aseptic process unit.

The receiving boxes 50 can be opened and/or closed automatically and/or by means of the handling device 300 for introducing a reactant 40 and/or for removing a product 20 produced from a reactant 40.

The receiving boxes 50 each comprise one or more conditioning units (not shown in the figures) which are integrated or detachably arranged thereon or detachably arrangeable thereon, by means of which conditioning units a temperature and/or a pressure and/or a moisture and/or a gas composition in the interior of the corresponding receiving box 50 can be influenced, in particular can be subjected to open-loop and/or closed-loop control.

One or more of the conditioning units are tool units 702 of a tool system of the production system 10, which can be arranged on the corresponding receiving box 50 if necessary or can be removed therefrom, in particular fully automatically by means of the storage transport device 406, in particular the storage transport units 408 of the storage transport device 406, and/or by means of the handling device 300, in particular the multi-axis robot arm 302 of the handling device 300.

The receiving boxes 50 comprise one or more connection elements which can be connected to connection elements corresponding thereto on one or more storage spaces 402, in particular in order to supply the corresponding receiving box 50 with electrical energy and/or consumable materials 704, in particular liquids and/or gases, and/or to establish a signal-related coupling of the corresponding receiving box

50 with an in particular higher-level control device of the production system 10, for example one or more control units which serve as a higher-level control device.

For this purpose, the storage spaces 402 are provided with connection elements, so that one or more treatment processes for treating the reactants 40 can be carried out at storage spaces 402 of the storage device 400 serving as treatment stations.

The storage spaces 402 of the storage device 400 and/or the receiving boxes 50 comprise fixing elements by means of which the receiving boxes 50 can be positioned and/or fixed at the storage spaces 402.

The receiving boxes 50 each comprise one or more tool holders for receiving and fixing one or more tools or tool units 702, in particular in the interior of the corresponding receiving box 50.

The one or more tool holders can each comprise one or more connection elements which can be connected to connection elements corresponding thereto on the tool 702 to be received in each case, in particular in order to supply the corresponding tool 702 with electrical energy and/or consumable substances, in particular liquids and/or gases, and/or to establish a signal-technical coupling of the corresponding tool 702 to the receiving box 50 and/or the superordinate control device.

It is also conceivable for the receiving boxes 50 to comprise one or more connection elements which can be connected to connection elements corresponding thereto on a further receiving box 50, whereby an assembled receiving box 50 can be provided.

Referring to FIGS. 4 and 5 the workpiece carrier 30 together with the reactant container 42 arranged thereon was moved into the (left) receiving box 50 by means of the airlock transport device 304 and/or the multi-axis robot arm 302.

The receiving box 50 is now storable in the storage rack 404 shown on the left or in the middle in FIG. 5 by means of the left storage transport unit 408 shown in FIG. 5.

By means of said left storage transport unit 408, the receiving box 50 is transported to said central storage rack 404 and stored there.

Depending on the production program of the production system 10 selected by the user, by means of which the production system 10 is able to produce the desired product 20 from the reactant 40, one or more objects which are stored at the storage spaces 402 of the storage device 400, in particular tools or tool units 702 and/or consumable materials, are transportable by means of the storage transport units 408 in a defined sequence, which is specified by the selected production program, at defined points in time, which are specified by the selected production program, to the stored receiving box 50 with the reactant container 42 in the central storage rack 404 or are transported to this receiving box 50.

Figure 6:
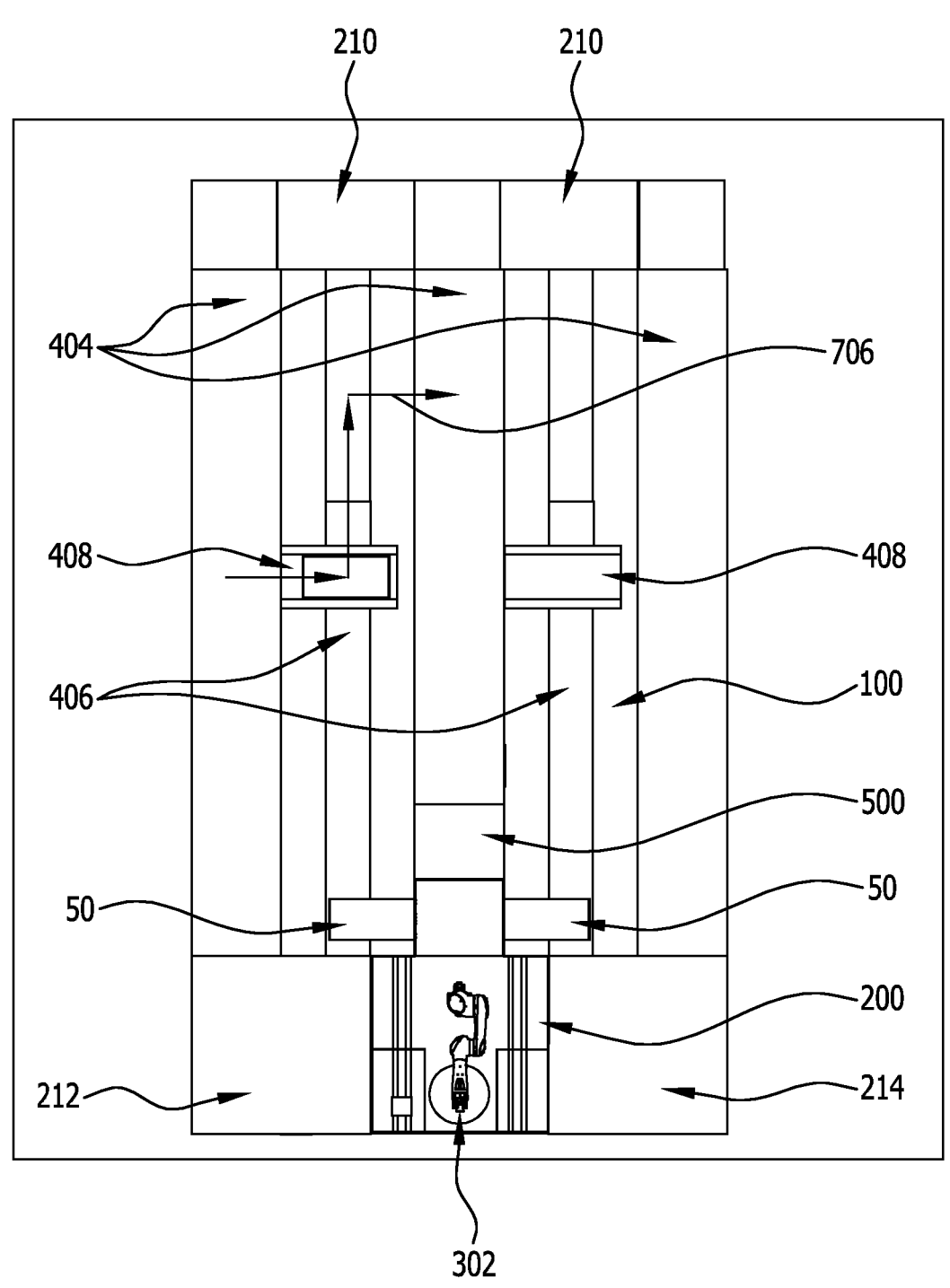
FIG. 6 is a schematic plan view of the production system shown in FIG. 1.

As shown by way of example in FIG. 6 by means of the arrows, for example, a tool unit 702 for carrying out one or more treatment processes from the left storage rack 404 is supplied to the reactant container 42 by means of the storage transport unit 408 and the receiving box 50 in order to carry out the one or more treatment processes on the reactant 40 in the reactant container 42 by means of the tool unit 702.

The arrows shown can represent a tool path 706 of the tool unit 702 within the clean room region 100.

The removed tool unit 702 is arranged here on a workpiece carrier 30 and/or in a receiving box 50.

The tool unit 702 is part of a tool system of the production system 10, by means of which treatment processes can be carried out at reactants and/or maintenance processes can be carried out within the clean room region 100.

The tool system comprises a plurality of fully automatic tool units 702 for carrying out different treatment and/or maintenance processes.

The tool system comprises one or more tool units 702 designed as supply units for supplying consumable materials 704 to the reactants 40 or the reactant 40.

The tool system comprises one or more tool units 702 designed as removal units for removing a sample from a, or the, reactant 40.

One or more of the tool units 702 of the tool system each comprise one or more multi-use components and/or one or more single-use components.

After carrying out the one or more treatment processes at the reactant 40, the previously supplied tool unit 702 is removed again by means of the storage transport unit 408 from the receiving box 50 which contains the reactant 40, in particular removed and transported away from or out of the receiving box 50.

This takes place in a receiving box 50.

Figure 7:
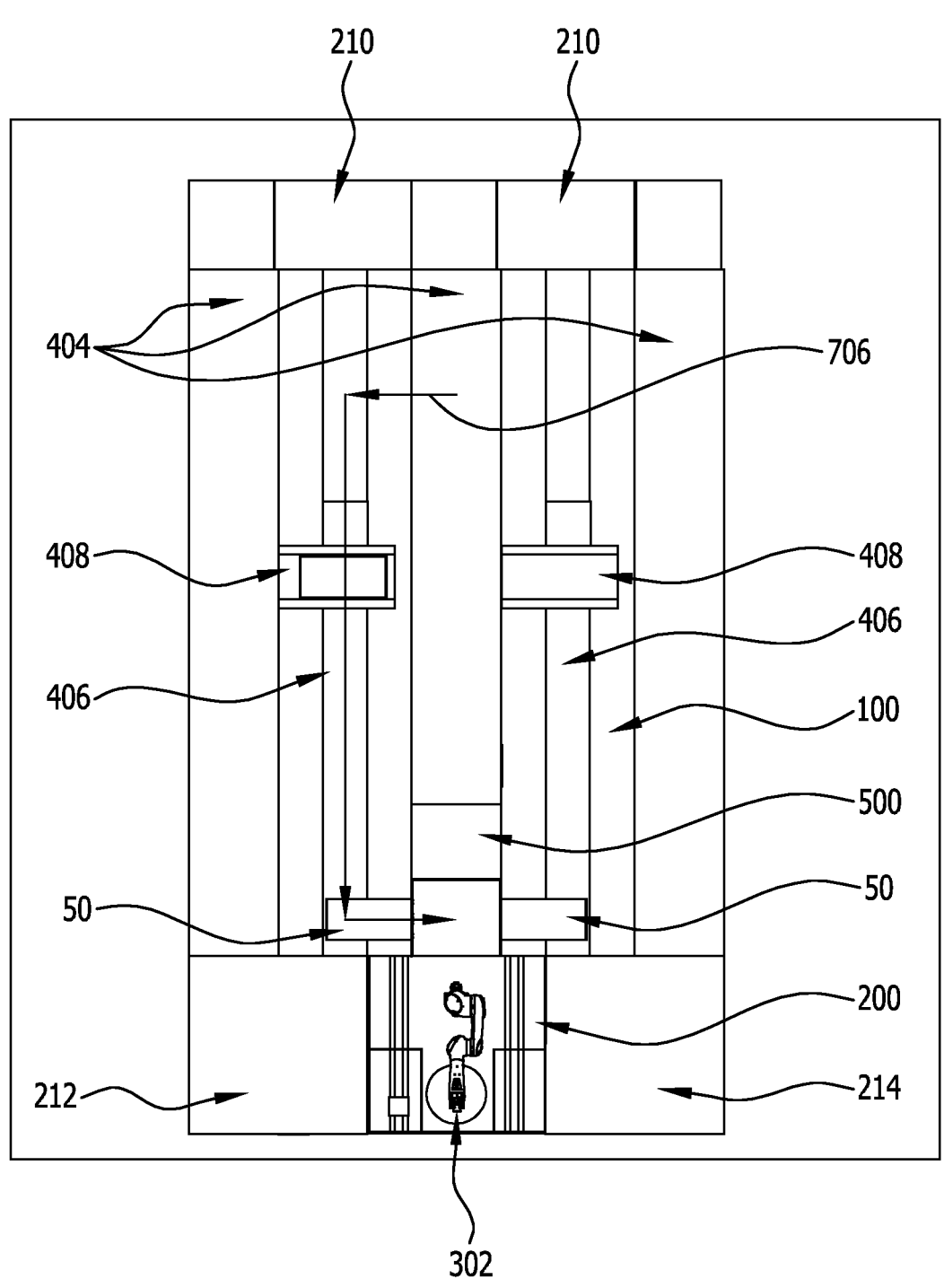
FIG. 7 is a schematic plan view of the production system shown in FIG. 1.
Figure 8:
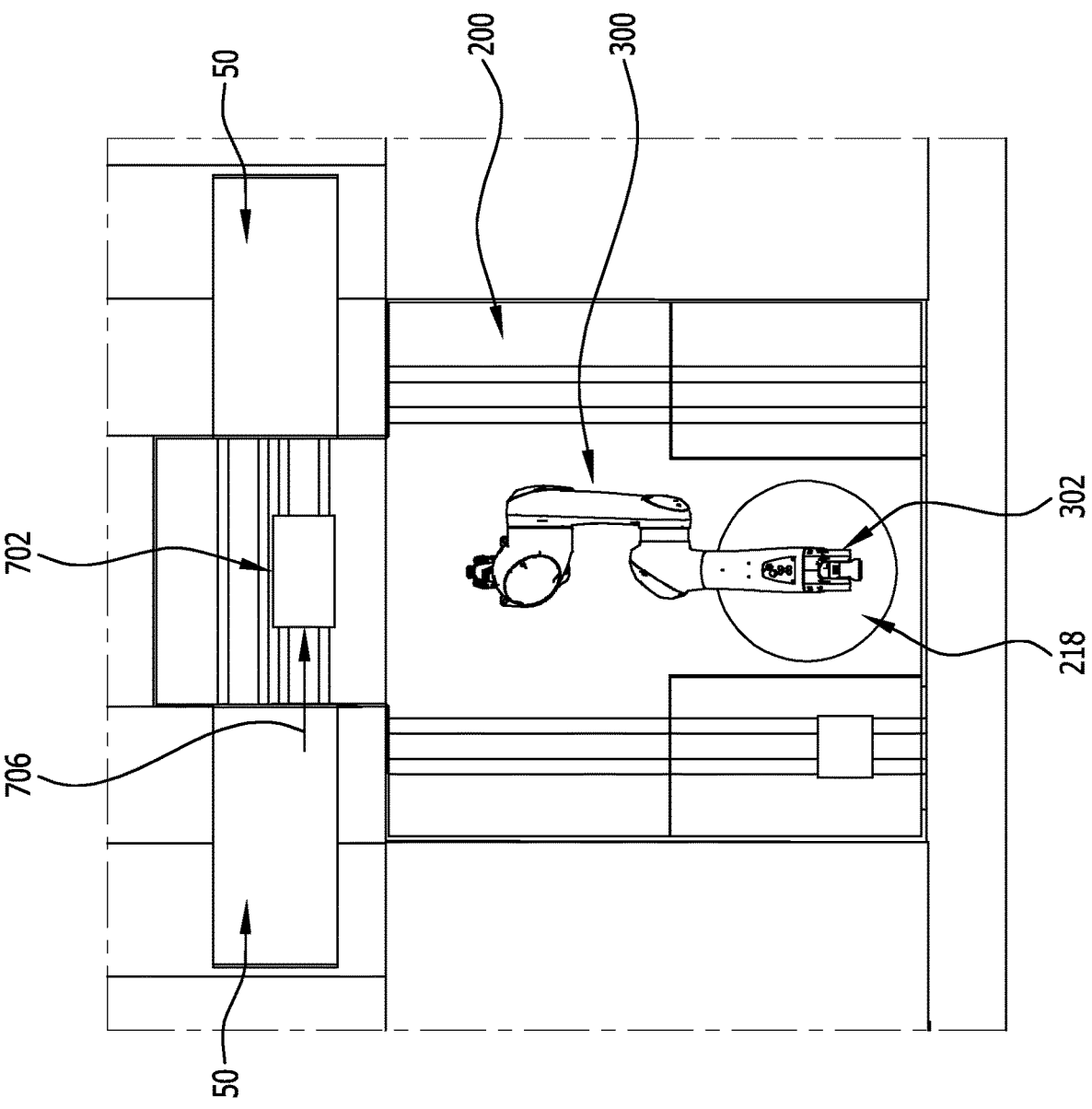
FIG. 8 is a schematic plan view of part of the production system shown in FIG. 1.

As shown in FIG. 7 by means of the arrows, the storage transport unit 408 transports the tool unit 702 used in this receiving box 50 to the handling device 300 in order to be removed there from the receiving box 50 by means of the handling device 300 (cf. FIG. 8).

The arrows shown can represent a tool path 706 of the tool unit 702 used within the clean room region 100. The tool path can be understood in the sense of a material flow, wherein in the present production system, in principle, a directed material flow, in particular a material flow directed from clean to dirty, is preferred.

By means of the handling device 300, in particular the multi-axis robot arm 302 of the handling device 300, the tool unit 702 used is separated from single-use components used in the one or more treatment processes and set up at the tool unit 702, such as, for example, hoses, cannulas and/or other disposable elements, wherein the remote single-use components are removable or removed from the clean room region 100 via the airlock device 200.

As shown schematically in FIG. 8 in particular, this takes place via a waste airlock 218 of the airlock device 200 by means of the multi-axis robot arm 302. It is conceivable that the waste airlock 218 is configured as a device separate from the handling device 300 in such a way that a clean-room-level separation is established between them in order to ensure a directed flow of material from clean to dirty.

Figure 9:
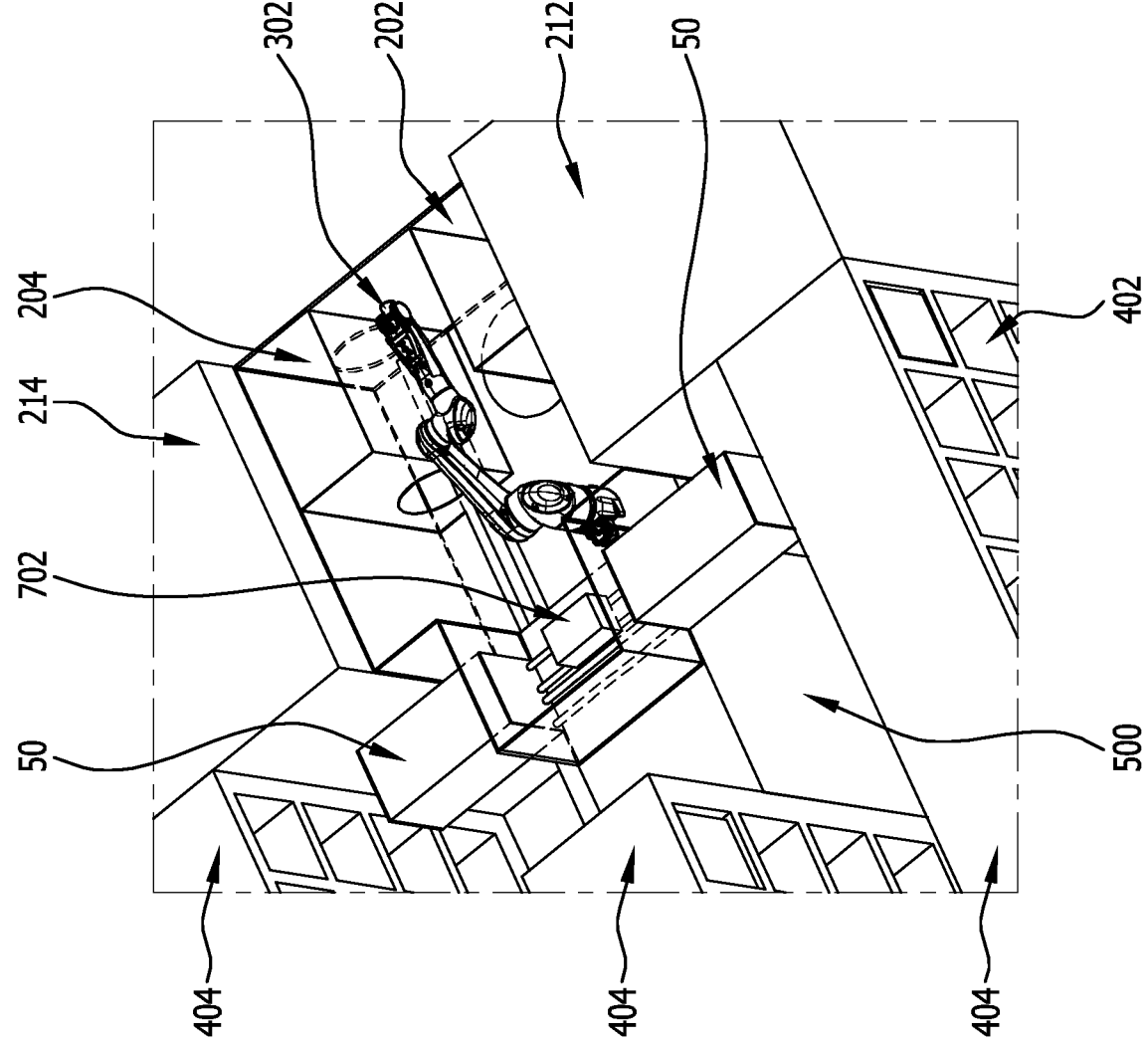
FIG. 9 is a schematic perspective view of part of the production system shown in FIG. 1.

Referring to FIG. 9, the tool unit 702 used is moved back into the receiving box 50 and subsequently supplied to the cleaning device 500 of the production system 10 together with the receiving box 50, in particular by means of the storage transport unit 408 and/or the handling device 300, by means of which the tool unit 702 used and its receiving box 50 are cleanable and sterilizable or cleaned and sterilized.

Figure 10:
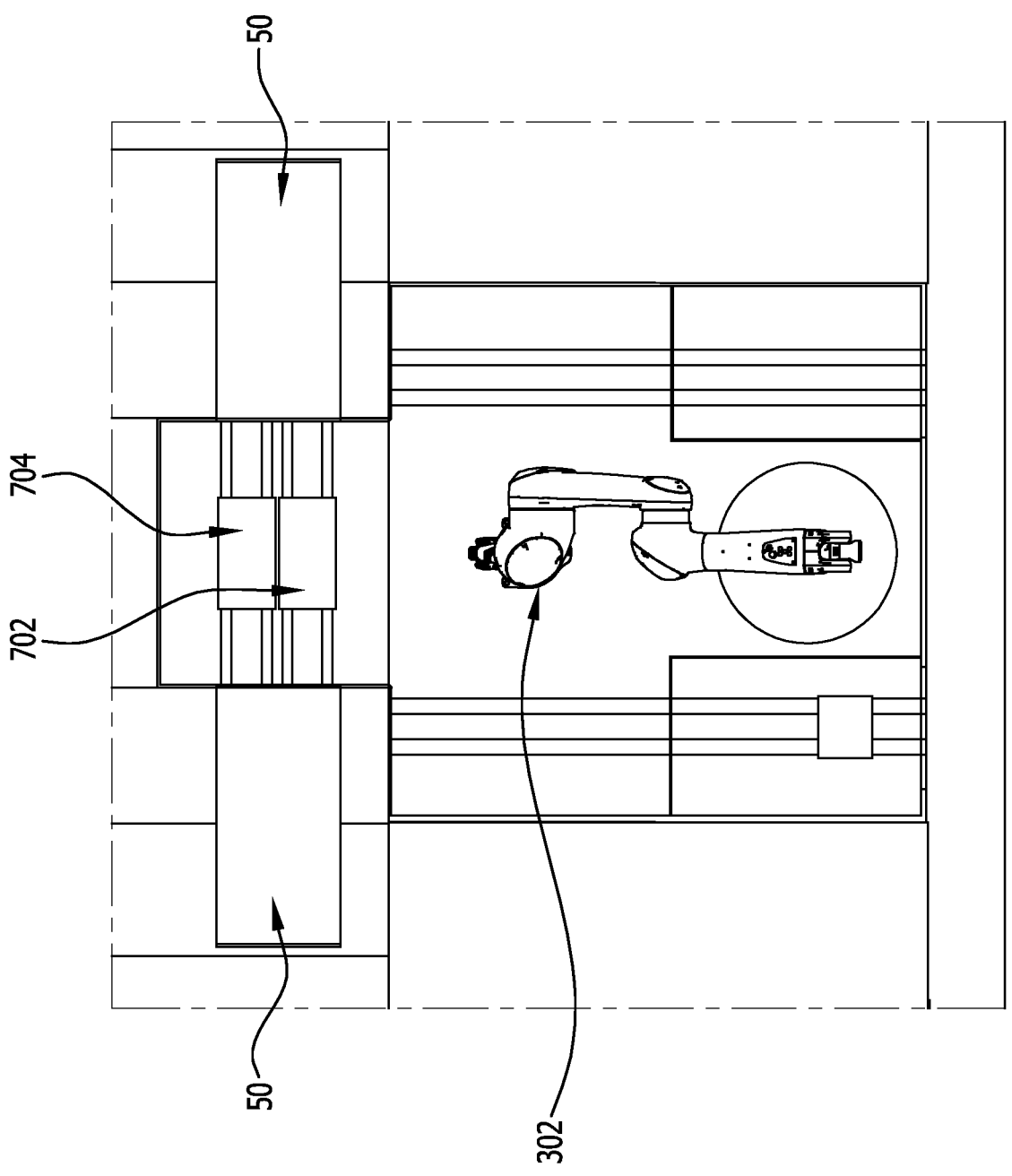
FIG. 10 is a schematic plan view of part of the production system shown in FIG. 1.

As shown schematically in FIG. 10, the tool unit 702 cleaned and sterilized by means of the cleaning device 500 is again supplied to the handling device 300.

Furthermore, a consumable material 704 is fed to the handling device 300, in particular one or more new sterile single-use components from the storage racks 404 by means of the storage transport unit 408 on a workpiece carrier 30 and/or in a further receiving box 50 (the receiving box 50 shown on the right in FIG. 10).

By means of the handling device 300, in particular the multi-axis robot arm 302, the tool unit 702 is equipped with the new consumable material 704, i.e. the new single-use components, in order to be able to be used again for one or more treatment processes.

The tool unit 702, which is again processed in this way, can again be stored at a storage space 402 on a tool carrier 30 and/or in the receiving box 50 also processed again, in particular until a new use, by means of the storage transport units 408.

Such an exemplary process described above can be carried out repeatedly until all treatment processes provided and required by a production program have been carried out at the reactant 40 and the product 20 to be produced has been generated from the reactant 40.

The reactant container 42 can now be referred to as a product container 22 in which the product 20 produced from the reactant 40 is now located.

The receiving box 50 in which the product container 22 is located is transported to the handling device 300 by means of the storage transport units 408.

There, the product container 22 is removed from the receiving box 50 by means of the handling device 300 and placed on the workpiece carrier 30, which receives the product container 22 and transports it to the packaging device 214.

The product container 22 can be supplied to the packaging device for sterile packaging by means of the multi-axis robot arm 302.

The multi-axis robot arm 302 separates the product container 22 from the workpiece carrier 30 and transfers the product container 22 to the packaging device 214, in which the product container 22 and thus the product 20 can be packaged with a sterile packaging and packaged or surrounded by means of one or more packaging units of the packaging device 214.

Figure 11:
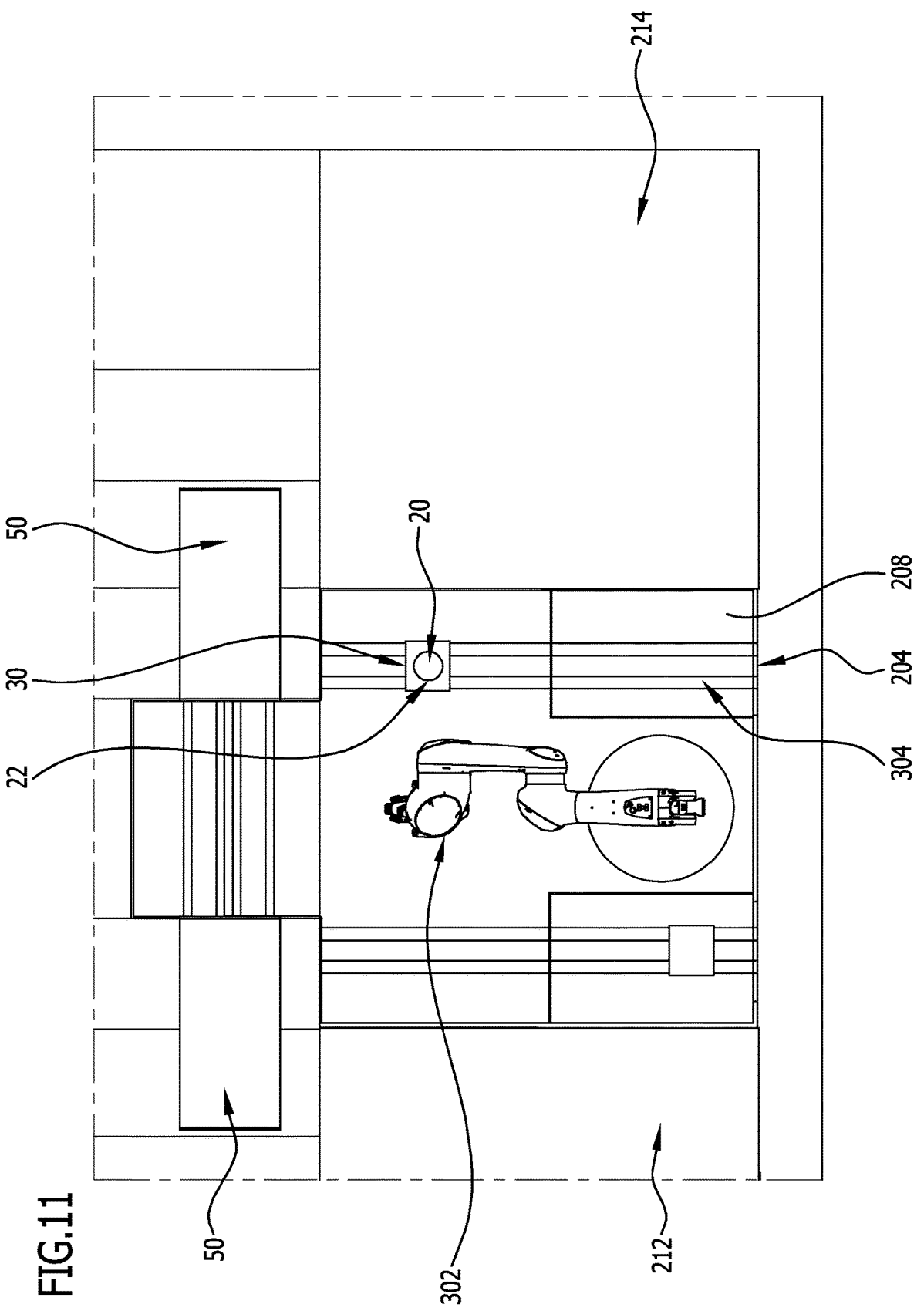
FIG. 11 is a schematic plan view of part of the production system shown in FIG. 1.

It is also conceivable here that the outlet airlock space 208 shown in FIG. 11 is used as a packaging space and is accessible by means of one or more packaging units of the packaging device 214. Furthermore, it is also conceivable that the product container 42 can be packaged in a sterile manner with the packaging by the multi-axis robot arm 302 by means of one or more packaging units.

After packaging by means of the packaging device 214, the packaged product container 22 is again transferred to the workpiece carrier 30 by means of the multi-axis robot arm 302 (cf. FIG. 11) and is supplied to the outlet airlock space 208 by means of the airlock transport device 304, where the packaged product container 22 with the product 20 can be removed by the user.

The workpiece carrier 30, on which the product container 22 was arranged, and the receiving box 50, in which the product container 22 was arranged, are supplied to the cleaning device 500 of the production system 10, as described above, and subsequently cleaned and sterilized in order to be stored again at corresponding storage spaces 402 for a next use.

Figure 12:
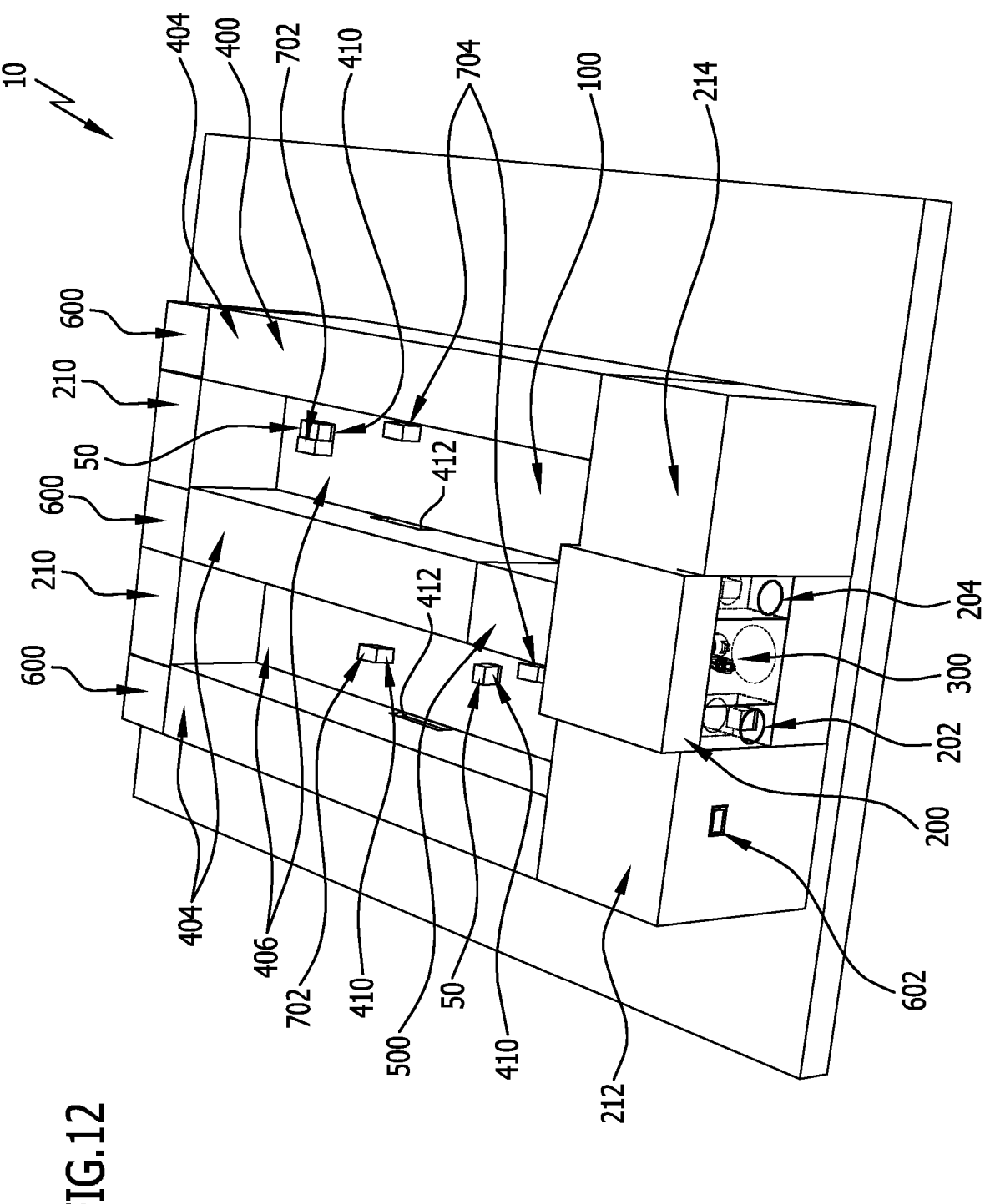
FIG. 12 is a schematic perspective view of a production system according to a further exemplary embodiment of the present invention.

FIG. 12 shows a schematic perspective view of a production system 10 according to a further exemplary embodiment of the present invention.

The production system 10 shown in FIG. 12 in accordance with a further exemplary embodiment of the present invention has substantially the same structural and functional features as the exemplary embodiment of the production system 10 according to the invention shown in FIG. 1, so that only the structural and functional differences in features are presented below.

The storage transport device 406 shown schematically in FIG. 12 comprises one or more free-moving transport vehicles 410 in the clean room region 100.

In other words, it can be provided that the transport vehicles 410, which are free-moving in the clean room region 100, are transport vehicles which can be actuated and are freely movable in the clean room region 100 according to a requirement, so that, in the event of a corresponding actuation by means of at least one of the control units, the transport vehicles are each freely-moving as required.

By means of the transport vehicles 410, the storage racks 404 of the storage device 400 are accessible in particular for storage and retrieval processes and for treatment processes and/or maintenance processes.

Figure 20:
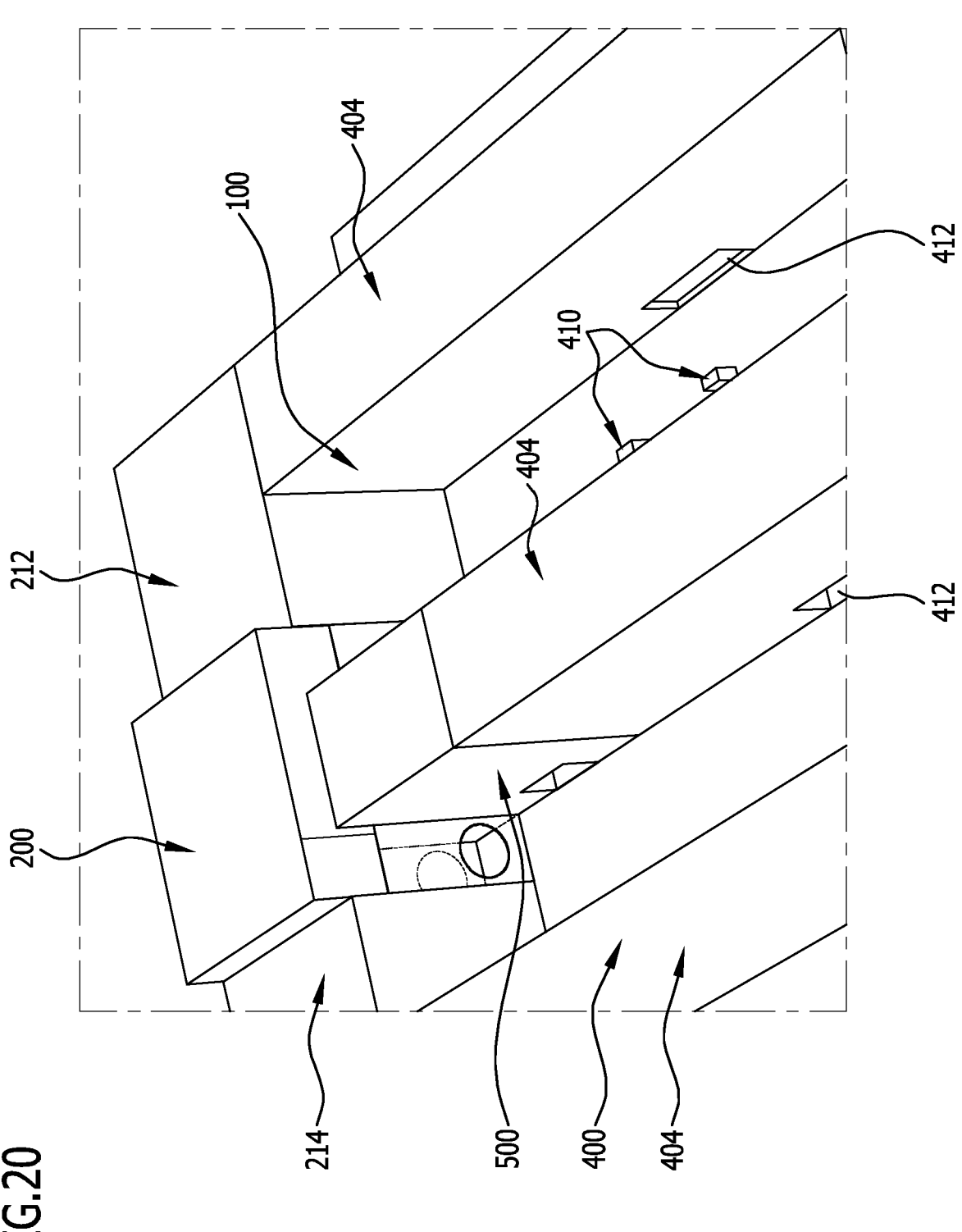
FIG. 20 is a schematic perspective view of part of the production system shown in FIG. 12.

The storage racks 404, in particular the storage spaces 402 of the storage racks 404, are accessible by the transport vehicles 410 via one or more storage rack airlocks 412 for storage and retrieval processes and for treatment processes and/or maintenance processes (cf. FIG. 20).

It is conceivable that the storage spaces 402 of the storage racks 404 are arranged on different storage space areas in the storage racks 404, which are arranged, for example, above one another and each storage space area of a storage rack 404 is accessible for the transport vehicles 410 via a, in particular common, displacement unit in the corresponding storage rack 404.

By using the free-moving transport vehicle 410, any arrangement of the storage racks 404 is also possible.

The substantially parallel arrangement of the storage racks 404 shown in FIG. 12 and in the figures relating thereto is shown purely by way of example for explanatory purposes.

Figure 13:
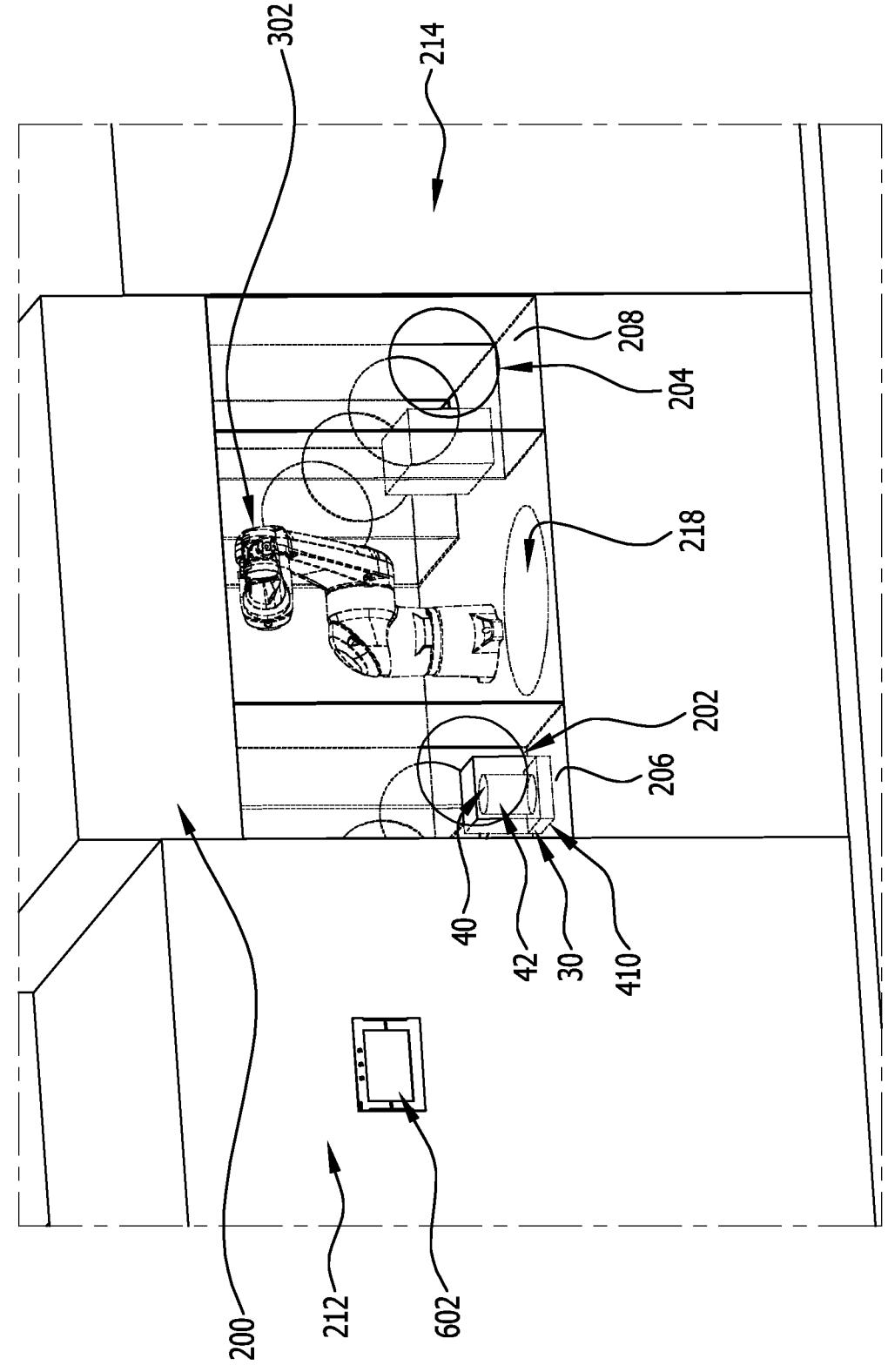
FIG. 13 is a schematic perspective view of part of the production system shown in FIG. 12.

Referring to FIG. 13, a workpiece carrier 30, on which a reactant 40 arranged in a reactant container 42 is held, is arranged on a free-moving transport vehicle 410 at the inlet airlock space 206.

Figure 14:
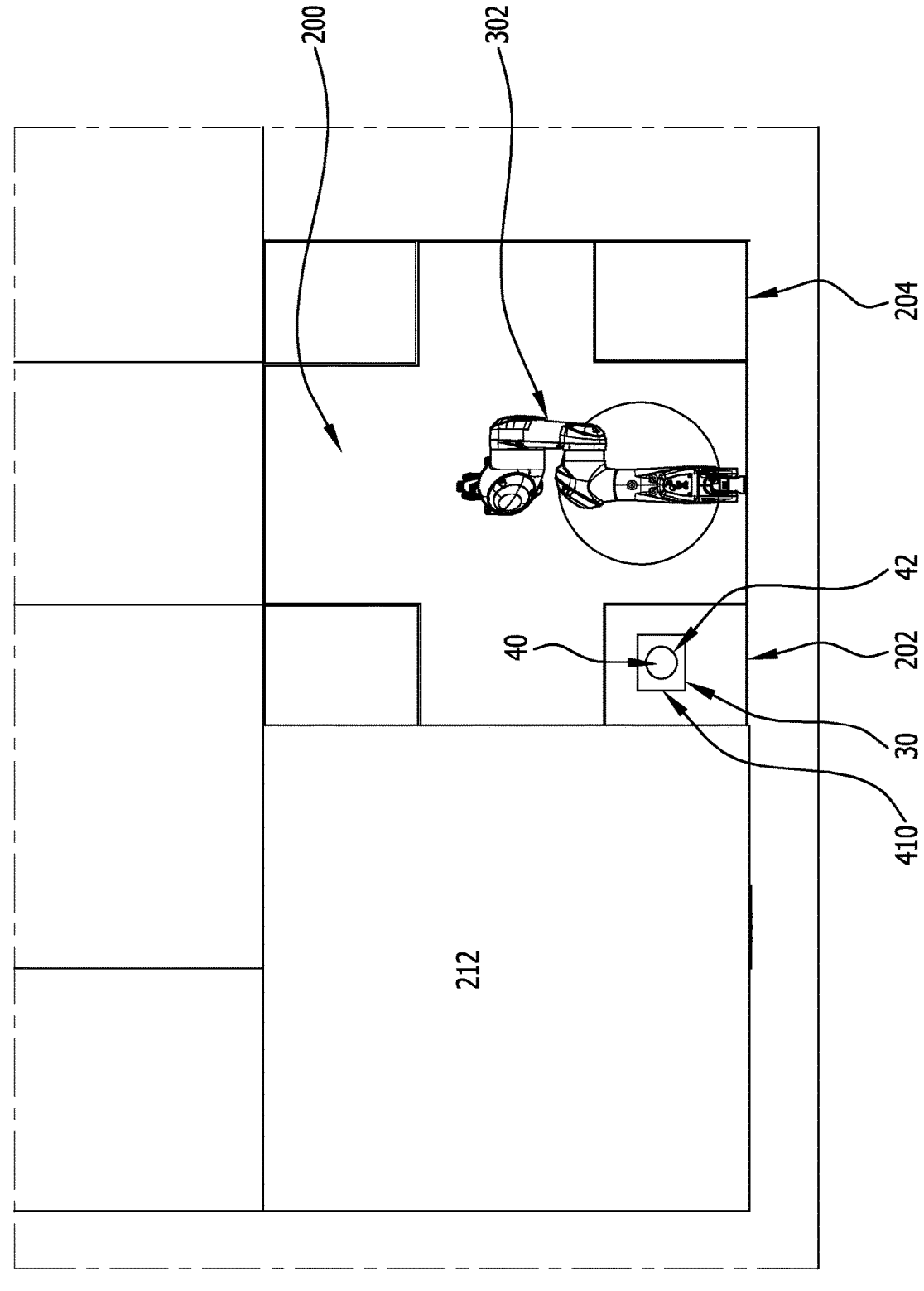
FIG. 14 is a schematic plan view of part of the production system shown in FIG. 12.

The workpiece carrier 30 shown in FIGS. 13 and 14 arranged on the transport vehicle 410 was supplied to the inlet airlock space 206 for receiving the reactant container 42 in a process not shown in the figures by means of the transport vehicle 410.

In this case, a user has first selected a production program of the production system 10, for example via the HMI interface 602, in order to produce the desired product 20 from the reactant 40.

The user then places the reactant container 42 with a reactant 40 arranged therein onto a workpiece carrier 30 provided at the inlet airlock space 206, which workpiece carrier was already provided to the inlet airlock space 206 on the transport vehicle 410 for receiving an object.

Alternatively, it is also conceivable that a workpiece carrier 30 stored at a storage space 402 of one of the storage racks 404 was removed from the storage space 402 by means of the transport vehicle 410 of the storage transport device 406 and was transported to the airlock device 200. As soon as the workpiece carrier 30 is provided at the inlet airlock space 206 for receiving the reactant 40, the reactant container 42 with a reactant 40 arranged therein is manually transferred by the user to the workpiece carriers 30 arranged on the transport vehicle 410 and fixed thereto by means of the fixing means.

As shown schematically in FIG. 15, the packaged reactant container 42 is subsequently moved on the workpiece carrier 30 by means of the transport vehicle 410 into a range of the multi-axis robot arm 302.

The multi-axis robot arm 302 separates the packaged reactant container 42 from the workpiece carrier 30 and transfers the reactant container 42 to the unpacking device 212, in which the packaging of the reactant container 42 is removable/is removed by means of one or more unpacking units of the unpacking device 212.

After the packaged reactant container 42 has been transferred to the unpacking device 212, the workpiece carrier 30 is again moved back to the inlet airlock space 206 for a renewed receiving of an object by means of the transport vehicle 410, so that substantially a state as in FIG. 14 can be present.

After unpacking by means of the unpacking device 212, the unpacked reactant container 42 is supplied to another, in particular sterile workpiece carrier 30, which is arranged in a receiving box 50 and which is provided at the transfer airlock space 216 in the receiving box 50 on another sterile transport vehicle 410 (cf. FIG. 15), by means of the multi-axis robot arm 302.

The other workpiece carrier 30 was previously retrieved together with the receiving box 50 from a storage space 402 of the storage racks 404 and was transported by means of the other transport vehicle 410 to the transfer airlock space 216.

Figure 15:
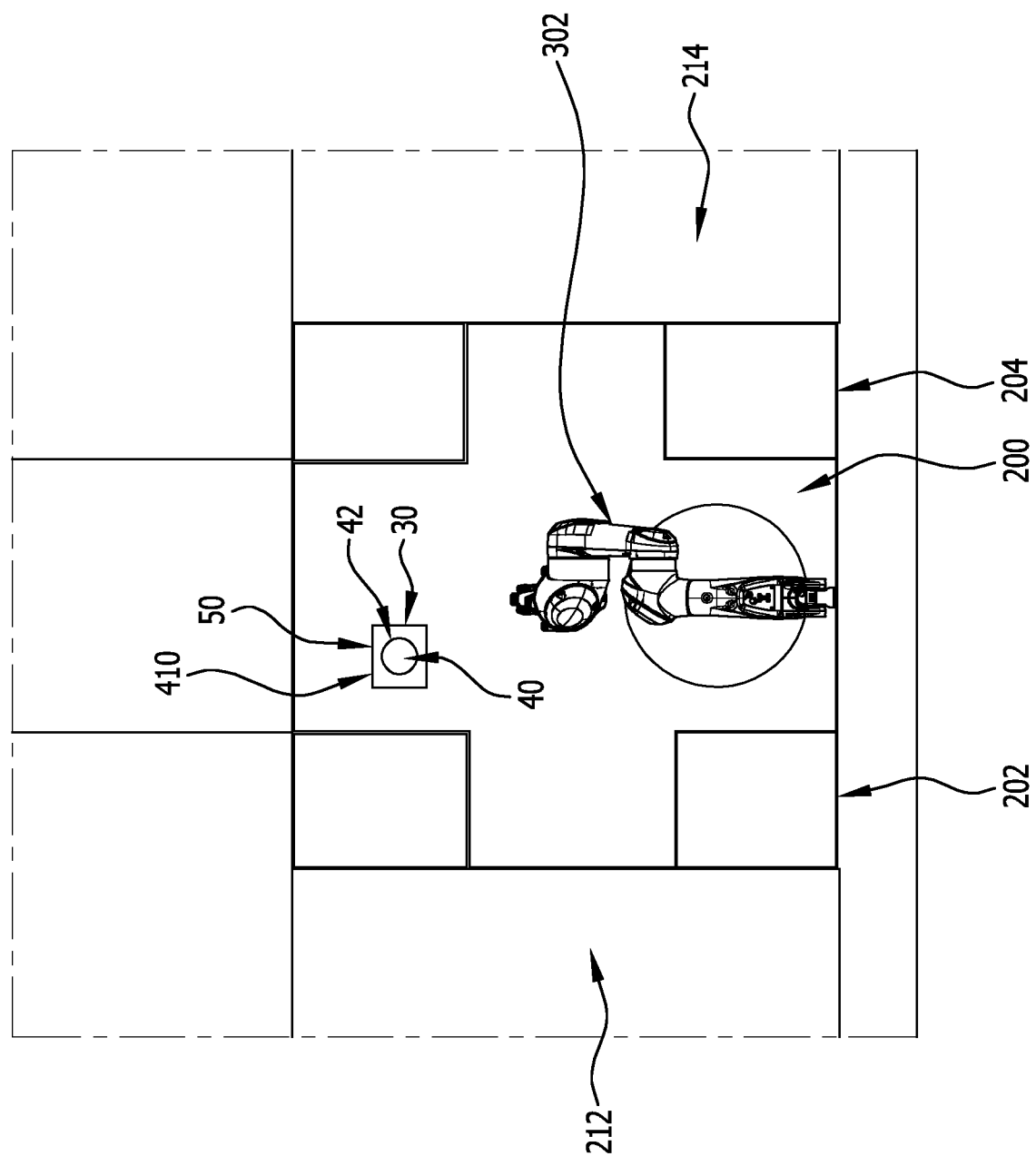
FIG. 15 is a schematic plan view of part of the production system shown in FIG. 12.
Figure 16:
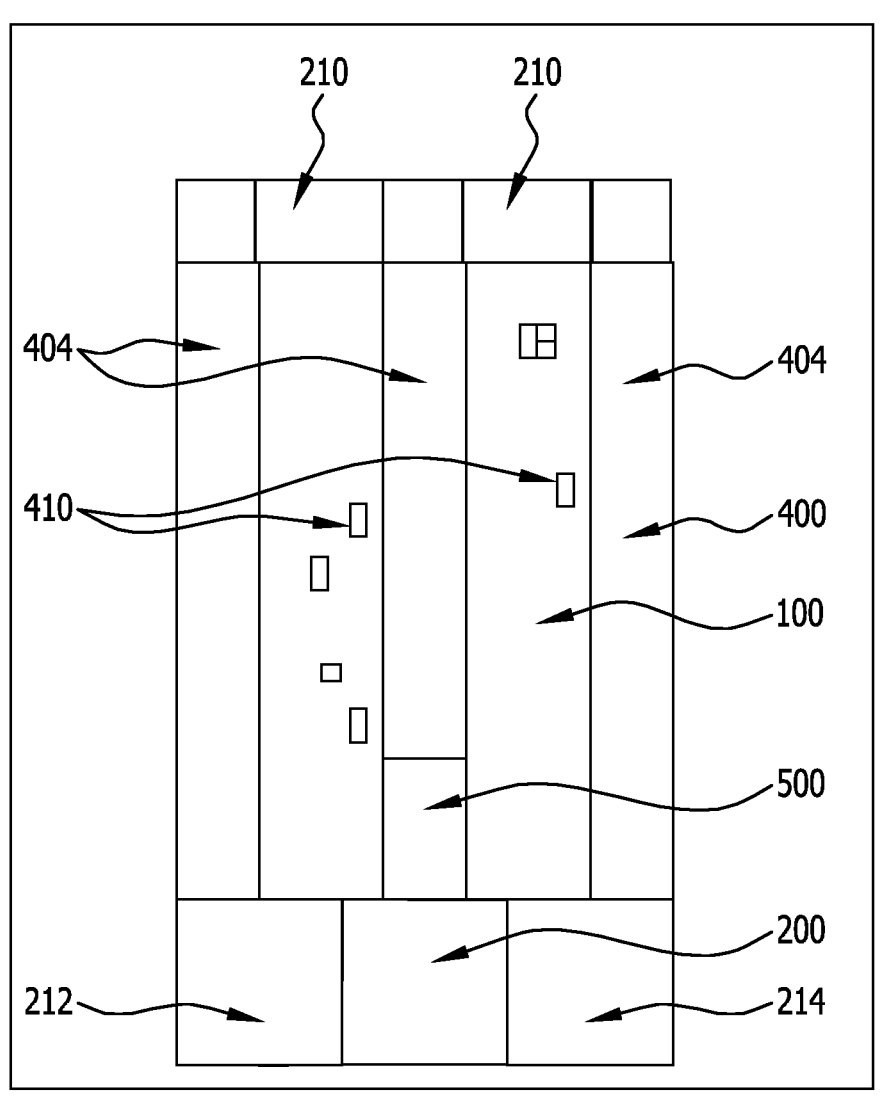
FIG. 16 is a schematic plan view of the production system shown in FIG. 12.

Referring to FIGS. 15 and 16, the receiving box 50 together with the workpiece carrier 30 arranged therein with the reactant container 42 arranged thereon is movable and storable or moved and stored at a storage space 402 in a storage rack 404 by means of the transport vehicle 410.

Figure 17:
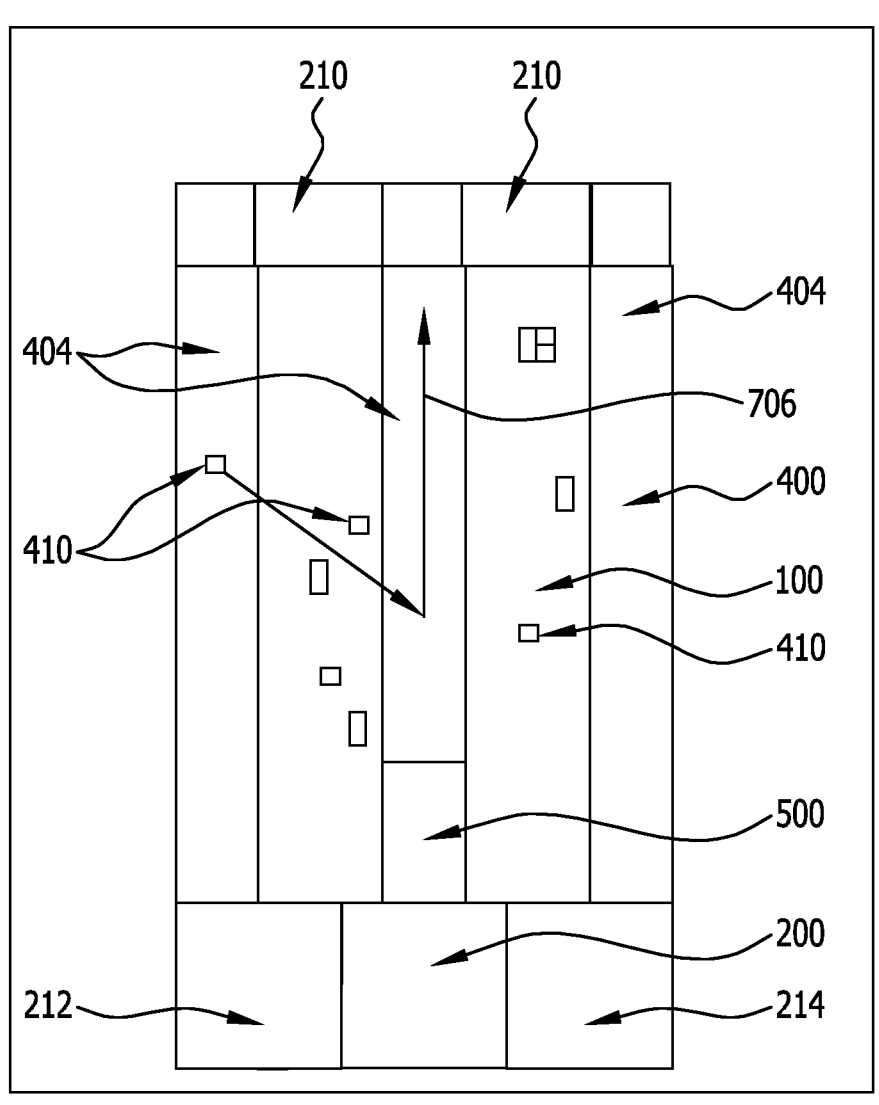
FIG. 17 is a schematic plan view of the production system shown in FIG. 12.

As shown by way of example in FIG. 17 by means of the arrows (tool path 706), for example, a tool unit 702 for carrying out one or more treatment processes is removed from the left storage rack 404 by means of a transport vehicle 410 and fed to the receiving box 50 with the reactant container 42 stored in the central storage rack 404, in order to carry out the one or more treatment processes on the reactant 40 in the reactant container 42 by means of the tool unit 702.

After carrying out the one or more treatment processes at the reactant 40, the previously supplied tool unit 702 is removed again by means of the transport vehicle 410 from the receiving box 50 which contains the reactant 40, in particular removed and transported away from or out of the receiving box 50.

Figure 18:
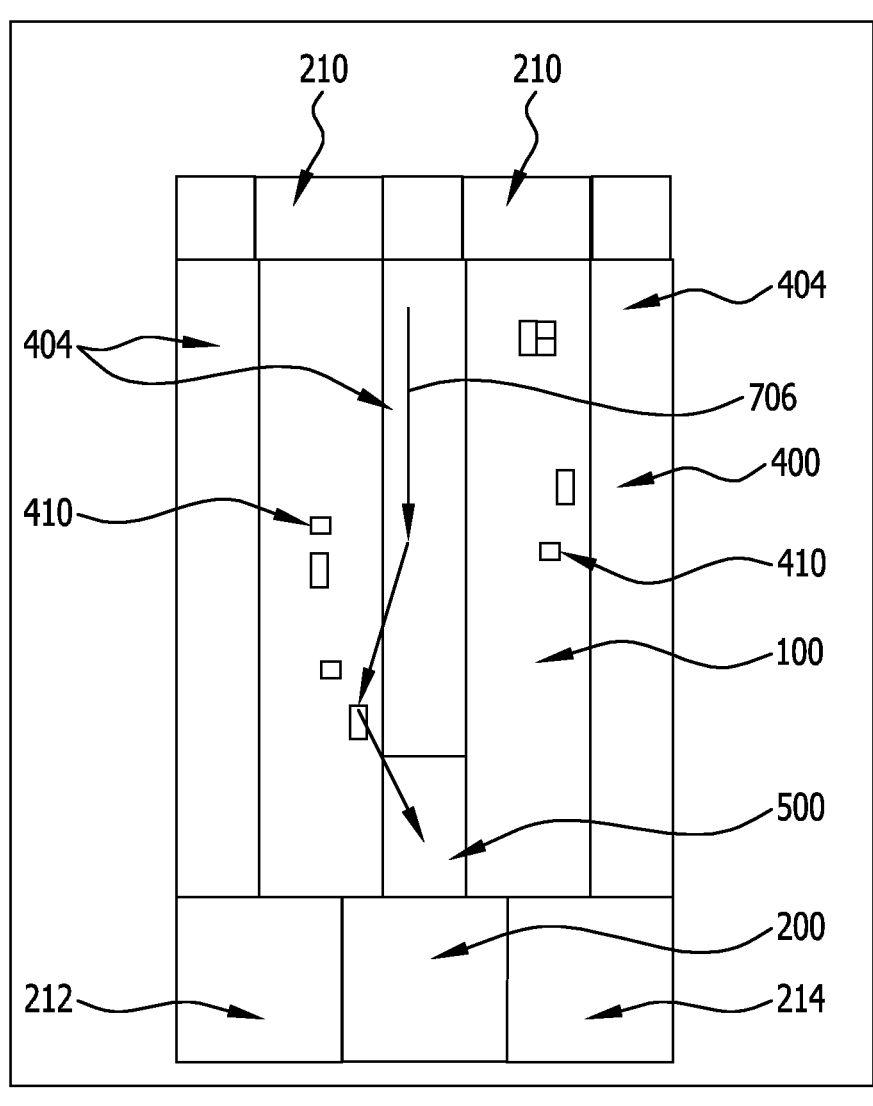
FIG. 18 is a schematic plan view of the production system shown in FIG. 12.
Figure 19:
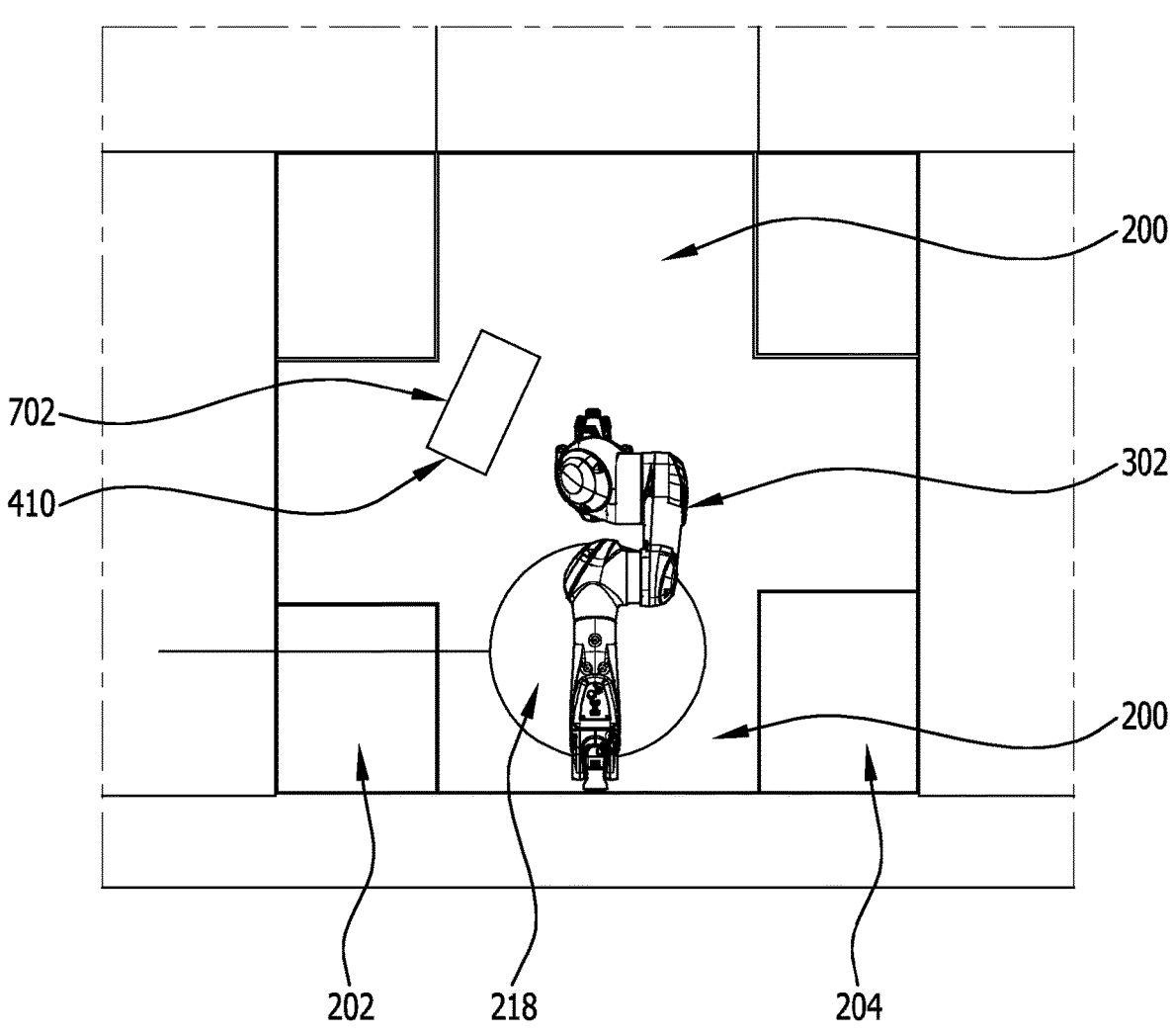
FIG. 19 is a schematic plan view of part of the production system shown in FIG. 12.

As in FIG. 18 by means of the arrows, the transport vehicle 410 transports the tool unit 702 used in its receiving box 50 to the handling device 300 in order to be removed there from the receiving box 50 by means of the handling device 300 in order to remove single-use components set up at the tool unit 702 (see FIG. 19).

Referring to FIGS. 19 and 20, the tool unit 702 used is again moved back into the receiving box 50 by means of the handling device 300 and subsequently fed to the cleaning device 500 of the production system 10 together with the receiving box 50 by means of the transport vehicle 410, by means of which the tool unit 702 used and its receiving box 50 are cleanable and sterilizable or are cleaned and sterilized.

Figure 21:
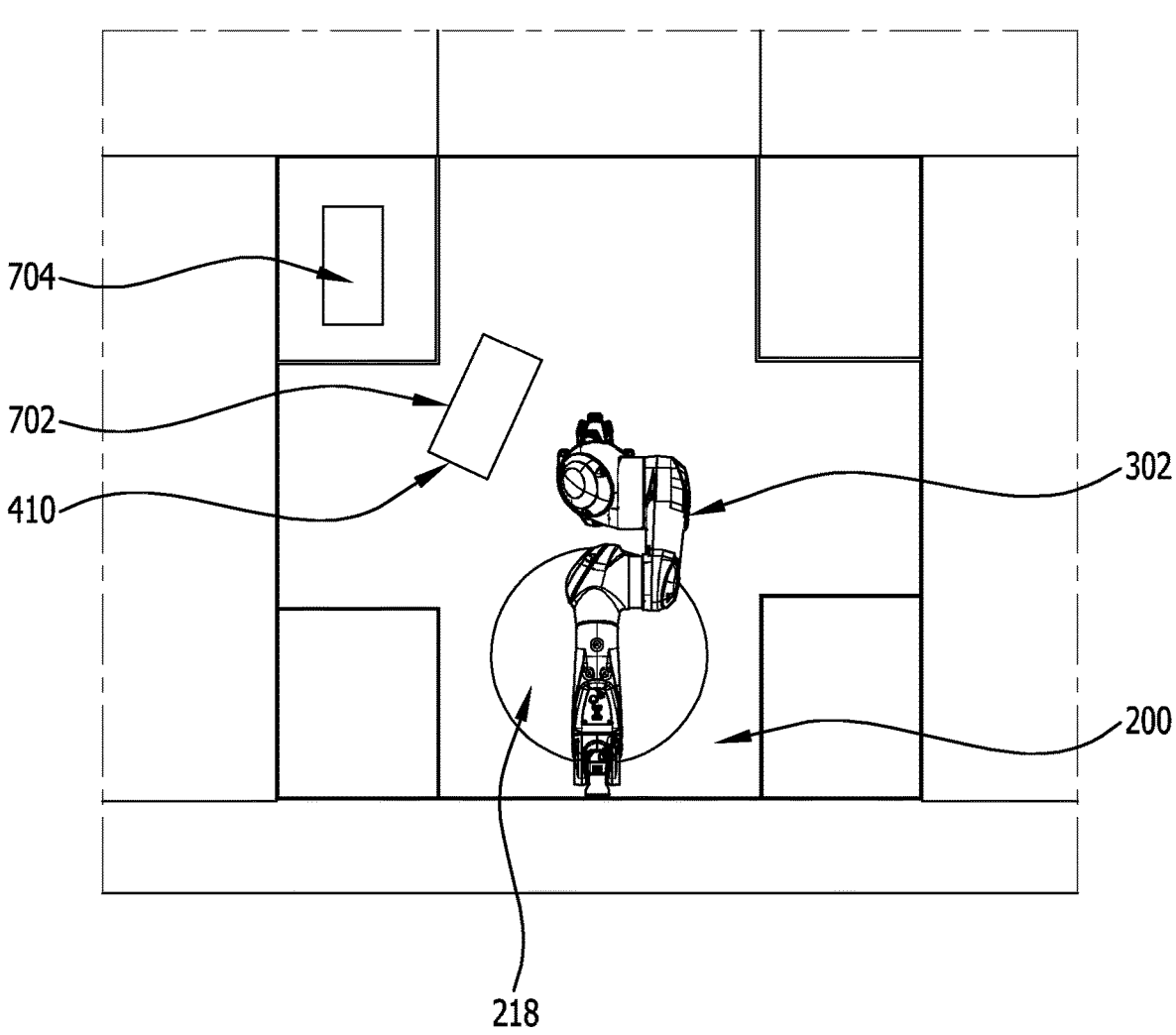
FIG. 21 is a schematic plan view of part of the production system shown in FIG. 12.

As shown schematically in FIG. 21, the tool unit 702 cleaned and sterilized by means of the cleaning device 500 is fed back to the handling device 300 by means of the transport vehicle 410, in order to again be equipped with consumable material 704, in particular one or more new sterile single-use components, from the storage racks 404 by means of the handling device 300 which was provided to the handling device 300 by means of another transport vehicle 410, for example during cleaning of the tool unit 702 used.

In parallel or in series thereto, the produced product 20, which is arranged in a product container 22, is transported out of the storage rack 404 by means of a further transport vehicle 410 and to the transfer airlock space 216 in order to be packaged by means of the packaging device 214.

Figure 22:
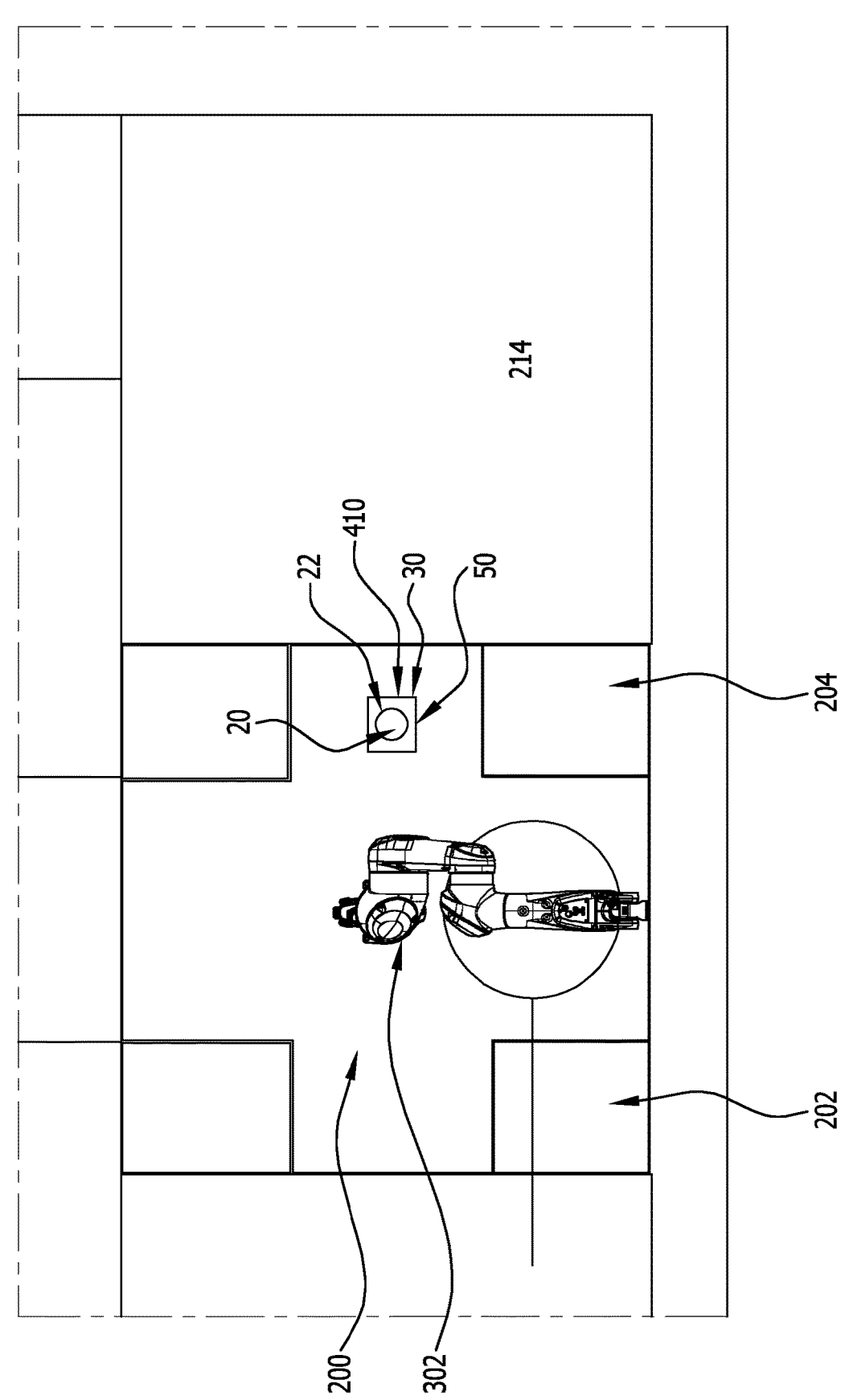
FIG. 22 is a schematic plan view of part of the production system shown in FIG. 12.

After packaging by means of the packaging device 214, the packaged product container 22 is again transferred to the workpiece carrier 30 by means of the multi-axis robot arm 302 (cf. FIG. 22) and is supplied to the outlet airlock space 208 by means of the transport vehicle 410, where the packaged product container 22 with the product 20 can be removed by the user.

Figure 23:
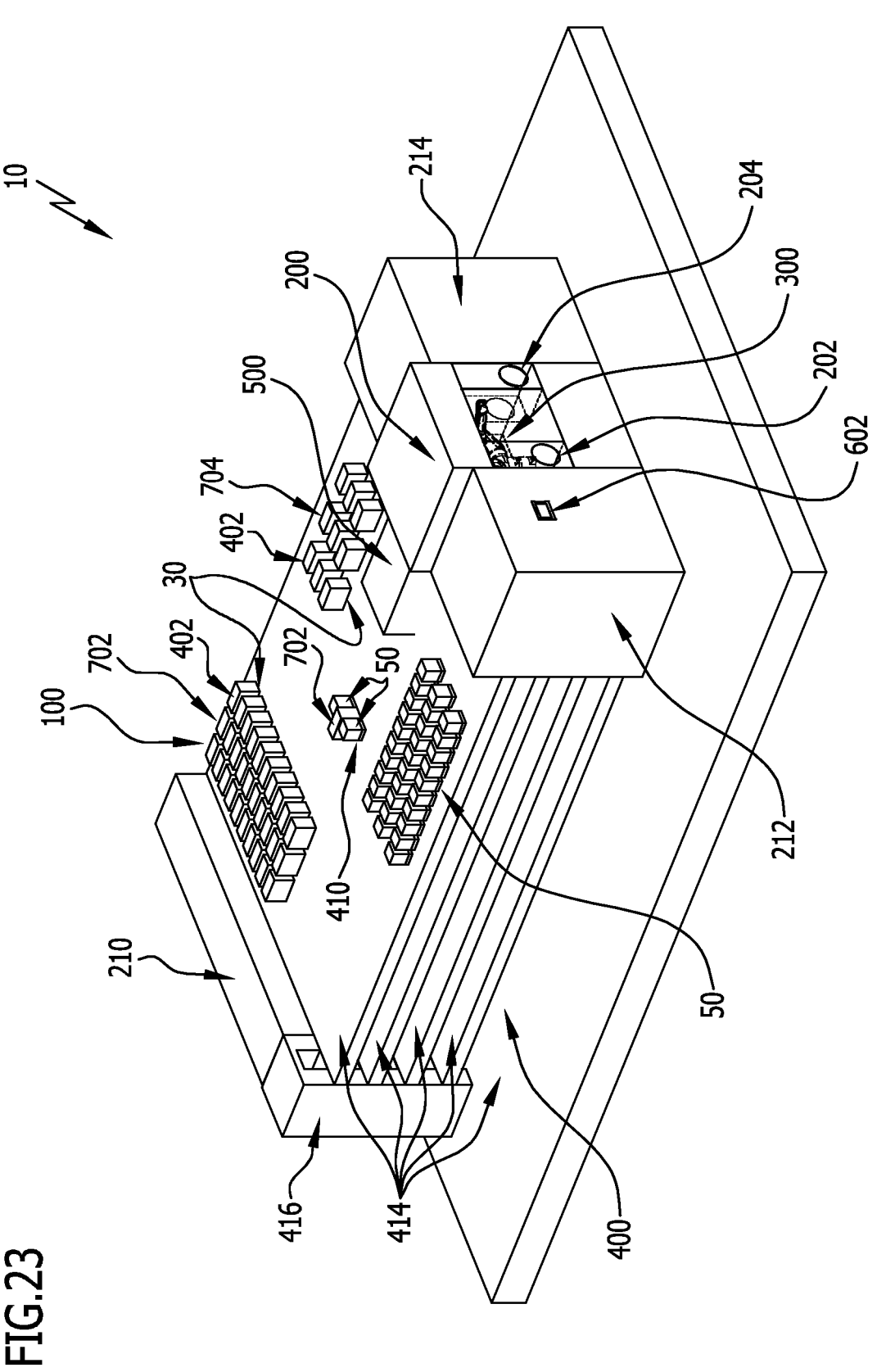
FIG. 23 is a schematic perspective view of a production system according to a further exemplary embodiment of the present invention.

FIG. 23 shows a schematic perspective view of a production system 10 according to a further exemplary embodiment of the present invention.

The production system 10 shown in FIG. 23 in accordance with a further exemplary embodiment of the present invention has substantially the same structural and functional features as the exemplary embodiment of the production system 10 according to the invention shown in FIG. 1, so that only the structural and functional differences in features are presented below.

The storage transport device 406 comprises one or more free-moving transport vehicles 410, which have already been described in conjunction with the exemplary embodiment of the production system 10 according to the invention shown in FIG. 12.

The storage device 400 comprises a plurality of storage space areas 414, here four, which each have a plurality of storage spaces 402.

The storage space areas 414 are arranged one above the other in particular in a height direction.

To a certain extent, the storage space areas 414 are arranged in a stacked manner, as is shown schematically in FIG. 23.

Different types of storage spaces 402 for receiving different types of objects are arranged on the storage space areas 414.

As shown schematically in FIG. 23, the different types of storage spaces 402 are distributed in a regular pattern.

For example, a plurality of, in particular all, receiving boxes 50, and a plurality of, in particular all, tools 702, which are arranged in particular on corresponding workpiece carriers 30, and a plurality of, in particular all, consumable materials 704, which are arranged in particular on corresponding workpiece carriers 30, are arranged spatially adjacently in said pattern.

The storage transport device 406 further comprises one or more elevator devices 416, by means of which the storage space areas 414 of the storage device 400 are accessible in particular for storage and retrieval processes and for treatment processes and/or maintenance processes.

The transport vehicles 410 are movable to the individual storage space areas 414 by means of the elevator devices 416.

Additionally or alternatively, it is conceivable that, by means of the elevator devices 416, a transfer process of a transported object from a transport vehicle 410, which is located on a storage space area 414, to another transport vehicle 410, which is located on another storage space area 414, can be carried out. In some cases, such a transfer process can be carried out from one transport vehicle 410 to another transport vehicle 410 via the elevator devices 416.

Figure 24:
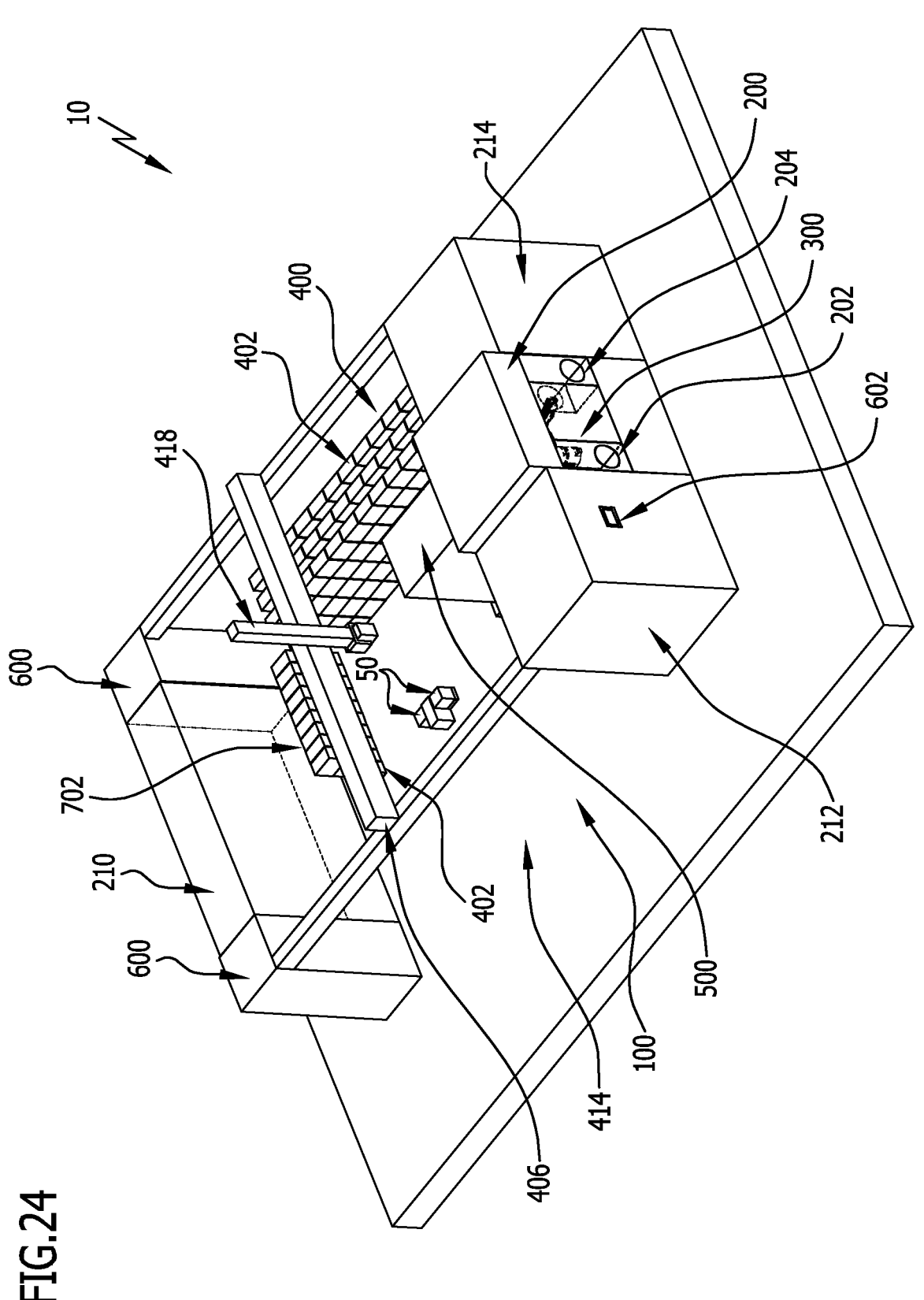
FIG. 24 is a schematic perspective view of a production system according to a further exemplary embodiment of the present invention.

In FIG. 24, a schematic perspective view is shown of a production system 10 according to a further exemplary embodiment of the present invention.

The production system 10 according to a further exemplary embodiment of the present invention shown in FIG. 24 has substantially the same structural and functional features as the exemplary embodiment of the production system 10 according to the invention shown in FIG. 1, so that only the structural and functional differences in features are presented below.

The storage device 400 comprises a storage space area 414 which has a plurality of storage spaces 402.

Different types of storage spaces 402 for receiving different types of objects are arranged on the storage space area 414.

As shown schematically in FIG. 24, the different types of storage spaces 402 are distributed in a regular pattern.

For example, a plurality of, in particular all, tools 702, which are arranged in particular on corresponding workpiece carriers 30, and a plurality of, in particular all, consumable materials 704, which are arranged in particular on corresponding workpiece carriers 30, are arranged spatially adjacently in said pattern.

The storage transport device 406 comprises a storage transport unit 408 designed as a gantry conveyor 418, wherein the storage space area 414 is accessible, in particular for storage and retrieval processes, and for treatment processes and/or maintenance processes by means of the gantry conveyor 418.

Figure 25:
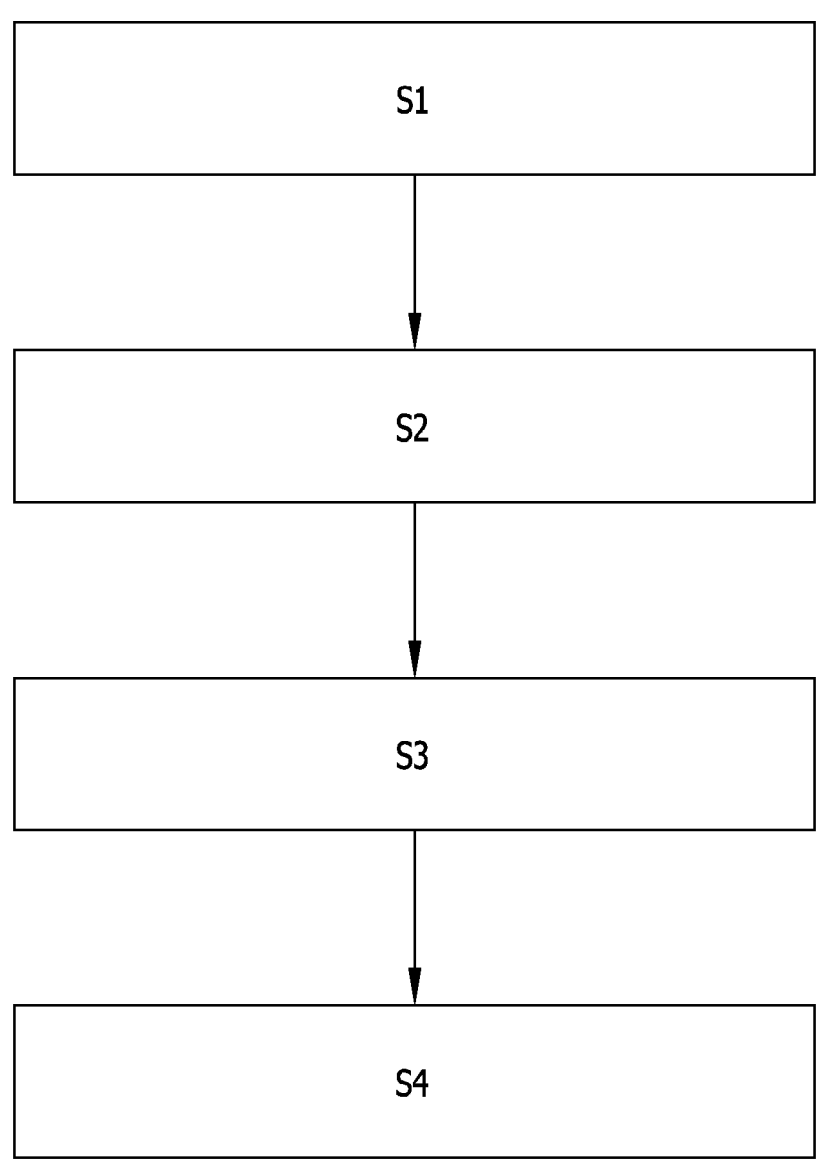
FIG. 25 shows a method according to an exemplary embodiment of the present invention.

In FIG. 25 a method according to an exemplary embodiment of the present invention is outlined.

The method for producing a biological-pharmaceutical product 20 by means of a production system, in particular the production system 10 described above, comprises:

selecting one of a plurality of production programs for producing one of a plurality of products 20 producible by means of the production system 10 (S1);

introducing a reactant 40 into an airlock device 200 of the production system 10 (S2);

automatically transporting the reactant 40 into a clean room region 100 of the production system 10, wherein, optionally, the reactant 40 is stored in a storage space 402 of a storage device 400 of the production system 10 located within the clean room region 100 (S4);

automatically carrying out one or more treatment processes on the reactant 40 (S4).

In S4, one or more treatment processes are carried out fully automatically until a product 20 to be produced from the reactant 40 is completed.

In S4, one or more, in particular all, treatment processes can be carried out at the storage space 402.

The product 20 that is producible or produced in S4 is retrieved from the storage space 402 and transported automatically to the airlock device 200 for the removal of same from the production system 10.

The product 20 is filled and/or packaged, in particular filled and/or packaged ready for use, in a step downstream of S4 before the removal of the product.

One or more vessels, receptacles and/or tools which have been used for the production of the product 20 remain at least partially within the clean room region 100 after the product 20 has been completed, are cleaned and are then reused for producing a further product 20.

In order to produce the product 20 and/or to produce a plurality of different products 20, required consumable materials 704, in particular consumable substances and/or tool consumables, are stored within the clean room region 100, in particular before a selection of the product 20 to be produced is/has been made.

The consumable materials 704 are automatically transported into the clean room region 100 via the airlock device 200 and stored there in particular in one or more storage spaces 402 of the storage device 400.

An amount of the consumable materials 704 stored within the clean room region 100 is monitored and, when a predefined minimum amount is undershot, the supply is increased by supplying the required consumable materials 704, in particular via an indication or a warning message at an operator unit, for example the HMI interface 602.

A plurality of products 20, in particular a plurality of different products 20, can be produced simultaneously within the clean room region 100.

To a certain extent, the method can be carried out or executed simultaneously and/or with different time shifts.

One or more treatment processes which can be carried out in particular by means of one or more tool units 702 comprise:

supplying a liquid and/or a gas, in particular a gas mixture, discharging, in particular pumping off, a liquid and/or a gas, in particular a gas mixture, discharging, in particular pumping off, a portion of a liquid and/or a gas, in particular a gas mixture, for an analysis by means of one or more sensor units, mixing one or more components, in particular at least one liquid, with at least one further component, for example a further liquid, concentrating and/or separating a liquid, in particular by means of a column, for example a separation column, and/or a centrifuge, analyzing a reactant and/or an intermediate product and/or a product, in particular by means of one or more sensor units, storing, in particular placing into storage and/or retrieving, one or more objects, in particular by means of the storage transport device 406, controlling the temperature of, in particular incubating, one or more objects, in particular one or more reactants 40.

It should be understood that the preceding list of the treatment processes is exemplary and not exhaustive.

Alternatively or additionally, it is provided that one or more treatment processes can be combined with one or more treatment processes in a single treatment process and/or in any combination thereof.

A sequence of treatment processes, which are carried out by means of tools 702 arranged within the clean room region 100 and remaining in the clean room region 100 after the treatment processes have been carried out, is associated with each product 20 to be produced.

One or more tools 702 are cleaned, in particular sterilized, after one or more treatment processes within the clean room region are carried out.

One or more tools 702 are equipped with tool consumables, in particular single-use components, before one or more treatment processes within the clean room region 100 are carried out.

One or more tool consumables are removed from the one or more tools 702 and/or disposed of after one or more treatment processes within the clean room region 100 have been carried out.

A plurality of, in particular all, treatment processes are associated with treatment time values which indicate that time period which elapses from a start of the corresponding treatment process up to its end, in particular including:

a time period for providing the at least one tool 702 required for the corresponding treatment process, in particular including its equipping with one or more tool consumables, and/or a time period for the supply and/or arrangement and/or startup of the at least one tool 702 on the reactant 40 to be treated, in particular at a storage space 402 at which the reactant 40 is arranged, and/or a duration of the effect on the reactant 40 in order to achieve a desired treatment result, and/or a time period for removing the at least one tool 702 from the reactant 40, in particular from the storage space 402;

preferably including:

cleaning of the at least one tool 702, and/or removing and/or disposing of tool consumables, and/or a return transport of the tool 702 to a starting location, in particular a storage space 402 associated with the tool 702.

In each production program, the treatment processes required for the production of a specific product 20 and associated treatment time values are stored or taken into account.

When a production program is started, a prediction of a production sequence is created and the tools 702 required and/or provided for carrying out the treatment processes are reserved for time slots resulting from the prediction.

One or more treatment processes are each assigned one or more cleaning processes for cleaning one or more tools 702 and/or for cleaning one or more storage spaces 402, and/or one or more disposal processes for disposing of consumable materials 704, and/or one or more set-up processes for equipping one or more tools 702 with consumable materials 704, and/or one or more control processes for controlling a treatment result, wherein, depending on the prediction of the production process, time slots are reserved at one or more of those devices that are required for carrying out the one or more cleaning processes, the one or more disposal processes, the one or more set-up processes, and/or the one or more control processes.

After one or more treatment processes, in particular after each treatment process, the prediction of the production sequence is checked and/or updated, in particular for confirming or correcting the time slots for the tools 702 that are still required and/or other devices for completing the product 20.

At a desired start of a production program, it is determined on the basis of a prediction of the production sequence whether all required tools 702 and/or other devices for finishing the product 20 are available within the required time slots, and the production program is only started if this determination has supplied a positive result.

Regarding the method outlined in FIG. 25, it should be understood that all structural and functional features which are connected to the production system according to the invention and in particular to the previously described embodiments of the production system 10 can also be included in the method according to the invention either alone or in combination, and the associated properties, configurations and advantages can likewise be correspondingly included and achieved. The production system 10 described above is also configured to carry out the method outlined in FIG. 25, and the method outlined in FIG. 25 is furthermore designed to be executable by means of the production system 10 described above.

The invention claimed is:

1. A production plant, for producing biological-pharmaceutical products, wherein the production plant comprises the following:

a clean room region;

a lock device being configured to feeding an object from an environment of the production plant into the clean room region and/or being configured to remove an object from the clean room region;

a handling device being configured to move the object within the clean room region; and a storage device arranged within the clean room region, which comprises a plurality of storage locations for receiving a plurality of objects, wherein the production plant comprises an unpacking device being configured to unpack objects to be fed to the clean room region, and the unpacking device comprises a plurality of unpacking units being configured to unpack different types of objects and/or packaging, and/or being configured to remove different types of packaging from the objects.

2. The production plant according to claim 1, wherein the unpacking device is integrated into the lock device or forms a component thereof.

3. The production plant according to claim 1, wherein the lock device comprises an entrance lock location which is accessible from the environment of the production plant and on which a packed object can be arranged.

4. The production plant according to claim 3, wherein the packed object can be transported from the entrance lock location to an unpacking location by means of a lock transport device of the production plant and can be unpacked automatedly at the unpacking location, or in that the packed object can be unpacked automatedly at the entrance lock location.

5. The production plant according to claim 1, wherein the lock device comprises a cleaning device being configured to clean a packaging of the packed object.

6. The production plant according to claim 1, wherein one or more unpacking units are designed for unpacking reactants and one or more further unpacking units are designed for unpacking tools and/or consumables.

7. The production plant according to claim 1, wherein the unpacking device comprises a detection device and a control device by means of which a type of the object to be unpacked and/or a type of the packing to be removed can be determined.

8. The production plant according to claim 7, wherein an unpacking unit of the unpacking device for carrying out the unpacking process can be selected and controlled by means of the control device, the unpacking unit being one of a plurality of unpacking units for carrying out different unpacking processes, the selected unpacking unit being associated with the determined type of object to be unpacked and/or the type of the packaging to be removed.

9. The production plant according to claim 1, wherein the lock device comprises an entrance lock location which is accessible from the environment of the production plant and on which a packed object can be arranged by a person or automatedly.

10. The production plant according to claim 9, wherein the packed object can be transported from the entrance lock location to an unpacking location by means of a lock transport device of the production plant and can be unpacked automatedly at the unpacking location, or in that the packed object can be unpacked automatedly at the entrance lock location.

* * * * *